US010336755B2

(12) United States Patent
Chen et al.

(10) Patent No.: US 10,336,755 B2
(45) Date of Patent: Jul. 2, 2019

(54) FUSED PYRAZOLE DERIVATIVES, PREPARATION METHOD THEREOF, AND USE THEREOF IN TREATMENT OF CANCERS, INFLAMMATION AND IMMUNE DISEASES

(71) Applicant: Beijing InnoCare Pharma Tech Co., Ltd., Beijing (CN)

(72) Inventors: Xiangyang Chen, Beijing (CN); Yucheng Pang, Beijing (CN)

(73) Assignee: Beijing Innocare Pharma Tech Co., Ltd., Beijing (CN)

( * ) Notice: Subject to any disclaimer, the term of this patent is extended or adjusted under 35 U.S.C. 154(b) by 0 days.

(21) Appl. No.: 16/073,607

(22) PCT Filed: Dec. 28, 2016

(86) PCT No.: PCT/CN2016/112625

§ 371 (c)(1),
(2) Date: Jul. 27, 2018

(87) PCT Pub. No.: WO2017/128917

PCT Pub. Date: Aug. 3, 2017

(65) Prior Publication Data

US 2019/0016721 A1 Jan. 17, 2019

(30) Foreign Application Priority Data

Jan. 29, 2016 (CN) .......................... 2016 1 0066886

(51) Int. Cl.

| | |
|---|---|
| ***C07D 471/06*** | (2006.01) |
| ***A61K 31/437*** | (2006.01) |
| ***C07D 471/22*** | (2006.01) |
| ***A61K 31/519*** | (2006.01) |
| ***C07D 471/04*** | (2006.01) |
| ***C07D 487/04*** | (2006.01) |
| ***A61P 37/00*** | (2006.01) |
| ***A61P 35/00*** | (2006.01) |
| ***C07D 401/04*** | (2006.01) |
| ***C07D 401/14*** | (2006.01) |

(52) U.S. Cl.

CPC .......... *C07D 471/22* (2013.01); *A61K 31/437* (2013.01); *A61K 31/519* (2013.01); *A61P 35/00* (2018.01); *A61P 37/00* (2018.01); *C07D 401/04* (2013.01); *C07D 401/14* (2013.01); *C07D 471/04* (2013.01); *C07D 487/04* (2013.01)

(58) Field of Classification Search

CPC ............................ C07D 471/06; A61K 31/437
USPC ........................................... 546/119; 514/303
See application file for complete search history.

(56) References Cited

U.S. PATENT DOCUMENTS 8,008,481 B2 * 8/2011 Ericsson ............. C07D 403/12 544/119

FOREIGN PATENT DOCUMENTS

| | | | |
|---|---|---|---|
| CN | 101107250 | A | 1/2008 |
| WO | 2007117465 | A2 | 10/2007 |
| WO | 2011058025 | A1 | 5/2011 |
| WO | 2015004533 | A2 | 1/2015 |
| WO | 2015048689 | A1 | 4/2015 |

* cited by examiner

*Primary Examiner* — Charanjit Aulakh
(74) *Attorney, Agent, or Firm* — Fox Rothschild LLP

(57) ABSTRACT

The present invention relates to pyrazole fused-ring derivatives, their preparation methods, and use thereof in medicine. In particular, the present invention relates to a novel derivative represented by formula (I), and a pharmaceutically acceptable salt thereof or a pharmaceutical composition comprising the same and a method for preparing the same. The present invention also relates to use of the derivatives and the pharmaceutically acceptable salt thereof or the pharmaceutical composition comprising the same in the preparation of therapeutic agents, in particular Bruton tyrosine kinase inhibitors, and preparing a medicament for treating and/or preventing tumors and inflammatory associated diseases. The substituents on formula (I) are defined same as in the specification.

(I)

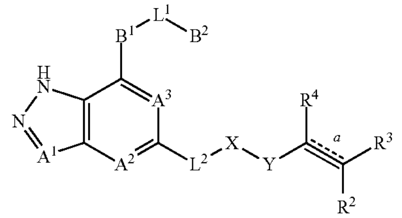

7 Claims, No Drawings

FUSED PYRAZOLE DERIVATIVES, PREPARATION METHOD THEREOF, AND USE THEREOF IN TREATMENT OF CANCERS, INFLAMMATION AND IMMUNE DISEASES

TECHNICAL FIELD

The present invention relates to novel fused pyrazole derivatives and their pharmaceutically acceptable salts thereof or pharmaceutical compositions comprising these compounds, and to methods of preparing these compounds. The present invention also relates to use of the fused pyrazole derivatives and their pharmaceutically acceptable salts thereof or the pharmaceutical compositions comprising these compounds in the preparation of therapeutic agents, especially as a Bruton tyrosine kinase inhibitor, and to use of the fused pyrazole derivatives and their pharmaceutically acceptable salts thereof or the pharmaceutical compositions in the preparation of medicaments for treating and/or preventing tumors and inflammatory diseases.

BACKGROUND

Bruton tyrosine kinase (BTK) is an important member of Tec tyrosine kinase family, which is present in plasmocytes including B cells, mastocytes and macrophages, and plays a decisive role in the B cell receptor (BCR) mediated signal pathway. When BTK is activated by upstream Src family kinases, it phosphorylates downstream phospholipases C (PLC), thereby activating the PI3 and DAG signal pathway. This signal pathway promotes the proliferation, adhesion and survival of cells, and plays an important role in the development of B cell lymphomas.

By inhibiting the activity of BTK, BTK inhibitors can inhibit the proliferation of B cell lymphoma cells, destroy the adhesion of tumor cells, and promote the apoptosis of tumor cells, so that BTK becomes a drug target of interest in B cells-associated cancers, especially B cell lymphoma and leukemia, for example, non-Hodgkin's lymphoma (NHL), chronic lymphocytic leukemia (CLL), and mantle cell lymphoma (MCL), etc. Currently, the only drug with BTK specific inhibition in market is Ibrutinib from Pharmacyclics/JNJ. Ibrutinib is an irreversible small molecule BTK inhibitor, which has significant efficacy on the treatment of MCL, CLL, WM, etc., and is safe. Other BTK inhibitors entering clinical trials for targeting cell lymphomas comprise CC-292 from Celgene company, ACP-196 from Acerta company, ONO-4059 from ONO Company, and BGB-3111 from Beigene Company, and so on.

In addition to anti-B cell lymphomas and anti-leukemia effects, BTK inhibitors can further inhibit the production of B cell autoantibodies and cytokines. Mutations in BTK can lead to a rare genetic disease—X-Linked Agammaglobulinemia (XLA). Because the function of BTK is inhibited in this disease, resulting in inhibition of the production or maturation of B cells and reduction of the circulating antibodies, the patients are prone to serious and even fatal infections. Pre-clinical animal model studies showed that BTK gene-deficient mice can resist to collagen-induced arthritis, and clinical results also demonstrated that Rituxan, an antibody drug for B cell depletion, is efficacious for the treatment of immune disorders. Therefore, the BTK inhibitors can also be used for treating autoimmune-related diseases, such as rheumatoid arthritis (RA), systemic lupus erythematosus (SLE), anaphylactic diseases (such as, esophagitis, eosoniphilic esophagitis), and so on. Currently, there are not yet a BTK specific inhibitor for use in immune diseases in the market, but several are in clinical stages, for example, CC-292 from Celgene Company, HM-71224 from Hanmi, PRN-1008 from Principia, and a compound from Pharmacyclics.

As BTK plays an important role in a plurality of signaling pathways, the development of BTK inhibitors has attracted attention from many biopharmaceutical companies. A series of patent applications on BTK inhibitors have been disclosed, including WO2007087068, WO2010126960, WO2011019780, WO2011090760, WO2012135801, WO2012158764, WO2013060098, WO2013081016, WO2013010869, WO2013113097, CN103113375, WO2014068527, WO2014125410, WO2014173289, WO2013118986, WO2015017502, WO2015048689, etc. However, there is still a need to develop new compounds with better efficacy. With continuous efforts, the inventor designs a compound having the structure of formula (I), and finds that the compounds having such structure exhibit excellent effects and functions.

SUMMARY OF THE INVENTION

The present invention is to provide a compound represented by formula (I) or its tautomers, mesomers, racemates, enantiomers, diastereoisomers, mixtures thereof, or a pharmaceutically acceptable salt thereof:

(I)

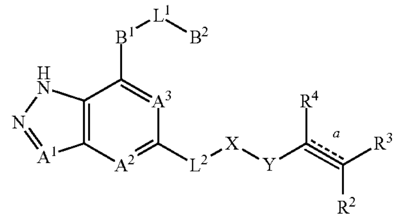

wherein:

$A^1$, $A^2$ and $A^3$ are each independently selected from the group consisting of $CR^1$ or N;

$B^1$ is independently selected from the group consisting of $C_{3-8}$ cyclic, 3- to 8-membered heterocyclic group, aryl, or heteroaryl, wherein cyclic group, heterocyclic group, aryl or heteroaryl is optionally substituted with one or more $G^1$;

$B^2$ is independently selected from the group consisting of H, $C_{3-8}$ cyclic group, 3- to 8-membered heterocyclic group, aryl, or heteroaryl, wherein cyclic group, heterocyclic group, aryl or heteroaryl is optionally substituted with one or more $G^2$;

$L^1$ is independently selected from the group consisting of $—C_{0-2}$ alkyl-, $—CR^5R^6—$, $—C_{1-2}$ alkyl$(R^5)(OH)—$, $—C(O)—$, $—CR^5R^6O—$, $—OCR^5R^6—$, $—SCR^5R^6—$, $—CR^5R^6S—$, $—NR^5—$, $—NR^5C(O)—$, $—C(O)NR^5—$, $—NR^5CONR^6—$, $—CF_2—$, $—O—$, $—S—$, $—S(O)_m—$, $—NR^5S(O)_2—$ or $—S(O)_2NR^5—$;

$L^2$ is independently selected from the group consisting of $—C_{0-4}$ alkyl-, $—C(O)—$, $—O—$, $—NR^7—$, $—NR^7C(O)—$ or $—NR^7S(O)_2—$;

X is independently selected from the group consisting of $C_{0-4}$ alkyl, $C_{3-8}$ cyclic group, 3- to 8-membered heterocyclic group, aryl, or heteroaryl, wherein alkyl, cyclic group, heterocyclic group, aryl or heteroaryl is optionally substituted with one or more $G^3$;

Y is independently selected from the group consisting of —C(O)—, —$NR^8C(O)$—, —$S(O)_m$— or —$NR^8S(O)_m$—;

$R^1$ is independently selected from the group consisting of H, D, $C_{0-4}$ alkyl, halogen or cyano;

bond ≋ is a double bond or a triple bond;

when bond ≋ is a double bond, $R^2$, $R^3$ and $R^4$ are each independently selected from the group consisting of H, D, cyano, halogen, alkyl, cyclic group, heterocyclic group, aryl, or heteroaryl, wherein alkyl, cyclic group, heterocyclic group, aryl or heteroaryl is optionally substituted with one or more $G^4$; when bond ≋ is a triple bond, $R^3$ and $R^4$ are absent, and $R^2$ is independently selected from the group consisting of H, D, cyano, halogen, alkyl, cyclic group, heterocyclic group, aryl, or heteroaryl, wherein alkyl, cyclic group, heterocyclic group, aryl or heteroaryl is optionally substituted with one or more $G^4$; wherein $R^3$ and $R^2$ or $R^3$ and $R^4$, together with the carbon atom attached thereto, can form a ring which contains optionally heteroatom(s);

$R^5$, $R^6$, $R^7$ and $R^8$ are each independently selected from the group consisting of H, D, $C_{0-8}$ alkyl, $C_{3-8}$ cyclic group, 3- to 8-membered heterocyclic group, aryl, or heteroaryl, wherein alkyl, cyclic group, heterocyclic group, aryl or heteroaryl is optionally substituted with one or more $G^5$;

$G^1$, $G^2$, $G^3$, $G^4$ and $G^5$ are each independently selected from the group consisting of H, D, halogen, cyano, alkyl, alkenyl, alkynyl, cyclic group, heterocyclic group, aryl, heteroaryl, —$OR^9$, —$OC(O)NR^9R^{10}$, —$C(O)OR^{10}$, —$C(O)NR^9R^{10}$, —$C(O)R^9$, —$NR^9R^{10}$, —$NR^9C(O)R^{10}$, —$NR^9C(O)NR^{10}R^{11}$, —$S(O)_mR^{10}$ and —$NR^9S(O)_mR^{10}$, wherein alkyl, alkenyl, alkynyl, cyclic group, heterocyclic group, aryl or heteroaryl is optionally substituted with one or more substituents selected from the group consisting of D, halogen, cyano, $C_{1-8}$ alkyl, $C_{3-8}$ cycloalkyl, 3- to 8-membered heterocyclic group, —$OR^{12}$, —$OC(O)NR^{12}R^{13}$, —$C(O)OR^{12}$, —$C(O)NR^{12}R^{13}$, —$C(O)R^{12}$, —$NR^{12}R^{13}$, —$NR^{12}C(O)R^{13}$, —$NR^{12}C(O)NR^{13}R^{14}$, —$S(O)_mR^{12}$, or —$NR^{12}S(O)_mR^{13}$;

$R^9$, $R^{10}$, $R^1$, $R^{12}$, $R^{13}$ and $R^{14}$ are each independently selected from the group consisting of H, $C_{1-6}$ alkyl, $C_1$-$C_6$ heteroalkyl, $C_{3-8}$ cycloalkyl, 3- to 8-membered monocyclic heterocyclic group, monocyclic heteroaryl or monocyclic aryl; and m is 1 or 2.

In an embodiment of the present invention, a compound represented by formula (I) or its tautomers, mesomers, racemates, enantiomers, diastereoisomers, mixtures thereof and a pharmaceutically acceptable salt thereof is a compound represented by formula (II), or its tautomers, mesomers, racemates, enantiomers, diastereoisomers, mixtures thereof and a pharmaceutically acceptable salt thereof:

(II)

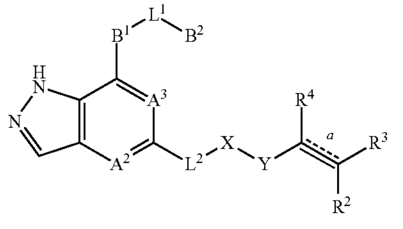

wherein:

$A^2$ and $A^3$ are each independently selected from the group consisting of CH or N;

$B^1$ is independently selected from the group consisting of $C_{3-8}$ cyclic group, 3- to 8-membered heterocyclic group, aryl, or heteroaryl, wherein cyclic group, heterocyclic group, aryl or heteroaryl is optionally substituted with one or more $G^1$;

$B^2$ is independently selected from the group consisting of H, $C_{3-8}$ cyclic group, 3- to 8-membered heterocyclic group, aryl, or heteroaryl, wherein cyclic group, heterocyclic group, aryl or heteroaryl is optionally substituted with one or more $G^2$;

$L^1$ is independently selected from the group consisting of —$C_{0-2}$ alkyl-, —$CR^5R^6$—, —$C_{1-2}$ alkyl($R^5$)(OH)—, —C(O)—, —$CR^5R^6O$—, —$OCR^5R^6$—, —$SCR^5R^6$—, —$CR^5R^6S$—, —$NR^5$—, —$NR^5C(O)$—, —$C(O)NR^5$—, —$NR^5CONR^6$—, —$CF_2$—, —O—, —S—, —$S(O)_2$—, —$NR^5S(O)_2$— or —$S(O)_2NR^5$—;

$L^2$ is independently selected from the group consisting of —$C_{0-4}$ alkyl-, —C(O)—, —O—, —$NR^7$—, —$NR^7C(O)$— or —$NR^7S(O)_2$—;

X is independently selected from the group consisting of $C_{0-4}$ alkyl, $C_{3-8}$ cyclic group, 3- to 8-membered heterocyclic group, aryl, or heteroaryl, wherein alkyl, cyclic group, heterocyclic group, aryl or heteroaryl is optionally substituted with one or more $G^3$;

Y is independently selected from the group consisting of —C(O)—, —$NR^8C(O)$—, —$S(O)_m$— or —$NR^8S(O)_m$—;

bond ≋ is a double bond or a triple bond;

when bond ≋ is a double bond, $R^2$, $R^3$ and $R^4$ are each other independently selected from the group consisting of H, D, cyano, halogen, alkyl, cyclic group, heterocyclic group, aryl or heteroaryl, wherein alkyl, cyclic group, heterocyclic group, aryl or heteroaryl is optionally substituted with one or more $G^4$; and when bond ≋ is a triple bond, $R^3$ and $R^4$ are absent, and $R^2$ is independently selected from the group consisting of H, D, cyano, halogen, alkyl, cyclic group, heterocyclic group, aryl, or heteroaryl, wherein alkyl, cyclic group, heterocyclic group, aryl or heteroaryl is optionally substituted with one or more $G^4$; wherein $R^3$ and $R^2$ or $R^3$ and $R^4$, together with the carbon atom attached thereto, can form a ring which contains optionally heteroatom(s);

$R^5$, $R^6$, $R^7$ and $R^8$ are each independently selected from the group consisting of H, D, $C_{0-8}$ alkyl, $C_{3-8}$ cyclic group, 3- to 8-membered heterocyclic group, aryl, or heteroaryl, wherein alkyl, cyclic group, heterocyclic group, aryl or heteroaryl is optionally substituted with one or more $G^5$;

$G^1$, $G^2$, $G^3$, $G^4$ and $G^5$ are each independently selected from the group consisting of H, D, halogen, cyano, alkyl, alkenyl, alkynyl, cyclic group, heterocyclic group, aryl, heteroaryl, —$OR^9$, —$OC(O)NR^9R^{10}$, —$C(O)OR^{10}$, —$C(O)NR^9R^{10}$, —$C(O)R^9$, —$NR^9R^{10}$, —$NR^9C(O)R^{10}$, —$NR^9C(O)NR^{10}R^{11}$, —$S(O)_mR^{10}$ and —$NR^9S(O)_mR^{10}$, wherein alkyl, alkenyl, alkynyl, cyclic group, heterocyclic group, aryl or heteroaryl is optionally substituted with one or more substituents selected from the group consisting of D, halogen, cyano, $C_{1-8}$ alkyl, $C_{3-8}$ cycloalkyl, 3- to 8-membered heterocyclic group, —$OR^{12}$, —$OC(O)NR^{12}R^{13}$, —$C(O)OR^{12}$, —$C(O)NR^{12}R^{13}$, —$C(O)R^{12}$, —$NR^{12}R^{13}$, —$NR^{12}C(O)R^{13}$, —$NR^{12}C(O)NR^{13}R^{14}$, —$S(O)_mR^{12}$, or —$NR^{12}S(O)_mR^{13}$;

$R^9$, $R^{10}$, $R^{11}$, $R^{12}$, $R^{13}$ and $R^{14}$ are each independently selected from the group consisting of H, $C_{1-6}$ alkyl, $C_1$-$C_6$ heteroalkyl, $C_{3-8}$ cycloalkyl, 3- to 8-membered monocyclic heterocyclic group, monocyclic heteroaryl or monocyclic aryl; and m is 1 or 2.

In another embodiment of the present invention, a compound represented by formula (I) or its tautomers, mesomers, racemates, enantiomers, diastereoisomers, mixtures thereof and a pharmaceutically acceptable salt thereof is a compound represented by formula (III), or its tautomers, mesomers, racemates, enantiomers, diastereoisomers, mixtures thereof and a pharmaceutically acceptable salt thereof:

(III)

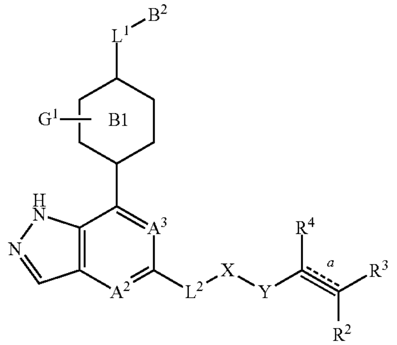

wherein:

$B^1$ is a phenyl ring or a 6-membered heteroaryl ring;

$A^2$, $A^3$, $B^2$, $L^1$, $L^2$, X, Y, bond $\equiv$, $R^2$, $R^3$, $R^4$ and $G^1$ are as defined in claim 1 or 2.

In another embodiment of the present invention, a compound represented by formula (I) or its tautomers, mesomers, racemates, enantiomers, diastereoisomers, mixtures thereof and a pharmaceutically acceptable salt thereof is a compound represented by formula (IV), or its tautomers, mesomers, racemates, enantiomers, diastereoisomers, mixtures thereof and a pharmaceutically acceptable salt thereof:

(IV)

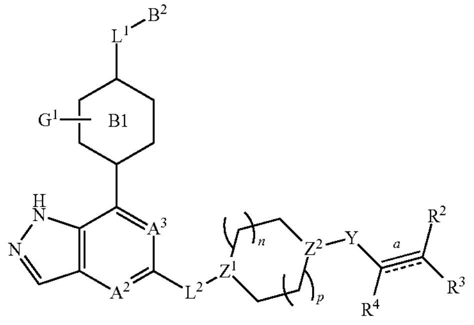

wherein:

$Z^1$ and $Z^2$ are each independently selected from the group consisting of $C(R^a)$, or N;

$R^a$ is H or alkyl;

n and p are each independently selected from the group consisting of 0, 1 or 2;

$A^2$, $A^3$, $B^1$, $B^2$, $L^1$, $L^2$, Y, bond $\equiv$, $R^2$, $R^3$, $R^4$ and $G^1$ are as defined in any one of claims 1-3.

In another embodiment of the present invention, a compound represented by formula (I) or its tautomers, mesomers, racemates, enantiomers, diastereoisomers, mixtures thereof and a pharmaceutically acceptable salt thereof is a compound represented by formula (V), or its tautomers, mesomers, racemates, enantiomers, diastereoisomers, mixtures thereof and a pharmaceutically acceptable salt thereof:

(V)

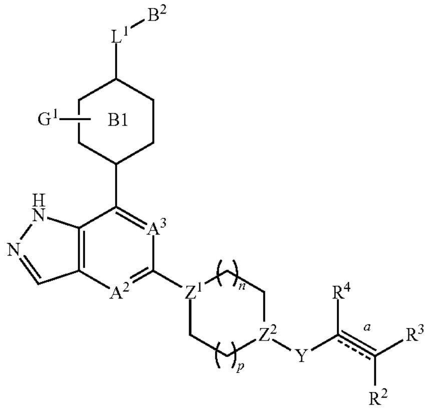

wherein:

$A^2$, $A^3$, $B^1$, $B^2$, $L^1$, Y, bond $\equiv$, $R^2$, $R^3$, $R^4$, $G^1$, $Z^1$, $Z^2$, n and p are as defined in any one of claims 1-4.

Representative compounds of the present invention include, but are not limited to:

| Compound No. | Compound Structure and Nomenclature |
|---|---|
| 1. | 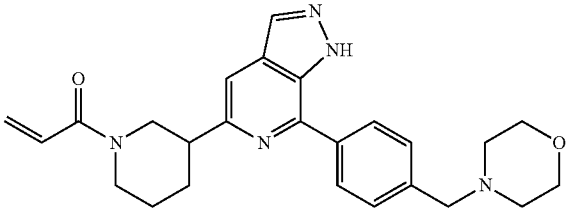 1-(3-(7-(4-(morpholinomethyl)phenyl)-1H-pyrazolo[3,4-c]pyridin-5-yl)piperidin-1-yl)prop-2-en-1-one |

-continued

| Compound No. | Compound Structure and Nomenclature |
|---|---|
| 2. | 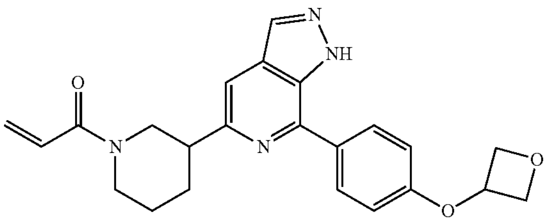 1-(3-(7-(4-(oxetan-3-oxy)phenyl)-1H-pyrazolo[3,4-c]pyridin-5-yl)piperidin-1-yl)prop-2-en-1-one |
| 3. | 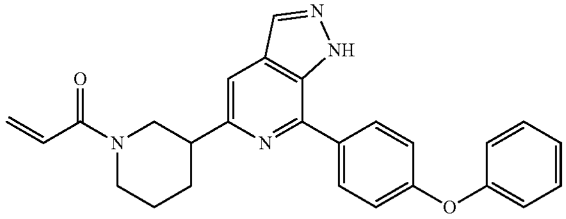 1-(3-(7-(4-phenoxyphenyl)-1H-pyrazolo[3,4-c]pyridin-5-yl)piperidin-1-yl)prop-2-en-1-one |
| 4. | 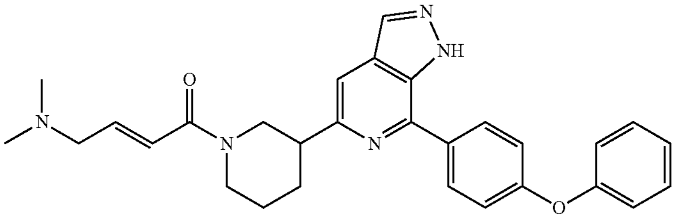 (E)-4-(dimethylamino)-1-(3-(7-(4-phenoxyphenyl)-1H-pyrazolo[3,4-c]pyridin-5-yl)piperidin-1-yl)but-2-en-1-one |
| 5. | 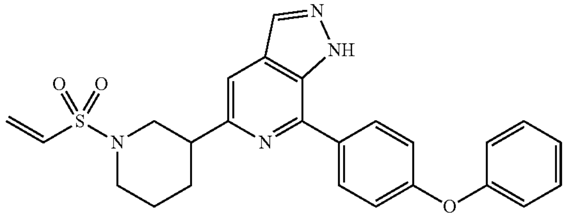 7-(4-phenoxyphenyl)-5-(1-(ethenylsulfonyl)piperidin-3-yl)-1H-pyrazolo[3,4-c]pyridine |
| 6. | 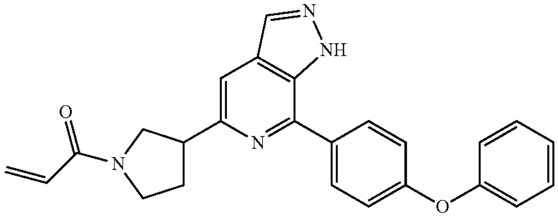 1-(3-(7-(4-phenoxyphenyl)-1H-pyrazolo[3,4-c]pyridin-5-yl)pyrrolidin-1-yl)prop-2-en-1-one |

-continued

| Compound No. | Compound Structure and Nomenclature |
| --- | --- |
| 7. | 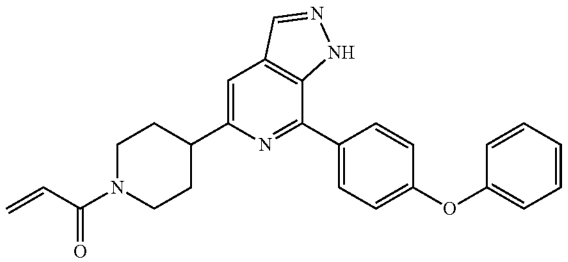 1-(4-(7-(4-phenoxyphenyl)-1H-pyrazolo[3,4-c]pyridin-5-yl)piperidin-1-yl)prop-2-en-1-one |
| 8. | 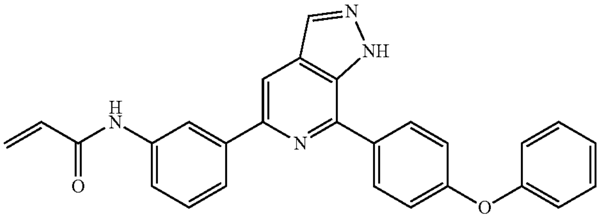 N-(3-(7-(4-phenoxyphenyl)-1H-pyrazolo[3,4-c]pyridin-5-yl)phenyl)acrylamide |
| 9. | 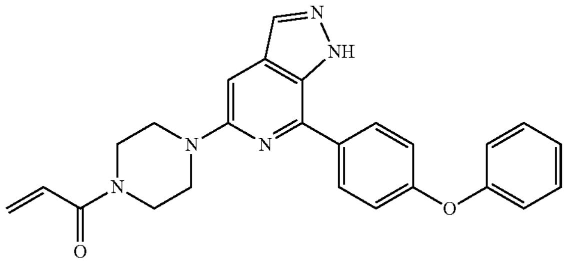 1-(4-(7-(4-phenoxyphenyl)-1H-pyrazolo[3,4-c]pyridin-5-yl)piperazin-1-yl)prop-2-en-1-one |
| 10. | 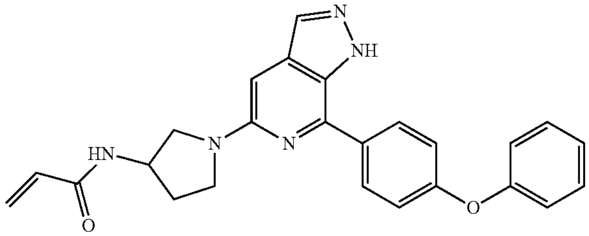 N-(1-(7-(4-phenoxyphenyl)-1H-pyrazolo[3,4-c]pyridin-5-yl)pyrrolidin-3-yl)acrylamide |
| 11. | 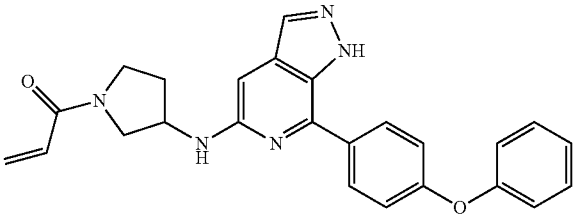 1-(3-((7-(4-phenoxyphenyl)-1H-pyrazolo[3,4-c]pyridin-5-yl)amino)pyrrolidin-1-yl)prop-2-en-1-one |

-continued
| Compound No. | Compound Structure and Nomenclature |
|---|---|
| 12. | 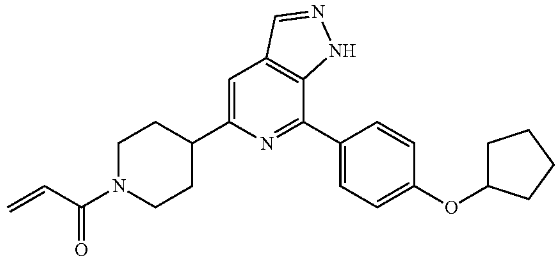 1-(4-(7-(4-(cyclopentyloxy)phenyl)-1H-pyrazolo[3,4-c]pyridin-5-yl)piperidin-1-yl)prop-2-en-1-one |
| 13. | 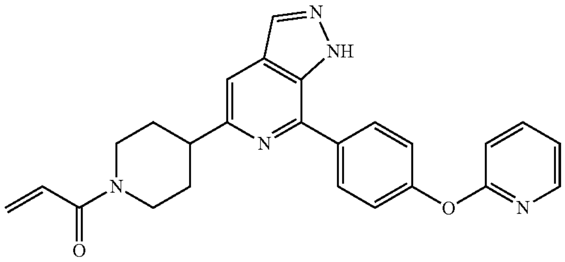 1-(4-(7-(4-(pyridin-2-oxy)phenyl)-1H-pyrazolo[3,4-c]pyridin-5-yl)piperidin-1-yl)prop-2-en-1-one |
| 14. | 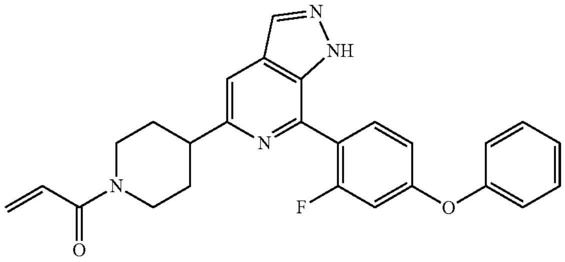 1-(4-(7-(2-fluoro-4-phenoxyphenyl)-1H-pyrazolo[3,4-c]pyridin-5-yl)piperidin-1-yl)prop-2-en-1-one |
| 15. | 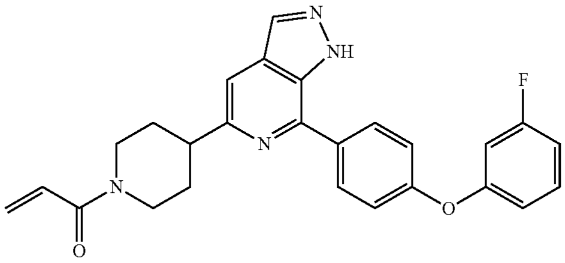 1-(4-(7-(4-(3-fluorophenoxy)phenyl)-1H-pyrazolo[3,4-c]pyridin-5-yl)piperidin-1-yl)prop-2-en-1-one |

-continued

| Compound No. | Compound Structure and Nomenclature |
|---|---|
| 16. | 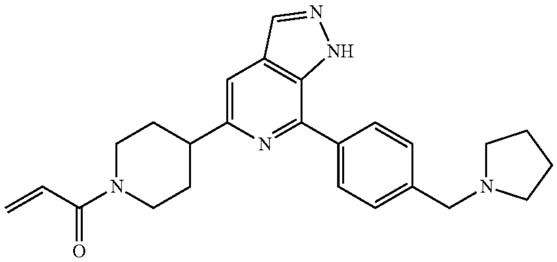 1-(4-(7-(4-(pyrrolidin-1-ylmethyl)phenyl)-1H-pyrazolo[3,4-c]pyridin-5-yl)piperidin-1-yl)prop-2-en-1-one |
| 17. | 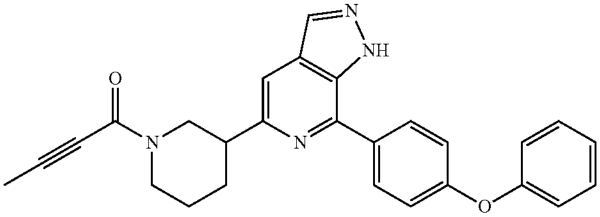 1-(3-(7-(4-phenoxyphenyl)-1H-pyrazolo[3,4-c]pyridin-5-yl)piperidin-1-yl)but-2-en-1-one |
| 18. | 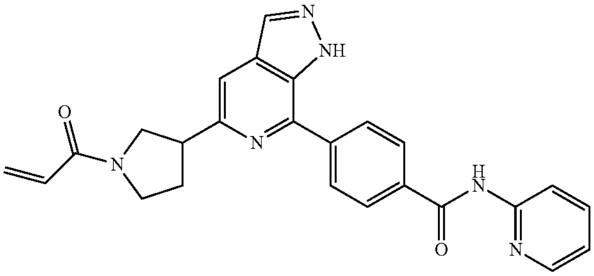 4-(5-(1-acryloylpyrrolidin-3-yl)-1H-pyrazolo[3,4-c]pyridin-7-yl)-N-(pyridin-2-yl)benzamide |
| 19. | 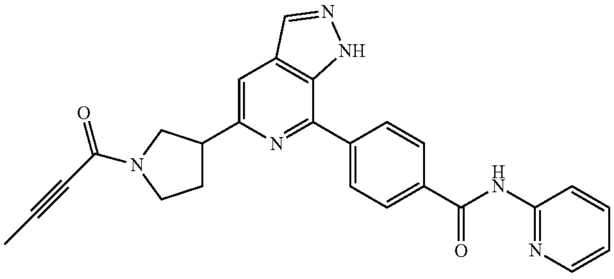 4-(5-(1-(but-2-ynoyl)pyrrolidin-3-yl)-1H-pyrazolo[3,4-c]pyridin-7-yl)-N-(pyridin-2-yl)benzamide |
| 20. | 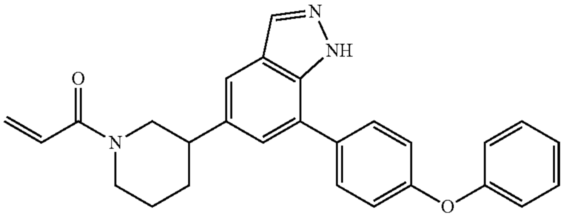 1-(3-(7-(4-phenoxyphenyl)-1H-indazol-5-yl)piperidin-1-yl)prop-2-en-1-one |

-continued

| Compound No. | Compound Structure and Nomenclature |
|---|---|
| 21. | 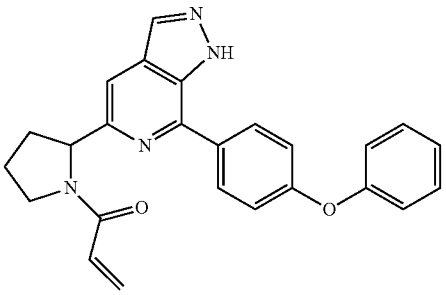<br>1-(2-(7-(4-phenoxyphenyl)-1H-pyrazolo[3,4-c] pyridin-5-yl)pyrrolidin-1-yl) |
| 22. | 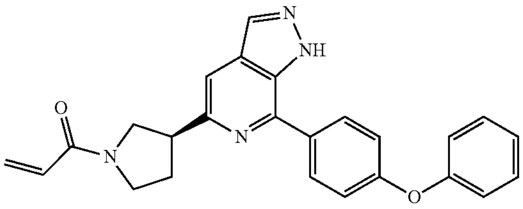 (22a) 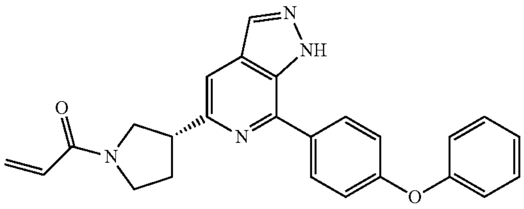 (22b)<br>(S)-1-(3-(7-(4-phenoxyphenyl)-1H-pyrazolo[3,4-c]pyridin-5-yl)pyrrolidin-1-yl)prop-2-en-1-one 22a and (R)-1-(3-(7-(4-phenoxyphenyl)-1H-pyrazolo[3,4-c]pyridin-5-yl)pyrrolidin-1-yl)prop-2-en-1-one 22b |

or their tautomers, mesomers, racemates, enantiomers, diastereoisomers, mixtures thereof and pharmaceutically acceptable salts thereof.

The present invention is further directed to a pharmaceutical composition comprising a therapeutically effective amount of a compound represented by formula (I) or its tautomers, mesomers, racemates, enantiomers, diastereoisomers, mixtures thereof and a pharmaceutically acceptable salt thereof, and a pharmaceutically acceptable carrier, diluent, or excipient.

Another aspect of the present invention relates to use of the compound represented by formula (I) or its tautomers, mesomers, racemates, enantiomers, diastereoisomers, mixtures thereof and a pharmaceutically acceptable salt thereof, or the pharmaceutical composition comprising the same in the preparation of Bruton tyrosine kinase inhibitors.

Another aspect of the present invention relates to use of the compound represented by formula (I) or its tautomers, mesomers, racemates, enantiomers, diastereoisomers, mixtures thereof and a pharmaceutically acceptable salt thereof, or the pharmaceutical composition comprising the same in the preparation of a medicament for treating and/or preventing tumors, inflammatory diseases, and the like.

The present invention also relates to a method of treating and/or preventing tumors, inflammatory diseases, and the like, comprising administering a therapeutically effective amount of a compound represented by formula (I) or its tautomers, mesomers, racemates, enantiomers, diastereoisomers, mixtures thereof and a pharmaceutically acceptable salt thereof, or a pharmaceutical composition comprising the same to a patient in need thereof.

Another aspect of the present invention relates to a compound represented by formula (I) or its tautomers, mesomers, racemates, enantiomers, diastereoisomers, mixtures thereof and a pharmaceutically acceptable salt thereof for use as a medicament for treating and/or preventing tumors, inflammatory diseases, and the like.

DETAILED DESCRIPTION

The terms as used in the description and claims have the following meanings, unless otherwise indicated.

The expression "$C_{x-y}$" as used herein means the range of carbon atoms, wherein both x and y are an integer. For Example, $C_{3-8}$ cyclic group means a cyclic group having 3-8 carbon atoms, and —$C_{0-2}$ alkyl means an alkyl group having 0-2 carbon atoms, wherein —$C_0$ alkyl refers to a single chemical bond.

"Alkyl" refers to a saturated aliphatic hydrocarbon group, including straight and branched groups having 1-20 carbon atoms, e.g., straight or branched groups having 1-18 carbon atoms, 1-12 carbon atoms, 1-8 carbon atoms, 1-6 carbon atoms, or 1-4 carbon atoms. Non-limiting examples include methyl, ethyl, n-propyl, iso-propyl, n-butyl, iso-butyl, tert-butyl, sec-butyl, n-pentyl, 1,1-dimethyl-propyl, 1,2-dimethyl-propyl, 2,2-dimethyl-propyl, 1-ethyl-propyl, 2-methyl-butyl, 3-methyl-butyl, n-hexyl, 1-ethyl-2-methyl-propyl, 1,1,2-trimethyl-propyl, 1,1-dimethyl-butyl, 1,2-dimethyl-butyl, 2,2-dimethyl-butyl, 1,3-dimethyl-butyl, 2-ethyl-butyl, and any branched isomer thereof, etc. Alkyl can be optionally substituted or unsubstituted.

"Cyclic group" refers to saturated or partially unsaturated, mono-cyclic or multi-cyclic hydrocarbon substituents containing 3-12 ring atoms, such as, 3-12, 3-10, or 3-6 ring atoms, or the cyclic group can be a 3-, 4-, 5-, or 6-membered ring. Non-limiting examples of mono-cyclic groups comprise cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Cyclic group can be optionally substituted or unsubstituted.

"Heterocyclic group" refers to saturated or partially unsaturated, mono-cyclic or multi-cyclic hydrocarbon substituents containing 3-20 ring atoms, such as, 3-16, 3-12, 3-10, or 3-6 ring atoms, in which one or more ring atoms are heteroatom(s) selected from the group consisting of nitrogen, oxygen and $S(O)_m$ (wherein m is an integer from 0 to 2), excluding the case that any ring moiety is —O—O—, —O—S— or —S—S—, and the remainder ring atoms are carbon. Preferably, the heterocyclic group comprises 3-12 ring atoms, of which 1-4 ring atoms are heteroatoms; more preferably, the heterocycloalkyl ring contains 3-10 ring atoms; and most preferably, the heterocyclic group comprises a 5- or 6-membered ring, wherein 1-4 atoms are heteroatoms, more preferably 1-3 atoms are heteroatoms, and most preferably 1-2 atoms are heteroatoms. Non-limiting examples of mono-cyclic heterocyclic group comprise pyrrolidinyl, piperidyl, piperazinyl, morpholinyl, sulfomorpholinyl, homopiperazinyl and the like. Multi-cyclic heterocyclic groups comprise those comprising spiro-ring, fused-ring, and bridged ring.

"Spiro-heterocyclic group" refers to a 5- to 20-membered, multi-cyclic heterocyclic group wherein a plurality of mono-cyclic rings shares a common atom (namely, a spiro atom), and wherein one or more ring atoms are heteroatom(s) selected from the group consisting of nitrogen, oxygen, and $S(O)_m$ (wherein m is an integer from 0 to 2), and the remainder ring atoms are carbon. The monocyclic rings can contain one or more double bonds, but none of the mono-cyclic rings has a completely conjugated π-electron system. It is preferably a 6- to 14-membered ring, and more preferably 7- to 10-membered ring. Depending on the number of common spiro-atoms, the spirocycloalkyl groups are classified as mono-spiro heterocyclic groups, bis-spiro heterocyclic groups, or multi-spiro heterocyclic groups, with mono-spirocycloalkyl and bis-spirocycloalkyl preferred. More preferred are 4-/4-membered, 4-/5-membered, 4-/6-membered, 5-/5-membered, or 5-membered/6-membered mono-spiro cycloalkyl groups. Non-limiting examples of spirocycloalkyl groups comprise:

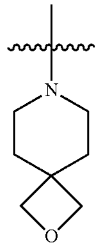
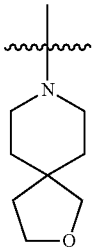
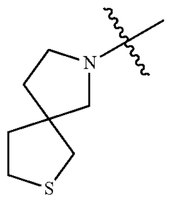
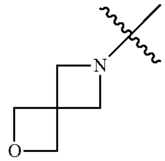
and
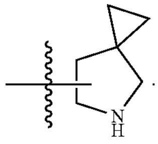
.

"Fused-heterocyclic group" refers to a 5- to 20-membered multi-cyclic heterocyclic group wherein each ring in the system comprises a pair of adjacent atoms shared with other rings in the system, wherein one or more rings can contain one or more double bonds, but none of the rings comprises a completely conjugated π-electron subsystem, and wherein one or more ring atoms are heteroatom(s) selected from the group consisting of nitrogen, oxygen, and $S(O)_m$ (wherein m is an integer from 0 to 2), and the remainder ring atoms are carbon. It is preferably a 7- to 14-membered ring, and more preferably 7- to 10-membered ring. Depending on the number of the rings, the fused heterocyclic groups are classified as bicyclic, tricyclic, tetracyclic, or polycyclic fused heterocycloalkyl groups, with bicyclic or tricyclic fused heterocyclic groups preferred. More preferred are 5-/5-membered and 5-/6-membered bicyclic fused heterocyclic groups. Non-limiting examples of fused heterocyclic groups comprise:

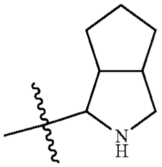
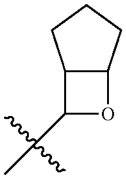
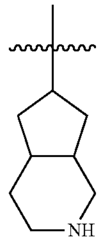
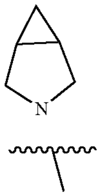
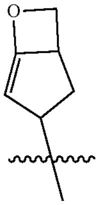
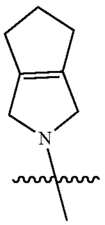
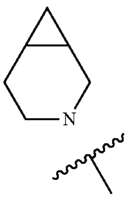
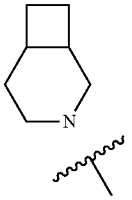
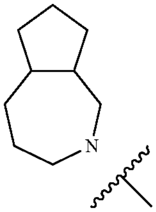
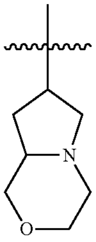
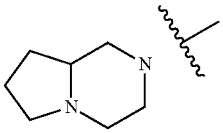
and
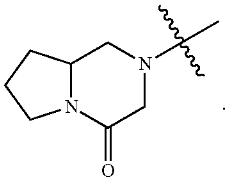
.

The heterocyclic ring can be fused to an aryl, a heteroaryl or a cycloalkyl ring, wherein the ring attached to the parent structure is a heterocyclic ring. Non-limiting examples thereof comprise:

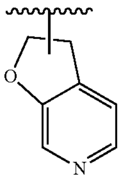
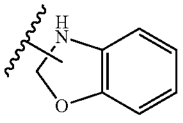

-continued

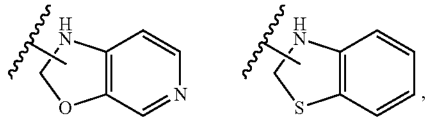

and the like. The heterocyclic group can be optionally substituted or unsubstituted.

"Aryl" refers to a 6- to 14-membered full carbon monocyclic or a fused-polycyclic (i.e., rings sharing a pair of adjacent carbon atoms) group, a polycyclic group (i.e., rings having a pair of adjacent carbon atoms) having conjugated π electron system. It is preferably a 6- to 10-membered aryl, such as, phenyl and naphthyl, and most preferably phenyl. The aryl ring can be fused to a heteroaryl, a heterocyclic or a cycloalkyl ring, wherein the ring attached to the parent structure is an aryl ring. Non-limiting examples thereof comprise:

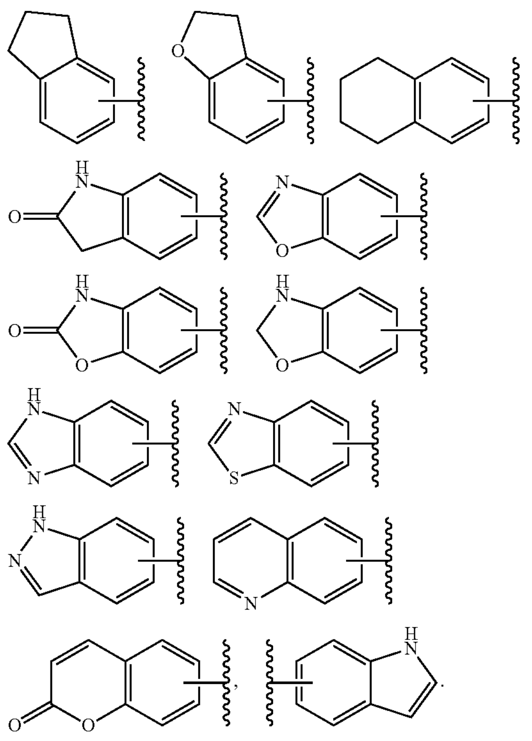

Aryl can be optionally substituted or unsubstituted.

"Heteroaryl" refers to a heteroaromatic system having 1 to 4 heteroatoms and 5 to 14 ring atoms, wherein the heteroatoms comprise oxygen, sulfur and nitrogen. It is preferably a 5- to 10-membered heteroaryl. More preferably, the heteroaryl is a 5- or 6-membered heteroaryl, such as, furyl, thienyl, pyridyl, pyrrolyl, N-alkylpyrrolyl, pyrimidyl, pyrazinyl, imidazolyl, tetrazolyl, oxazolyl, isoxazolyl, and the like. The heteroaryl ring can be fused to an aryl, a heterocyclic or a cycloalkyl ring, wherein the ring attached to the parent structure is a heteroaryl ring. Non-limiting examples thereof comprise:

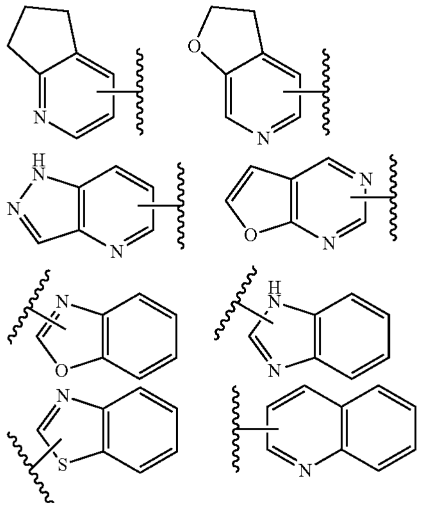

and

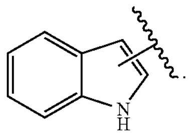

Heteroaryl can be optionally substituted or unsubstituted.

"Halogen" refers to fluorine, chlorine, bromine, or iodine.

"Cyano" refers to —CN.

"Optional" or "optionally" means that the event or environment with reference to such term(s) may (but not necessarily) occur, including the situations that such event or environment occurs or does not occur. For example, "a heterocyclic group optionally substituted with an alkyl group" means that the alkyl group may be but not necessarily present, including the situations that the heterocyclic group is substituted with the alkyl and that the heterocyclic group is not substituted with the alkyl.

"Substituted" means that one or more hydrogen atoms, preferably up to 5 hydrogen atoms, and more preferably 1-3 hydrogen atoms in a group, are each independently substituted with the corresponding number of substituent(s). Apparently, the substituents are merely present in their possible positions, and persons skilled in the art can determine possible or impossible substitutions (by experiments or theory) without paying much effort. For example, the binding between an amino or hydroxyl group having free hydrogen and carbon atoms having unsaturated (e.g., olefinic) bond may be unstable.

"Pharmaceutical composition" refers to a mixture comprising one or more compounds as described herein or a physiologically/pharmaceutically acceptable salt or prodrug thereof and other chemical components, as well as other components such as, a physiologically/pharmaceutically acceptable carrier and excipient. The pharmaceutical composition aims to promote the administration to a living body and facilitate the absorption of active ingredients, thereby exerting the biological activity.

Synthetic Method

The present invention further provides a method of preparing the compounds. The compound represented by formula (I) of the present invention can be prepared in according with the following exemplary methods and examples, which should not however be construed as limiting the scope of the present invention in any manner. The inventive compounds can also be synthesized by any synthetic technique that is well known by persons skilled in the art, or by a combination of the known methods with the methods of the present invention. The product produced in each step can be obtained by any known separation techniques in the art, comprising but not limited to extraction, filtration, distillation, crystallization, chromatography and so on. Starting materials and chemical agents as required by synthesis may be routinely prepared according to literatures (available from SciFinder) or commercially available.

The fused pyrazole compounds represented by formula (I) of the present invention can be prepared according to Scheme A: 1) reacting a starting material A1 reacted with a precursor bearing boric acid or borate $(RO)_2B$-L~N-P (wherein L~N-P is a functional group having a protected amino, and P is a protecting group of the amino) via Suzuki coupling reaction to produce A2, or with a precursor bearing an amino L~N-P (wherein L comprises —NH) via Buchwald coupling reaction to produce A2; 2) brominating A2 to produce A3; 3) reacting A3 with a (hetero)aryl boric acid or borate via Suzuki coupling to produce A4; 4) acetylating the amino group in A4 to produce A5; 5) further cyclizing A5 to produce A6; 6) deprotecting the amino group in A6 to produce A7; and 7) derivating the amino group in A7 with a chemical agent containing a functional group capable of reacting with cysteine residue(s) in the binding domain of a kinase ligand (e.g., acryloyl chloride etc.), to produce a target compound A8.

Scheme A:

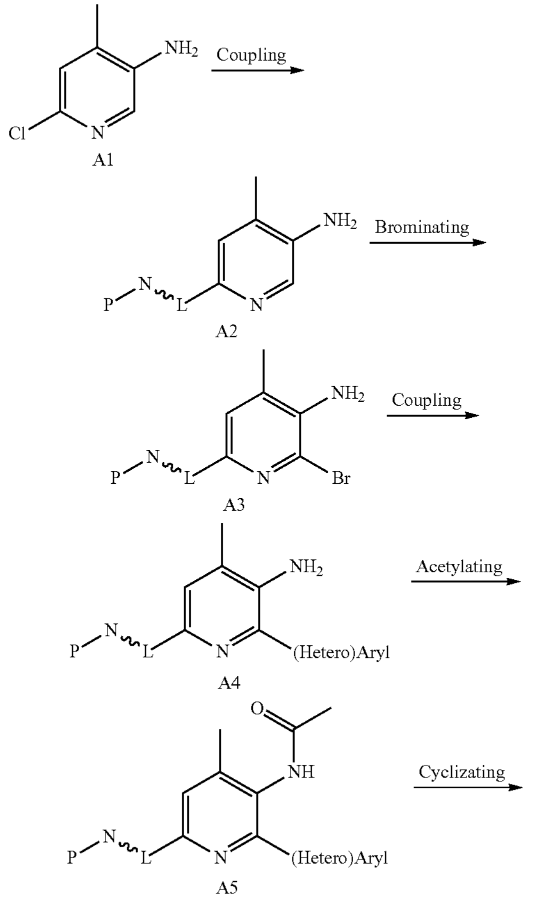

-continued

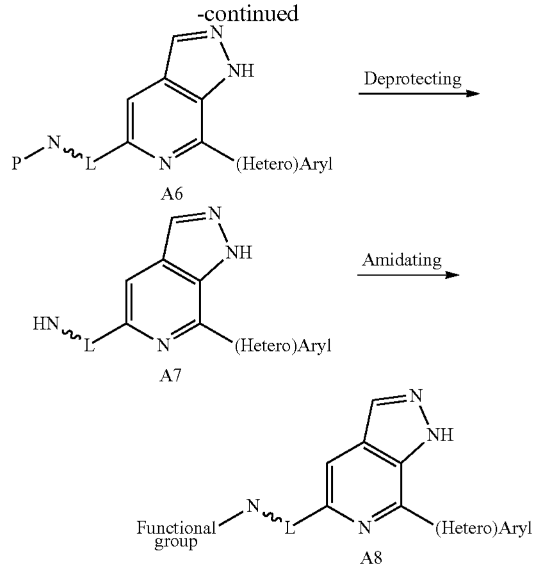

A6 can also be prepared according to Scheme B: subjecting B2 to undergo Buchwald coupling reaction to produce B3, followed by acetylation, cyclization, and coupling to produce an intermediate A6.

Scheme B:

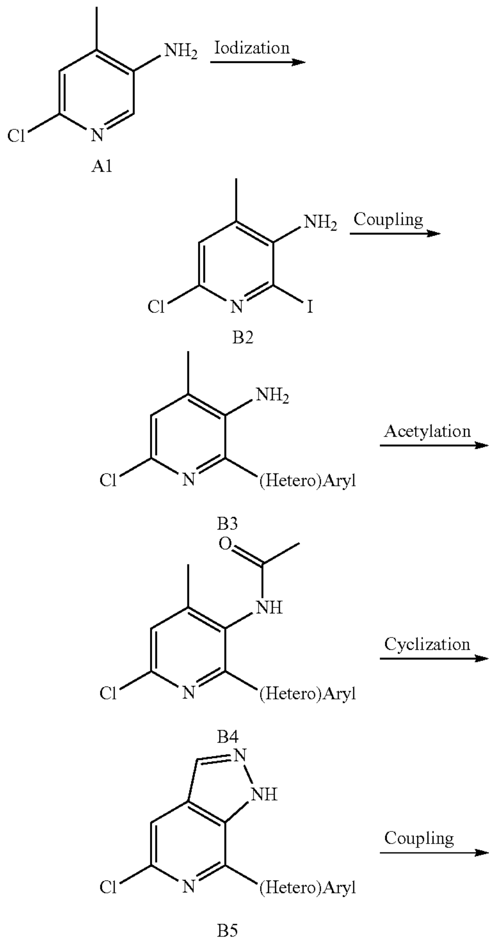

-continued

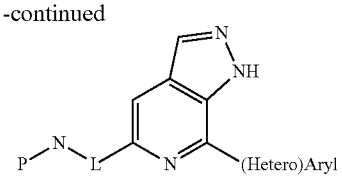

A6

A6 can also be prepared according to Scheme C: subjecting C1 or C1' to iodization or bromination, followed by cyclization to produce C3. In accordance with the requirements of synthesis, an iodine-containing C3 is subject to a coupling reaction with a (hetero)aryl boric acid (or borate) via Suzuki coupling, following by a second coupling reaction with $((RO)_2B\text{-})L\sim N\text{-}P$, to produce A6; or a bromine-containing C3 is subject to a first coupling reaction with $((RO)_2B\text{-})L\sim N\text{-}P$, followed by a second coupling reaction with a (hetero)aryl boric acid (or borate), to produce A6.

Scheme C:

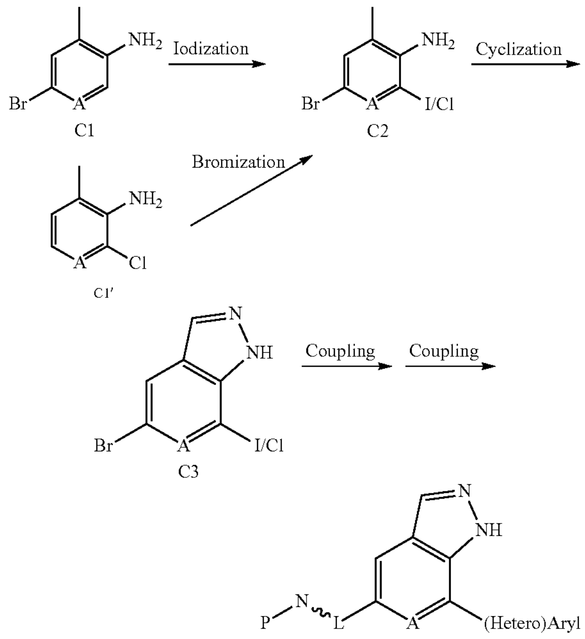

A6

EXAMPLES

The compound of formula (I) or a pharmaceutically acceptable salt thereof can be prepared by the exemplary methods as described in the following examples and the associated publications referenced by persons skilled in the art. However, these examples are not to limit the scope of the present invention.

The structure of compounds are identified by nuclear magnetic resonance (NMR) or mass spectrum (MS). NMR measurements are conducted on a Bruker AVANCE-400 or Varian Oxford-300 NMR instrument, using DMSO-$d_6$, $CDCl_3$, $CD_3OD$ as solvent, tetramethylsilane (TMS) as an internal standard, and a chemical shift of $10^{-6}$ ppm.

MS measurements are conducted on an Agilent SQD (ESI) mass spectrometer (manufacturer: Agilent, Model: 62100) or a Shimadzu SQD (ESI) mass spectrometer (manufacturer: Shimadzu, Model: 2020).

HPLC measurements are conducted on an Agilent 1200 DAD high pressure liquid chromatograph (Sunfire C18, 150×4.6 mm, 5 μm chromatographic column), and Waters 2695-2996 high pressure liquid chromatograph (Gimini C18 150×4.6 mm, 5 μm chromatographic column).

The used silica gel plate is Qingdao Haiyang GF254 silica gel plate. The silica gel plate has a specification of 0.15 mm-0.2 mm when used in the thin layer chromatography (TLC), and a specification of 0.4 mm-0.5 mm during the separation and purification of product by thin layer chromatography.

Column chromatography usually employs Qingdao Haiyang 200-300 mesh silica gel as carrier.

The known starting materials of the present invention can be prepared by or in accordance with the methods known in the art, or commercially available from ABCR GmbH&Co. KG, Acros Organics, Aldrich Chemical Company, Accela ChemBio, Beijing Ouhe Chemical Company, and so on.

The reactions in the examples are carried out under an argon or nitrogen atmosphere unless otherwise indicated.

Argon or nitrogen atmosphere means that the reaction flask is connected to an argon or nitrogen balloon having a 1 L volume.

Hydrogen atmosphere means that the reaction flask is connected to a hydrogen balloon having a 1 L volume.

Pressurized hydrogenation reaction is carried out by using a GCD-500G high-purity hydrogen generator and BLT-2000 medium-pressure hydrogenation instrument available from Beijing Jiawei Kechuang Technology Co., Ltd.

Hydrogenation reaction is usually carried out by vacuuming the reactor and charging it with hydrogen, and the aforesaid steps are repeated three times.

Microwave reaction is conducted on a CEM Discover-SP-type microwave reactor.

The reaction temperature in the examples is room temperature ranging from 20° C. to 30° C. unless otherwise indicated.

The reaction progress in the examples is monitored with thin layer chromatography (TLC). The developer system used in the reaction comprises: A: dichloromethane and methanol system; and B: petroleum ether and ethyl acetate system, wherein the volumetric ratio of solvents is adjusted in accordance with the polarity of compounds.

The eluent system in column chromatography and the developer system in thin layer chromatography for use in the purification of compounds comprise: A: dichloromethane and methanol system; and B: petroleum ether and ethyl acetate system, wherein the volumetric ratio of solvents is adjusted in accordance with the polarity of compounds, and a small amount of triethylamine and an acidic or alkaline reagent may be added for adjustment.

Example 1

1-(3-(7-(4-(morpholinomethyl)phenyl)-1H-pyrazolo[3,4-c]pyridin-5-yl)piperidin-1-yl)prop-2-en-1-one

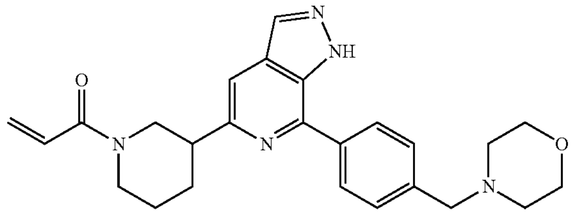

1

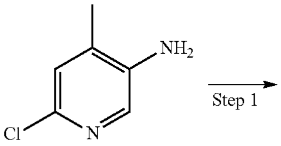

1a

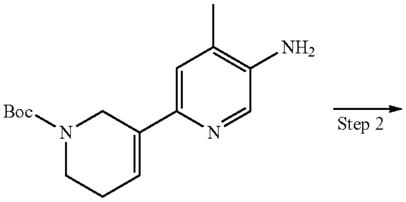

1b

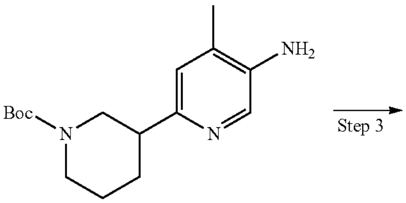

1c

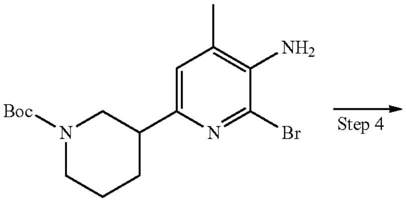

1d

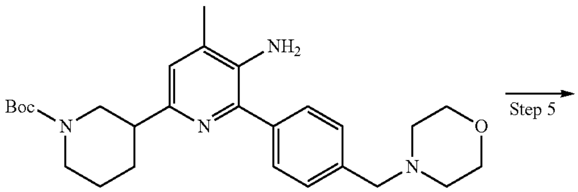

1e

-continued

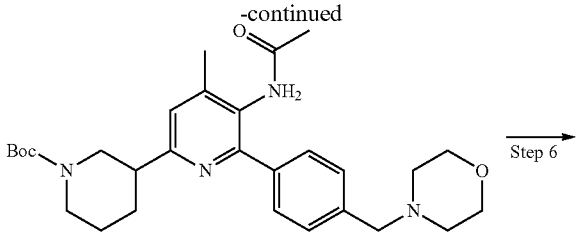

1f

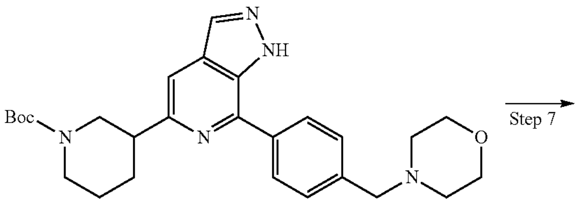

1g

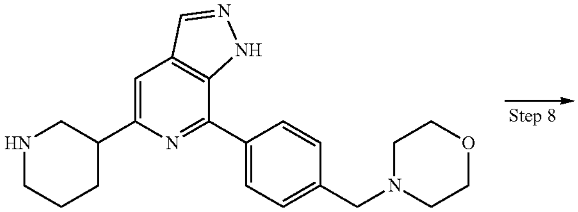

1h

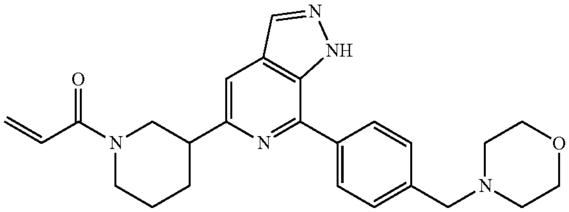

1

Step 1

Tert-butyl 5-amino-4-methyl-5',6'-dihydro-[2,3'-dipyridyl]-1'(2'H)-carboxylate

Compound 6-chloro-4-methylpyridin-3-amine 1a (568 mg, 4.0 mmol), tert-butyl 3-(4,4,5,5-tetramethyl-1,3,2-dioxaborolan-2-yl)-5,6-dihydropyridine-1(2H)-carboxylate (1.22 g, 4.0 mmol), cesium carbonate (3.8 g, 12 mmol), [1,1'-bis(diphenylphosphine)ferrocene]palladium dichloride dichloromethane adduct (146 mg, 0.2 mmol), 1,4-dioxane (30 mL), and water (7 mL) were mixed, degassed, and heated to reflux under nitrogen for 16 hrs. The mixture was cooled to room temperature and concentrated to remove solvent under reduced pressure. The residue was purified by column chromatography on silica gel (petroleum ether/ethyl acetate=20/1 to 2/1) to produce the target compound tert-butyl 5-amino-4-methyl-5',6'-dihydro-[2,3'-dipyridyl]-1'(2'H)-carboxylate 1b (401 mg, yellow oil), yield: 34%.

MS m/z (ESI):290[M+1]

Step 2

Tert-butyl 3-(5-amino-4-methylpyridin-2-yl)piperidin-1-carboxylate

Compound tert-butyl 5-amino-4-methyl-5',6'-dihydro-[2,3'-dipyridyl]-1'(2'H)-carboxylate 1b (401 mg, 0.45 mmol), Pd/C (106 mg), and ethanol (100 mL) were mixed, degassed, and stirred under hydrogen atmosphere at room temperature for 16 hrs. The mixture was filtered and concentrated to remove solvent under reduced pressure to give the crude target product tert-butyl 3-(5-amino-4-methylpyridin-2-yl) piperidin-1-carboxylate 1c (400 mg, yellow oil) which was used for the next reaction without further purification.

MS m/z (ESI):292[M+1]

Step 3

Tert-butyl 3-(5-amino-6-bromo-4-methylpyridin-2-yl)piperidin-1-carboxylate

Compound tert-butyl 3-(5-amino-4-methylpyridin-2-yl) piperidin-1-carboxylate 1c (400 mg, crude), N-bromosuccinimide (244 mg, 1.4 mmol), and dichloromethane (5 mL) were mixed at 0° C., and then stirred at 0° C. for 1 hr. Saturated sodium bicarbonate (10 mL) was added and the mixture was extracted with dichloromethane (20 mL×3). The organic phases were combined, dried over anhydrous sodium sulfate, filtered to remove the desiccant, and concentrated to remove solvent under reduced pressure. The residue was purified by column chromatography on silica gel (petroleum ether/ethyl acetate=6/1) to give a target product tert-butyl 3-(5-amino-6-bromo-4-methylpyridin-2-yl)piperidin-1-carboxylate 1d (290 mg, brown oil), yield: two-step 57%.

MS m/z (ESI):370[M+1]

Step 4

Tert-butyl 3-(5-amino-4-methyl-6-(4-(morpholinomethyl)phenyl)pyridin-2-yl)piperidin-1-carboxylate Compound tert-butyl 3-(5-amino-6-bromo-4-methylpyridin-2-yl)piperidin-1-carboxylate 1d (300 mg, 0.81 mmol), 4-(4-(4,4,5,5-tetramethyl-1,3,2-dioxaborolan-2-yl)phenmethyl)morpholine (295 mg, 0.97 mmol), cesium carbonate (792 mg, 2.4 mmol), [1,1'-bis(diphenylphosphine)ferrocene] palladium dichloride dichloromethane adduct (50 mg, 0.2 mmol), 1,4-dioxane (15 mL), and water (5 mL) were mixed, degassed, and heated to reflux under nitrogen for 16 hrs. The mixture was cooled to room temperature and concentrated to remove solvent under reduced pressure. The residue was purified by column chromatography on silica gel (petroleum ether/ethyl acetate=20/1 to 1/1) to produce a target compound tert-butyl 3-(5-amino-4-methyl-6-(4-(morpholinomethyl)phenyl)pyridin-2-yl)piperidin-1-carboxylate 1e (300 mg, yellow oil), yield: 80%.

MS m/z (ESI):467[M+1]

Step 5

Tert-butyl 3-(5-acetamido-4-methyl-6-(4-(morpholinomethyl)phenyl)pyridin-2-yl)piperidin-1-carboxylate Compound tert-butyl 3-(5-amino-4-methyl-6-(4-(morpholinomethyl)phenyl)pyridin-2-yl)piperidin-1-carboxylate 1e (300 mg, 0.64 mmol), acetic anhydride (130 mg, 1.3 mmol), and anhydrous toluene (20 mL) were mixed, heated to 100° C. under stirring for 14 hrs. The mixture was cooled to room temperature and concentrated to remove solvent under reduced pressure to give a target crude product tert-butyl 3-(5-acetamido-4-methyl-6-(4-(morpholinomethyl)phenyl)pyridin-2-yl)piperidin-1-carboxylate 1f (350 mg, yellow viscous oil) which was directly used in the next reaction without further purification.

MS m/z (ESI):509[M+1]

Step 6

Tert-butyl 3-(7-(4-(morpholinomethyl)phenyl)-1H-pyrazolo[3,4-c]pyridin-5-yl)piperidin-1-carboxylate A mixture of tert-butyl 3-(5-acetamido-4-methyl-6-(4-(morpholinomethyl)phenyl)pyridin-2-yl)piperidin-1-carboxylate 1f (350 mg, crude), acetic anhydride (208 mg, 2.0 mmol), potassium acetate (87 mg, 0.88 mmol), and benzene (20 mL) was heated to 78° C. Isoamyl nitrite (117 mg, 1.0 mmol) was added immediately and the resulting mixture was stirred for 18 hrs. The mixture was cooled to room temperature and concentrated to remove solvent under reduced pressure. The residue was dissolved in a mixture of water (5 mL), and ethanol (15 mL) and lithium hydroxide monohydrate (100 mg) was added. The mixture was stirred at room temperature for 2 hrs and concentrated to remove solvent under reduced pressure. The residue was dispersed in water (10 mL), and extracted with ethyl acetate (50 mL×3). The organic phases were combined, dried over anhydrous sodium sulfate, filtered to remove the desiccant, and concentrated to remove solvent under reduced pressure. The residue was purified by column chromatography on silica gel (petroleum ether/ethyl acetate=1/1 to 1/2) to give a target product tert-butyl 3-(7-(4-(morpholinomethyl)phenyl)-1H-pyrazolo[3,4-c]pyridin-5-yl)piperidin-1-carboxylate g (130 mg, yellow solid), yield: two-step 40%.

MS m/z (ESI):478[M+1]

Step 7

4-(4-(5-(piperidin-3-yl)-1H-pyrazolo[3,4-c]pyridin-7-yl)phenmethyl)morpholine

Compound tert-butyl 3-(7-(4-(morpholinomethyl)phenyl)-1H-pyrazolo[3,4-c]pyridin-5-yl)piperidin-1-carboxylate 1g (130 mg, 0.27 mmol), trifluoroacetic acid (3 mL), and dichloromethane (3 mL) were mixed and stirred at room temperature for 14 hrs. Saturated sodium bicarbonate solution (30 mL) was added, and the mixture was extracted with dichloromethane (50 mL×3). The organic phases were combined, dried over anhydrous sodium sulfate, filtered to remove the desiccant, and concentrated to remove solvent under reduced pressure. The residue was purified by column chromatography on silica gel (dichloromethane/methanol=10/1) to give a target product 4-(4-(5-(piperidin-3-yl)-1H-pyrazolo[3,4-c]pyridin-7-yl)phenmethyl)morpholine 1h (100 mg, yellow viscous oil), yield: 98%.

MS m/z (ESI):378[M+1]

Step 8

1-(3-(7-(4-(morpholinomethyl)phenyl)-1H-pyrazolo[3,4-c]pyridin-5-yl)piperidin-1-yl)prop-2-en-1-one Compound 4-(4-(5-(piperidin-3-yl)-1H-pyrazolo[3,4-c]pyridin-7-yl)phenmethyl)morpholine 1h (0.15 g, 0.40 mmol), acryloyl chloride (91 mg, 0.56 mmol), solid sodium bicarbonate (86 mg, 0.86 mmol), water (5 mL), and tetrahydrofuran (15 mL) were mixed and stirred at room temperature for 2 hrs. The mixture was extracted with ethyl acetate (50 mL×3). The organic phases were combined, dried over anhydrous sodium sulfate, filtered to remove the desiccant, and concentrated to remove solvent under reduced pressure. The residue was purified by column chromatography on silica gel (dichloromethane/methanol=10/1) to give a target product 1-(3-(7-(4-(morpholinomethyl)phenyl)-1H-pyrazolo[3,4-c]pyridin-5-yl)piperidin-1-yl)prop-2-en-1-one 1 (20 mg, white solid), yield: 23%.

MS m/z (ESI):432[M+1]

$^1$H NMR (400 MHz, $CD_3OD$) δ 8.30-8.22 (m, 3H), 7.77 (dd, J=8.3, 2.3 Hz, 2H), 7.73 (d, J=10.0 Hz, 1H), 4.79 (m, 0.5H), 4.52 (m, 2.5H), 4.17 (m, 1H), 4.01 (m, 2H), 3.84 (m, 2H), 3.53 (dd, J=13.3, 11.0 Hz, 1H), 3.36 (m, 2H), 3.29-2.98 (m, 3H), 2.93-2.78 (m, 1H), 2.19 (s, 3H), 2.15 (s, 1H), 2.08 (s, 1H), 1.95 (d, J=3.3 Hz, 1H), 1.78-1.62 (m, 1H).

Example 2

1-(3-(7-(4-(oxetan-3-oxy)phenyl)-1H-pyrazolo[3,4-c]pyridin-5-yl)piperidin-1-yl)prop-2-en-1-one

2

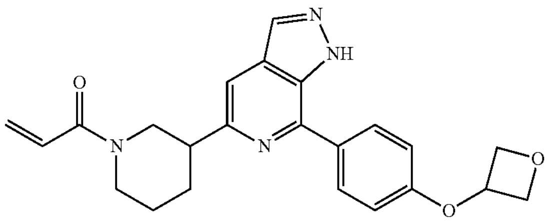

Example 2 was synthesized following the procedures in Example 1, except that 4-(4-(4,4,5,5-tetramethyl-1,3,2-dioxaborolan-2-yl)phenmethyl)morpholine was replaced with 4,4,5,5-tetramethyl-2-(4-(oxetan-3-oxy)phenyl)-1,3,2-dioxaborolane in Step 4.

MS m/z (ESI):405[M+1]

$^1$H NMR (400 MHz, $CDCl_3$) δ 11.04 (s, 1H), 8.15 (d, J=6.9 Hz, 1H), 8.00 (d, J=8.2 Hz, 2H), 7.45 (d, J=12.8 Hz, 1H), 6.98-6.82 (m, 2H), 6.68 (dd, J=16.6, 10.7 Hz, 1H), 6.31 (t, J=15.1 Hz, 1H), 5.69 (dd, J=27.8, 10.4 Hz, 1H), 5.31 (s, 1H), 5.09-4.98 (m, 2H), 4.89-4.74 (m, 2.5H), 4.70 (d, J=11.4 Hz, 0.5H), 4.29 (d, J=12.3 Hz, 0.5H), 4.05 (d, J=13.3 Hz, 0.5H), 3.51 (t, J=12.1 Hz, 0.5H), 3.20 (dd, J=29.8, 16.8 Hz, 2H), 2.83 (t, J=12.3 Hz, 0.5H), 2.22 (d, J=11.2 Hz, 1H), 2.14-1.97 (m, 1H), 1.89 (s, 1H), 1.71 (s, 1H).

Example 3

1-(3-(7-(4-phenoxyphenyl)-1H-pyrazolo[3,4-c]pyridin-5-yl)piperidin-1-yl)prop-2-en-1-one

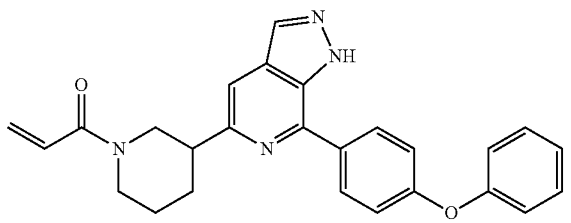

3

-continued

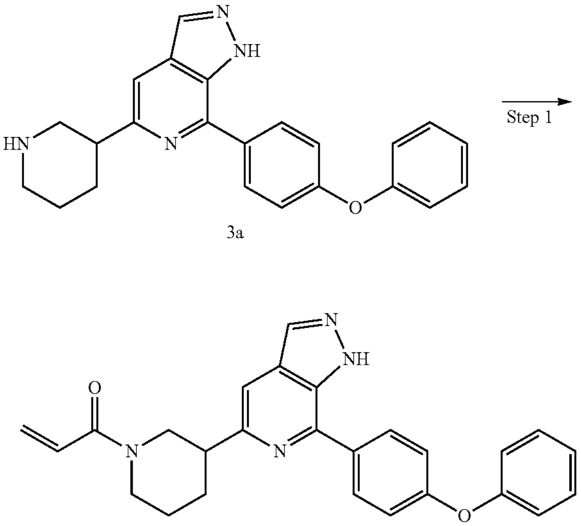

3a

3

Example 3a was synthesized following the procedures described in Steps 1-7 of Example 1, except that 4-(4-(4,4,5,5-tetramethyl-1,3,2-dioxaborolan-2-yl)phenmethyl)morpholine was replaced with (4-phenoxyphenyl) boric acid in Step 4.

MS m/z (ESI):371[M+1]

$^1$H NMR (400 MHz, $CD_3OD$) δ 8.35-8.28 (m, 1H), 8.10 (d, J=8.7 Hz, 2H), 7.78 (d, J=12.2 Hz, 1H), 7.52-7.40 (m, 2H), 7.23 (dd, J=7.8, 4.2 Hz, 3H), 7.18-7.09 (m, 2H), 3.68 (d, J=10.1 Hz, 1H), 3.47 (d, J=11.6 Hz, 3H), 3.22-3.09 (m, 1H), 2.26 (d, J=12.9 Hz, 1H), 2.17-1.92 (m, 3H).

Step 1

Compound 7-(4-phenoxyphenyl)-5-(piperidin-3-yl)-1H-pyrazolo[3,4-c]pyridine 3a (0.13 g, 0.40 mmol), acryloyl chloride (34 mg, 0.37 mmol), solid sodium bicarbonate (63 mg, 0.75 mmol), water (5 mL), and tetrahydrofuran (15 mL) were mixed and stirred at room temperature for 2 hrs. The mixture was extracted with ethyl acetate (50 mL×3). The organic phases were combined, dried over anhydrous sodium sulfate, filtered to remove the desiccant, and concentrated to remove solvent under reduced pressure. The residue was purified by column chromatography on silica gel (dichloromethane/methanol=10/1) to give a target product 3 1-(3-(7-(4-phenoxyphenyl)-1H-pyrazolo[3,4-c]pyridin-5-yl)piperidin-1-yl)prop-2-en-1-one (120 mg, white solid), yield: 83%.

MS m/z (ESI):425[M+1]

$^1$H NMR (400 MHz, $CDCl_3$) δ 10.81 (brs, 1H), 8.18 (s, 1H), 8.02 (d, J=8.0 Hz, 2H), 7.49 (s, 1H), 7.42 (t, J=7.8 Hz, 2H), 7.21 (t, J=6.9 Hz, 3H), 7.13 (d, J=7.9 Hz, 2H), 6.68 (d, J=7.0 Hz, 1H), 6.38-6.26 (m, 1H), 5.69 (dd, J=25.2, 10.5 Hz, 1H), 4.84 (s, 0.5H), 4.71 (d, J=11.9 Hz, 0.5H), 4.30 (d, J=13.5 Hz, 0.5H), 4.05 (d, J=12.8 Hz, 0.5H), 3.57-3.48 (m, 0.5H), 3.28-3.12 (m, 2H), 2.84-2.74 (m, 0.5H), 2.25-2.16 (m, 1H), 2.11-2.0 (s, 1H), 1.95-1.85 (m, 1H), 1.75-1.65 (m, 1H).

Example 4

(E)-4-(dimethylamino)-1-(3-(7-(4-phenoxyphenyl)-1H-pyrazolo[3,4-c]pyridin-5-yl)piperidin-1-yl)but-2-en-1-one

4

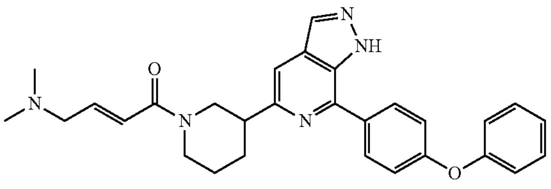

Compound 7-(4-phenoxyphenyl)-5-(piperidin-3-yl)-1H-pyrazolo[3,4-c]pyridine 3a (100 mg, 0.28 mmol), (E)-4-(dimethylamino)but-2-enic acid (53 mg, 0.32 mmol), 2-(7-azobenzotriazole)-N,N,N',N'-tetramethylurea hexafluorophosphate (154 mg, 0.41 mmol), triethylamine (82 mg, 0.81 mmol), and N,N-dimethylformamide (15 mL) were mixed and stirred at room temperature for 3 hrs. The mixture was desolventized under reduced pressure. The residue was purified by column chromatography on silica gel (dichloromethane/methanol=30/1 to 10/1) to give a target product (E)-4-(dimethylamino)-1-(3-(7-(4-phenoxyphenyl)-1H-pyrazolo[3,4-c]pyridin-5-yl)piperidin-1-yl)but-2-en-1-one 4 (45 mg, white solid), yield: 33%.

MS m/z (ESI):482[M+1]

$^{1}$H NMR (300 MHz, DMSO-$d_6$) δ 13.55 (brs, 1H), 8.26 (s, 3H), 7.60 (s, 1H), 7.47 (t, J=7.6 Hz, 2H), 7.31-7.06 (m, 5H), 6.59 (s, 2H), 4.48 (s, 1H), 4.23 (s, 1H), 3.13-2.97 (m, 5H), 2.21 (s, 7H), 2.08-1.96 (m, 1H), 1.88 (d, J=13.2 Hz, 1H), 1.70-1.50 (m, 1H).

Example 5

7-(4-phenoxyphenyl)-5-(1-(ethenylsulfonyl)piperidin-3-yl)-1H-pyrazolo[3,4-c]pyridine

5

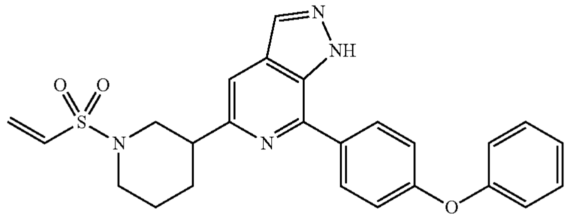

Compound 7-(4-phenoxyphenyl)-5-(piperidin-3-yl)-1H-pyrazolo[3,4-c]pyridine 3a (100 mg, 0.27 mmol), 2-chloroethanesulfonyl chloride (52 mg, 0.32 mmol), triethylamine (82 mg, 0.81 mmol), and dichloromethane (3 mL) were mixed and stirred for at room temperature for 1 hr. The mixture was concentrated to remove solvent under reduced pressure and the residue was purified by column chromatography on silica gel (petroleum ether/ethyl acetate=1/1 to 1/3) to give a target product 7-(4-phenoxyphenyl)-5-(1-(ethenylsulfonyl)piperidin-3-yl)-1H-pyrazolo[3,4-c]pyridine 5 (20 mg, white solid), yield: 16%.

MS m/z (ESI):461[M+1]

$^{1}$H NMR (400 MHz, $CDCl_3$) δ 8.21 (s, 1H), 8.01 (d, J=8.3 Hz, 2H), 7.59 (s, 1H), 7.43 (dd, J=8.4, 7.5 Hz, 2H), 7.22 (dd, J=7.9, 6.4 Hz, 3H), 7.17-7.09 (m, 2H), 6.51 (dd, J=16.7, 9.9 Hz, 1H), 6.27 (d, J=16.6 Hz, 1H), 6.05 (d, J=9.9 Hz, 1H), 3.95-3.86 (m, 1H), 3.75-3.79 (m, 1H), 3.20-3.10 (m, 2H), 2.90-2.75 (m, 1H), 2.20-2.09 (m, 1H), 1.99-1.85 (m, 2H), 1.65-1.50 (m, 2H).

Example 6

1-(3-(7-(4-phenoxyphenyl)-1H-pyrazolo[3,4-c]pyridin-5-yl)pyrrolidin-1-yl)prop-2-en-1-one

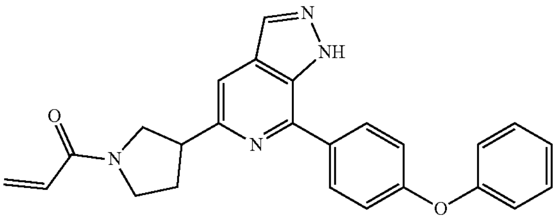

6

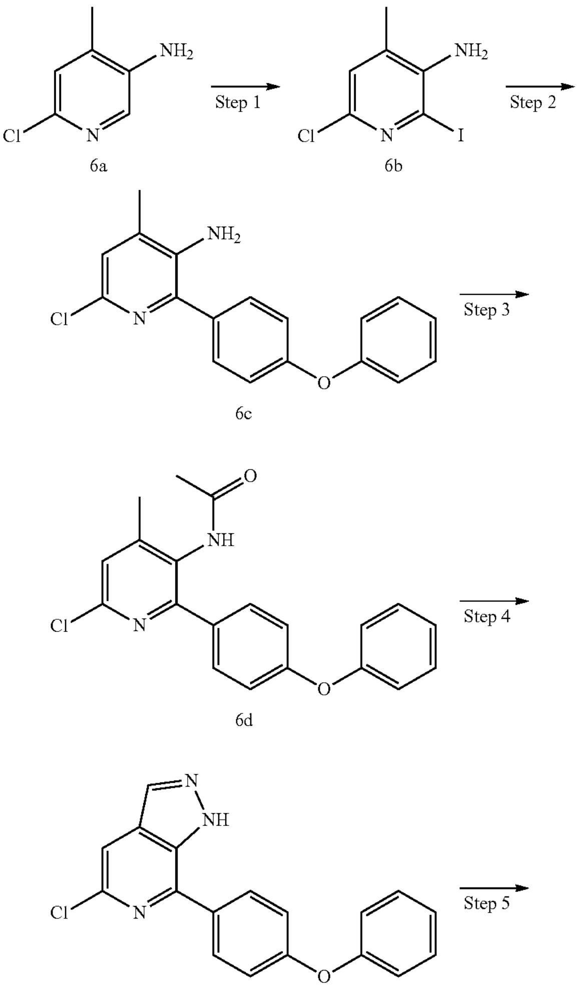

6a 6b 6c 6d 6e

-continued

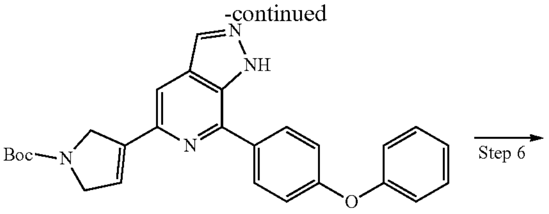

6f

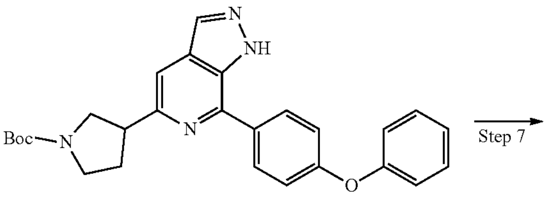

6g

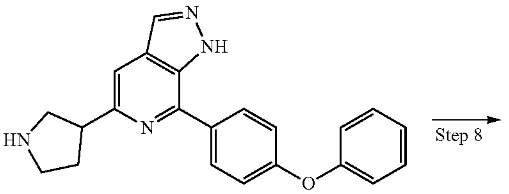

6h

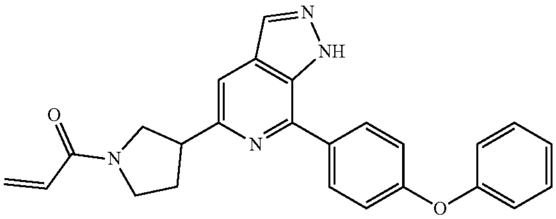

6

Step 1

6-chloro-2-iodo-4-methylpyridin-3-amine

Compound 6-chloro-4-methylpyridin-3-amine 6a (6.75 g, 47.3 mmol), N-iodosuccinimide (12.95 g, 57.6 mmol), and N,N-dimethylformamide (100 mL) were mixed at 0° C. and stirred at room temperature for 15 hrs. Next, water (100 ml) was added, and the mixture was extracted with ethyl acetate (150 mL×3). The organic phases were combined, dried over anhydrous sodium sulfate, filtered to remove the desiccant, and concentrated to remove solvent under reduced pressure. The residue was purified by column chromatography on silica gel (petroleum ether/ethyl acetate=10/1) to give a target product 6-chloro-2-iodo-4-methylpyridin-3-amine 6b (6.5 g, yellow solid), yield: 47%.

MS m/z (ESI):269[M+1]

Step 2

6-chloro-4-methyl-2-(4-phenoxyphenyl)pyridine-3-amine

Referring to the procedure for 1e of Example 1, 1,6-chloro-2-iodo-4-methylpyridin-3-amine 6b (3.0 g, 11.2 mmol) was used as starting material to give a target product 6-chloro-4-methyl-2-(4-phenoxyphenyl)pyridine-3-amine 6c (3.5 g, yellow solid), yield: 100%.

MS m/z (ESI):311[M+1]

Step 3

N-(6-chloro-4-methyl-2-(4-phenoxyphenyl)pyridine-3-yl)acetamide

Referring to the procedure for 1f of Example 1, 6-chloro-4-methyl-2-(4-phenoxyphenyl)pyridin-3-amine 6c (3.5 g, 11.2 mmol) was used as starting material to give a target product N-(6-chloro-4-methyl-2-(4-phenoxyphenyl)pyridin-3-yl)acetamide 6d (4.0 g, yellow solid), yield: 100%.

MS m/z (ESI):353[M+1]

Step 4

5-chloro-7-(4-phenoxyphenyl)-1H-pyrazolo[3,4-c]pyridine

Referring to the procedure for 1g of Example 1, N-(6-chloro-4-methyl-2-(4-phenoxyphenyl)pyridine-3-yl)acetamide 6d (3.4 g, 9.6 mmol) was used as starting material to give a target product 5-chloro-7-(4-phenoxyphenyl)-1H-pyrazolo[3,4-c]pyridine 6e (1.5 g, yellow solid), yield: 40%.

MS m/z (ESI):322[M+1]

Step 5

Tert-butyl 3-(7-(4-phenoxyphenyl)-1H-pyrazolo[3,4-c]pyridin-5-yl)-2,5-dihydro-1H-pyrrole-1-carboxylate Referring to the procedure for 1b of Example 1, 5-chloro-7-(4-phenoxyphenyl)-1H-pyrazolo[3,4-c]pyridine 6e (850 mg, 2.64 mmol), and tert-butyl 3-(4,4,5,5-tetramethyl-1,3,2-dioxaborolan-2-yl)-2,5-dihydro-1H-pyrrole-1-carboxylate (1.95 g, 6.6 mmol) were used as starting materials to give a target product tert-butyl 3-(7-(4-phenoxyphenyl)-1H-pyrazolo[3,4-c]pyridin-5-yl)-2,5-dihydro-1H-pyrrole-1-carboxylate 6f (700 mg, yellow solid), yield: 58%.

MS m/z (ESI):455[M+1]

Step 6

Tert-butyl 3-(7-(4-phenoxyphenyl)-1H-pyrazolo[3,4-c]pyridin-5-yl)pyrrolidine-1-carboxylate Referring to the procedure for 1c of Example 1, tert-butyl 3-(7-(4-phenoxyphenyl)-1H-pyrazolo[3,4-c]pyridin-5-yl)-2,5-dihydro-1H-pyrrole-1-carboxylate 6f (700 mg, 1.54 mmol) was used as starting material to give a target product tert-butyl 3-(7-(4-phenoxyphenyl)-1H-pyrazolo[3,4-c]pyridin-5-yl) pyrrolidine-1-carboxylate 6g (270 mg, yellow solid), yield: 39%.

MS m/z (ESI):457[M+1]

Step 7

7-(4-phenoxyphenyl)-5-(pyrrolidin-3-yl)-1H-pyrazolo[3,4-c]pyridine

Referring to the procedure for 1h of Example 1, tert-butyl 3-(7-(4-phenoxyphenyl)-1H-pyrazolo[3,4-c]pyridin-5-yl) pyrrolidine-1-carboxylate 6g (250 mg, 0.327 mmol) was used as starting material to give a target product tert-butyl 7-(4-phenoxyphenyl)-5-(pyrrolidin-3-yl)-1H-pyrazolo[3,4-c]pyridine 6h (95 mg, yellow solid), yield: 82%.

MS m/z (ESI):357[M+1]

Step 8

1-(3-(7-(4-phenoxyphenyl)-1H-pyrazolo[3,4-c]pyridin-5-yl)pyrrolidin-1-yl)prop-2-en-1-one Referring to the procedure for 1 of Example 1, 1,7-(4-phenoxyphenyl)-5-(pyrrolidin-3-yl)-1H-pyrazolo[3,4-c]

pyridine 6h (95 mg, 0.267 mmol) was used as starting material to give a target product 1-(3-(7-(4-phenoxyphenyl)-1H-pyrazolo[3,4-c]pyridin-5-yl)pyrrolidin-1-yl)prop-2-en-1-one 6 (45 mg, yellow solid), yield: 82%.

MS m/z (ESI):411[M+1]

$^1$H NMR (400 MHz, $CDCl_3$) δ 10.86 (brs, 1H), 8.18 (s, 1H), 7.99 (t, J=9.3 Hz, 2H), 7.50 (d, J=8.2 Hz, 1H), 7.45-7.38 (m, 2H), 7.20 (dd, J=11.5, 8.7 Hz, 3H), 7.15-7.09 (m, 2H), 6.58-6.36 (m, 2H), 5.71 (ddd, J=14.7, 10.0, 2.3 Hz, 1H), 4.20-4.07 (m, 1H), 4.00-3.60 (m, 4H), 2.58-2.30 (m, 2H).

Example 7

1-(4-(7-(4-phenoxyphenyl)-1H-pyrazolo[3,4-c]pyridin-5-yl)piperidin-1-yl)prop-2-en-1-one

7

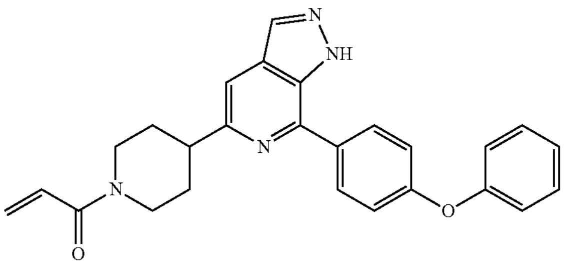

Example 7 was synthesized following the procedures in Example 6, except that tert-butyl 3-(4,4,5,5-tetramethyl-1,3,2-dioxaborolan-2-yl)-2,5-dihydro-1H-pyrrole-1-carboxylate was replaced with tert-butyl 4-(4,4,5,5-tetramethyl-1,3,2-dioxaborolan-2-yl)-5,6-dihydropyridine-1(2H)-carboxylate in Step 5.

MS m/z (ESI):371[M+1]

$^1$H NMR (400 MHz, DMSO-$d_6$) δ 13.65 (s, 1H), 8.23 (s, 1H), 8.09-8.08 (m, 2H), 7.57-7.44 (m, 3H), 7.23-7.11 (m, 5H), 6.90-6.84 (m, 1H), 6.13 (d, J=12.8 Hz, 1H), 5.68 (d, J=10.4 Hz, 1H), 4.62-4.59 (m, 1H), 4.23-4.19 (m, 1H), 3.02-3.12 (m, 2H), 2.83-2.77 (m, 1H), 2.02-1.99 (m, 2H), 1.76-1.70 (m, 2H).

Example 8

N-(3-(7-(4-phenoxyphenyl)-1H-pyrazolo[3,4-c]pyridin-5-yl)phenyl)acrylamide

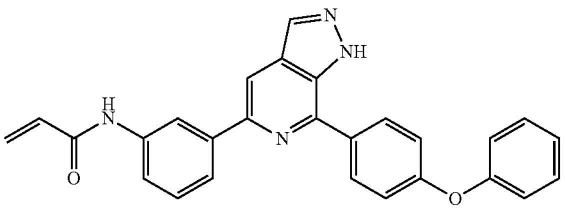

8

-continued

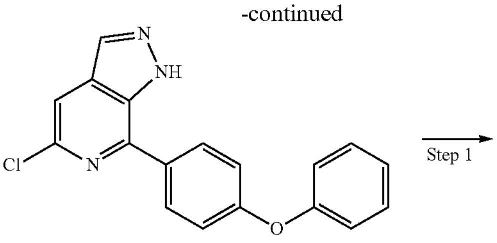

6e

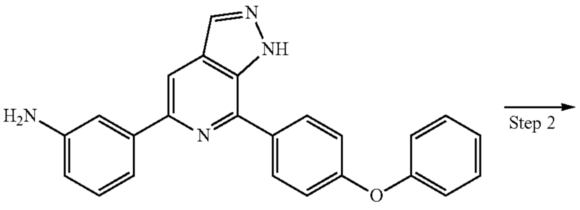

8b

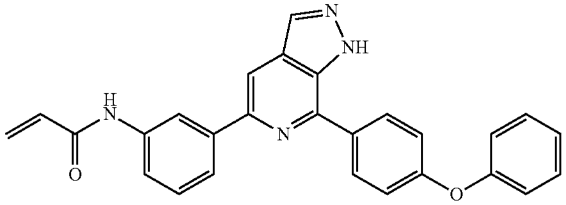

8

Step 1

3-(7-(4-phenoxyphenyl)-1H-pyrazolo[3,4-c]pyridin-5-yl)aniline

Referring to the procedure for 1b of Example 1, 5-chloro-7-(4-phenoxyphenyl)-1H-pyrazolo[3,4-c]pyridine (100 mg, 0.34 mmol), and (3-aminophenyl)boric acid 6e (51 mg, 0.37 mmol) were used as starting materials to give a target product 3-(7-(4-phenoxyphenyl)-1H-pyrazolo[3,4-c]pyridin-5-yl)aniline 8b (80 mg, grey solid), yield: 68%.

MS m/z (ESI):379[M+1]

Step 1

N-(3-(7-(4-phenoxyphenyl)-1H-pyrazolo[3,4-c]pyridin-5-yl)phenyl)acrylamide

Referring to the procedure for 1 of Example 1, 3-(7-(4-phenoxyphenyl)-1H-pyrazolo[3,4-c]pyridin-5-yl)aniline 8b (80 mg, 0.21 mmol) was used as starting material to give N-(3-(7-(4-phenoxyphenyl)-1H-pyrazolo[3,4-c]pyridin-5-yl)phenyl)acrylamide 8 (13 mg, yellow solid), yield: 15%.

MS m/z (ESI):433[M+1]

$^1$H NMR (400 MHz, DMSO-$d_6$) δ 13.82 (s, 1H), 10.28 (s, 1H), 8.46 (s, 1H), 8.37 (s, 1H), 8.23-8.19 (m, 3H), 7.89-7.79 (m, 2H), 7.49-7.43 (m, 3H), 7.25-7.15 (m, 5H), 6.50-6.46 (m, 1H), 6.31-6.27 (m, 1H), 5.79-5.77 (m, 1H).

Example 9

1-(4-(7-(4-phenoxyphenyl)-1H-pyrazolo[3,4-c]pyridin-5-yl)piperazin-1-yl)prop-2-en-1-one

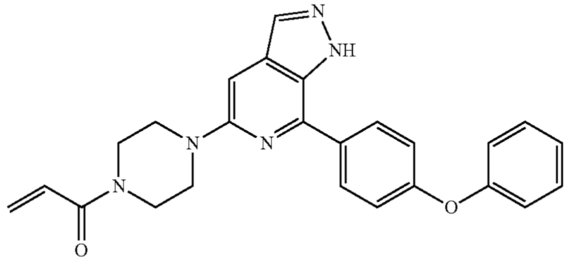

9

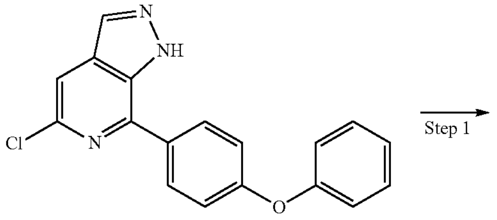

9a

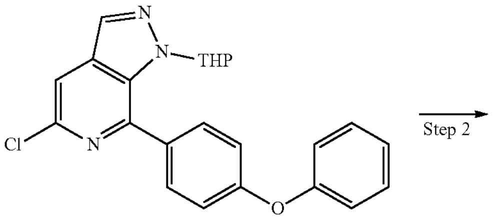

9b

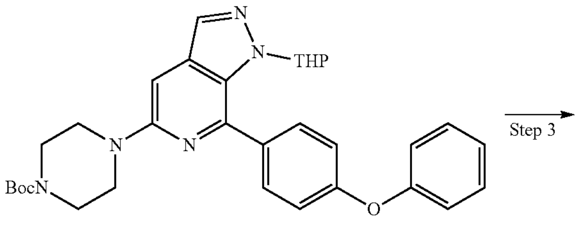

9c

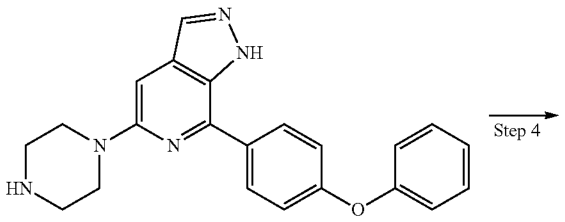

9d

-continued

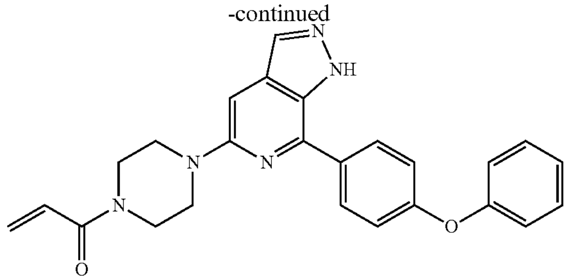

9

Step 1

5-chloro-7-(4-phenoxyphenyl)-1-(tetrahydro-2H-pyran-2-yl)-1H-pyrazolo[3,4-c]pyridine Compound 5-chloro-7-(4-phenoxyphenyl)-1H-pyrazolo[3,4-c]pyridine 9a (500 mg, 1.56 mmol), 3,4-dihydro-2H-pyrane (393 mg, 4.68 mmol), and dichloromethane (20 mL) were mixed at 0° C., and then p-toluenesulfonic acid (50 mg, 0.29 mmol) was added. The mixture was stirred at room temperature for 15 hrs. A saturated solution of sodium bicarbonate (10 mL) was added, and the mixture was extracted with dichloromethane (20 mL×3). The organic phases were combined, dried over anhydrous sodium sulfate, filtered to remove the desiccant, and concentrated to remove solvent under reduced pressure. The residue was purified by column chromatography on silica gel (petroleum ether/ethyl acetate=5/1) to give a target product 5-chloro-7-(4-phenoxyphenyl)-1-(tetrahydro-2H-pyran-2-yl)-1H-pyrazolo[3,4-c]pyridine 9b (350 mg, pale yellow solid), yield: 55%.

MS m/z (ESI): 406[M+1]

Step 2 tert-butyl 4-(7-(4-phenoxyphenyl)-1-(tetrahydro-2H-pyran-2-yl)-1H-pyrazolo[3,4-c]pyridin-5-yl)piperazine-1-carboxylate Compound 5-chloro-7-(4-phenoxyphenyl)-1-(tetrahydro-2H-pyran-2-yl)-1H-pyrazolo[3,4-c]pyridine 9b (350 mg, 0.864 mmol), tert-butylpiperazine-1-carboxylate (344 mg, 1.73 mmol), cesium carbonate (562 mg, 1.73 mmol), (2-dicyclohexylphosphino-2',6'-dimethoxy-1,1'-biphenyl)[2-(2-aminoethylphenyl)] palladium (II) chloride methyl tert-butyl ether adduct (68 mg, 0.09 mmol), and 1,4-dioxane (20 mL) were mixed, degassed, and heated in microwave at 150° C. under nitrogen for 5 hrs. The mixture was cooled to room temperature, and concentrated to remove solvent under reduced pressure. The residue was purified by column chromatography on silica gel (dichloromethane/methanol=20/1), to produce a target compound tert-butyl 4-(7-(4-phenoxyphenyl)-1-(tetrahydro-2H-pyran-2-yl)-1H-pyrazolo[3,4-c]pyridin-5-yl)piperazine-1-carboxylate 9c (50 mg, yellow oil), yield: 18%.

MS m/z (ESI):556[M+1]

Step 3

7-(4-phenoxyphenyl)-5-(piperazin-1-yl)-1H-pyrazolo[3,4-c]pyridine

Compound tert-butyl 4-(7-(4-phenoxyphenyl)-1-(tetrahydro-2H-pyran-2-yl)-1H-pyrazolo[3,4-c]pyridin-5-yl)piperazine-1-carboxylate 9c (50 mg, 0.0899 mmol), and dichloromethane (3 mL) were mixed, and then a solution of hydrogen chloride in ethanol (4 M, 1 mL, 4 mmol) was added. The mixture was stirred at room temperature for 14 hrs, and concentrated to remove solvent under reduced pressure to give a target product 7-(4-phenoxyphenyl)-5-(piperazin-1-yl)-1H-pyrazolo[3,4-c]pyridine 9d (crude, pale yellow solid) which was directly used in the next reaction without further purification.

MS m/z (ESI):372[M+1]

Step 4

1-(4-(7-(4-phenoxyphenyl)-1H-pyrazolo[3,4-c]pyridin-5-yl)piperazin-1-yl)prop-2-en-1-one Referring to the procedure for 1 of Example 1, 7-(4-phenoxyphenyl)-5-(piperazin-1-yl)-1H-pyrazolo[3,4-c] pyridine 9d (crude) was used as the starting material to give 1-(4-(7-(4-phenoxyphenyl)-1H-pyrazolo[3,4-c]pyridin-5-yl)piperazin-1-yl)prop-2-en-1-one 9 (10 mg, nearly white solid), yield: two-step 26%.

MS m/z (ESI):426[M+1]

$^1$H NMR (400 MHz, $CDCl_3$) δ 10.62 (s, 1H), 8.02 (t, J=18.6 Hz, 3H), 7.42 (t, J=7.9 Hz, 2H), 7.16 (dd, J=31.1, 8.2 Hz, 5H), 6.89 (s, 1H), 6.66 (dd, J=16.8, 10.5 Hz, 1H), 6.47-6.29 (m, 1H), 5.78 (d, J=10.6 Hz, 1H), 3.89 (d, J=51.8 Hz, 4H), 3.61 (d, J=30.3 Hz, 4H).

Example 10

N-(1-(7-(4-phenoxyphenyl)-1H-pyrazolo[3,4-c]pyridin-5-yl)pyrrolidin-3-yl)acrylamide

10

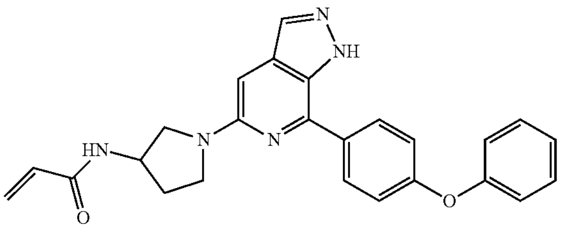

Example 10 was synthesized following the procedures in Example 9, except that tert-butyl piperazine-1-carboxylate was replaced with tert-butyl pyrrolidin-3-yl carbamate in Step 2.

MS m/z (ESI):426[M+1]

$^1$H NMR (400 MHz, $CDCl_3$) δ 10.42 (s, 1H), 7.99 (d, J=8.7 Hz, 3H), 7.41 (t, J=8.0 Hz, 2H), 7.16 (dt, J=8.6, 7.7 Hz, 4H), 6.57 (s, 1H), 6.35 (dd, J=16.9, 1.2 Hz, 1H), 6.21-5.84 (m, 2H), 5.68 (dd, J=10.3, 1.2 Hz, 1H), 4.80 (s, 1H), 3.92-3.56 (m, 4H), 2.43 (dd, J=13.5, 6.5 Hz, 1H), 2.13 (d, J=4.8 Hz, 1H).

Example 11

1-(3-((7-(4-phenoxyphenyl)-1H-pyrazolo[3,4-c]pyridin-5-yl)amino)pyrrolidin-1-yl)prop-2-en-1-one

11

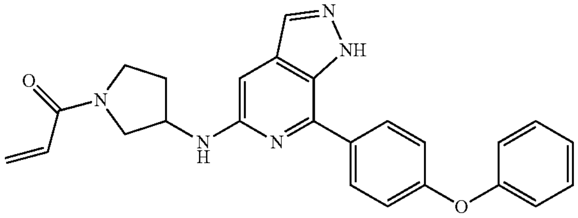

Example 11 was synthesized following the procedures in Example 9, except that tert-butyl piperazine-1-carboxylate was replaced with tert-butyl 3-aminopyrrolidine-1-carboxylate in Step 2.

MS m/z (ESI):426[M+1]

$^1$H NMR (400 MHz, $CD_3OD$) δ 8.07-7.93 (m, 2H), 7.43 (t, J=8.0 Hz, 2H), 7.24-7.06 (m, 4H), 6.65 (ddd, J=27.4, 24.5, 16.1 Hz, 2H), 6.29 (ddd, J=16.9, 7.6, 2.0 Hz, 1H), 5.75 (ddd, J=16.4, 10.4, 1.9 Hz, 1H), 4.61-4.44 (m, 1H), 4.09 (dd, J=10.6, 6.1 Hz, 1H), 3.99-3.85 (m, 1H), 3.78 (dt, J=15.1, 6.9 Hz, 1H), 3.63 (ddd, J=25.3, 14.2, 6.2 Hz, 2H), 2.25 (m, 3H).

Example 12

1-(4-(7-(4-(pyridin-2-oxy)phenyl)-1H-pyrazazo[3,4-c]pyridin-5-yl)piperidin-1-yl)prop-2-en-1-one

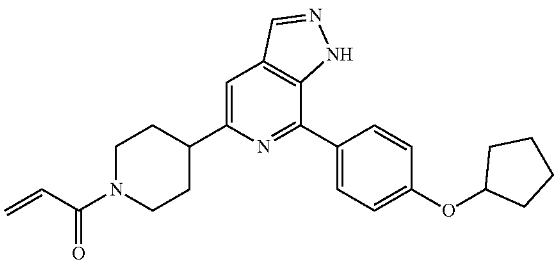

12

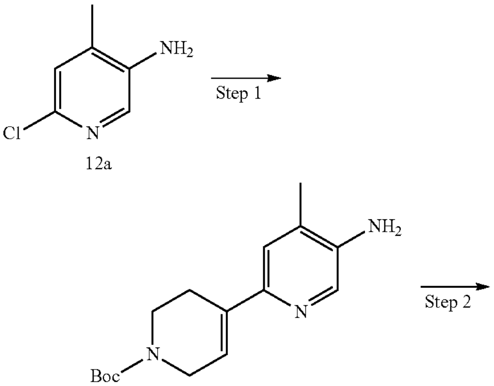

12a

12b

-continued

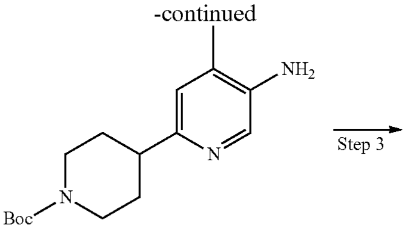

12c

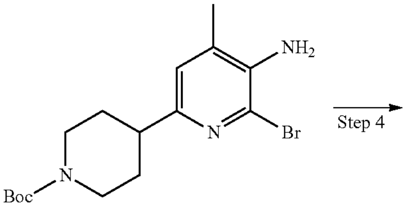

12d

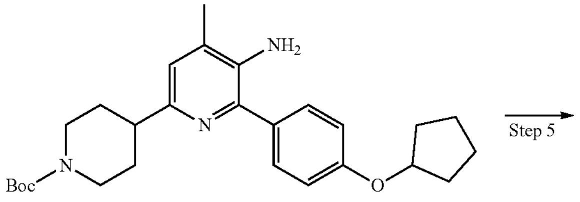

12e

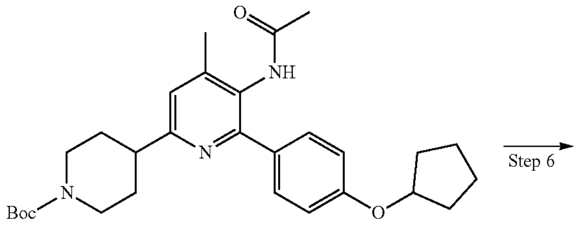

12f

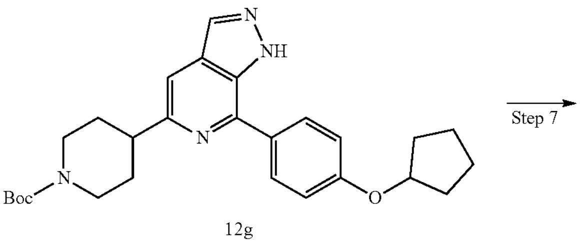

12g

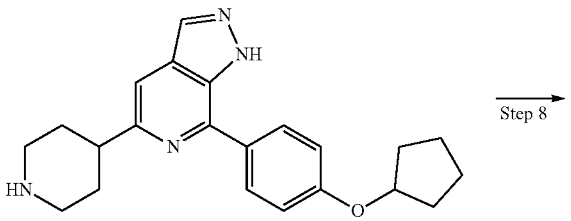

12h

-continued

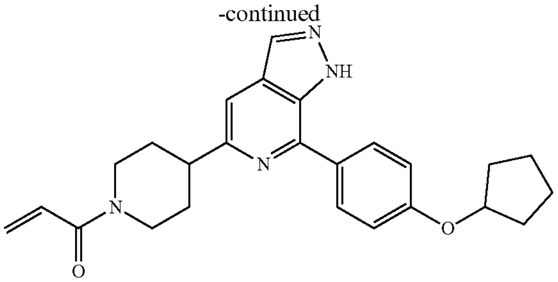

12

Example 12 was synthesized following the procedures in Example 1, except that tert-butyl 3-(4,4,5,5-tetramethyl-1,3,2-dioxaborolan-2-yl)-5,6-dihydropyridine-1(2H)-carboxylate was replaced with tert-butyl 4-(4,4,5,5-tetramethyl-1,3,2-dioxaborolan-2-yl)-3,6-dihydropyridine-1(2H)-carboxylate in Step 1, and 4-(4-(4,4,5,5-tetramethyl-1,3,2-dioxaborolan-2-yl)phenmethyl)morpholine was replaced with 4,4,5,5-tetramethyl-2-(4-(oxetan-3-oxy)phenyl)-1,3,2-dioxaborolane in Step 4.

MS m/z (ESI):417[M+1]

$^1$H NMR (400 MHz, DMSO-$d_6$) δ 13.62 (s, 1H), 8.21 (s, 1H), 8.02 (d, J=7.0 Hz, 2H), 7.51 (s, 1H), 7.08 (d, J=8.7 Hz, 2H), 6.88 (dd, J=16.7, 10.5 Hz, 1H), 6.13 (dd, J=16.7, 2.5 Hz, 1H), 5.69 (dd, J=10.4, 2.5 Hz, 1H), 4.93 (dd, J=7.1, 4.5 Hz, 1H), 4.61 (d, J=12.4 Hz, 1H), 4.21 (d, J=12.6 Hz, 1H), 3.23 (t, J=12.2 Hz, 1H), 3.09 (s, 1H), 2.80 (s, 1H), 1.99 (dd, J=8.5, 5.5 Hz, 4H), 1.83-1.55 (m, 8H).

Example 13

1-(4-(7-(4-(pyridin-2-oxy)phenyl)-1H-pyrazolo[3,4-c]pyridin-5-yl)piperidin-1-yl)prop-2-en-1-one

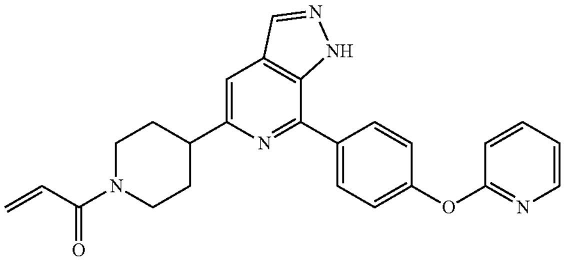

13

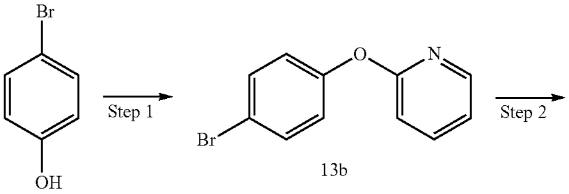

13a 13b

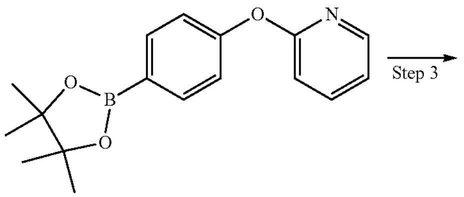

13c

-continued

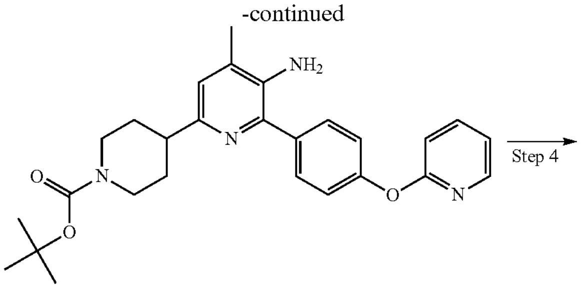

13d

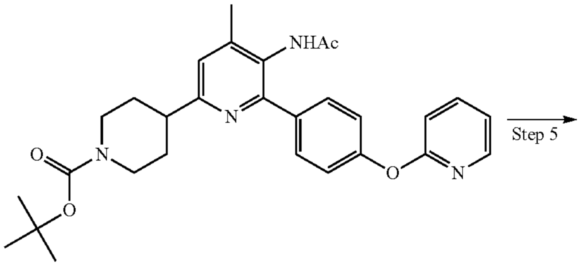

13e

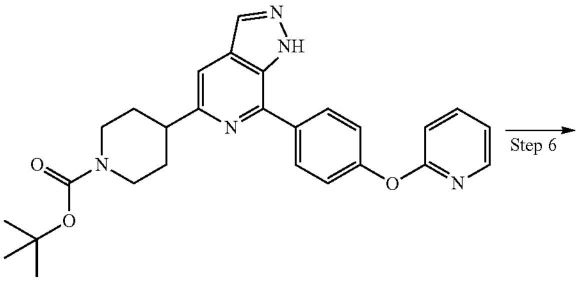

13f

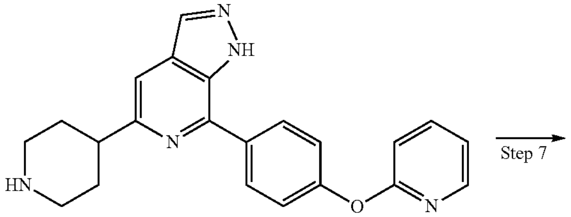

13g

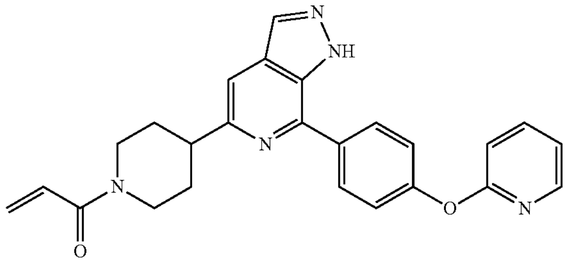

13

Step 1

2-(4-bromophenoxy)pyridine

Compound 4-bromophenol 13a (5.00 g, 28.9 mmol), 2-bromopyridine (4.60 g, 28.9 mmol), copper powder (184 mg, 2.89 mmol), cuprous iodide (550 mg, 2.89 mmol), potassium carbonate (11.9 g, 86.7 mmol), and N-methylpiperidin-2-one (30 mL) were mixed and heated to 150° C. under stirring for 15 hrs. The mixture was cooled to room temperature, and then water (90 mL) was added. The mixture was extracted with dichloromethane (80 mL×3). The organic phases were combined, dried over anhydrous sodium sulfate, filtered to remove the desiccant, and concentrated to remove solvent under reduced pressure. The residue was purified by column chromatography on silica gel (petroleum ether/ethyl acetate=5/1) to give a target product 2-(4-bromophenoxy)pyridine 13b (2.60 g, pale yellow oil), yield: 36%.

MS m/z (ESI): 250, 252[M+1]

Step 2

2-(4-(4,4,5,5-tetramethyl-1,3,2-dioxaborolan-2-yl)phenoxy)pyridine

Compound 2-(4-bromophenoxy)pyridine 13b (1.3 g, 5.24 mmol), 4,4,4',4',5,5,5',5'-octamethyl-2,2'-di(1,3,2-dioxaborolanyl) (1.59 g, 6.28 mmol), potassium acetate (1.03 g, 10.50 mmol), [1,1'-bis(diphenylphosphine)ferrocene]palladium dichloride (380 mg, 0.524 mmol), and 1,4-dioxane (70 mL) were mixed, degassed, and heated at 90° C. under nitrogen for 15 hrs. The mixture was cooled to room temperature, and concentrated to remove solvent under reduced pressure. The residue was purified by column chromatography on silica gel (petroleum ether/ethyl acetate=10/1), to produce a target compound 2-(4-(4,4,5,5-tetramethyl-1,3,2-dioxaborolan-2-yl)phenoxy)pyridine 13c (1.30 g, yellow oil), yield: 79%.

MS m/z (ESI): 298[M+1]

Steps 3 to 7

1-(4-(7-(4-(pyridin-2-oxy)phenyl)-1H-pyrazolo[3,4-c]pyridin-5-yl)piperidin-1-yl)prop-2-en-1-one 13 was prepared following the procedures described in Steps 4 to 8 of Example 12, except that 4-(4-(4,4,5,5-tetramethyl-1,3,2-dioxaborolan-2-yl)phenmethyl)morpholine and tert-butyl 3-(5-amino-6-bromo-4-methylpyridin-2-yl)piperidin-1-carboxylate were replaced with 2-(4-(4,4,5,5-tetramethyl-1,3,2-dioxaborolan-2-yl)phenoxy)pyridine and tert-butyl 4-(5-amino-6-bromo-4-methylpyridin-2-yl)piperidin-1-carboxylate in Step 3.

MS m/z (ESI):426[M+1]

$^1$H NMR (400 MHz, $CD_3OD$) δ 8.19 (s, 1H), 8.06 (d, J=7.0 Hz, 2H), 7.59 (s, 1H), 7.41 (dd, J=15.1, 8.2 Hz, 1H), 7.25 (d, J=8.5 Hz, 2H), 6.88 (dt, J=19.0, 8.5 Hz, 4H), 6.24 (dd, J=16.8, 1.4 Hz, 1H), 5.77 (d, J=10.7 Hz, 1H), 4.77 (d, J=13.0 Hz, 1H), 4.30 (d, J=13.1 Hz, 1H), 3.38 (s, 1H), 3.21 (s, 1H), 2.93 (t, J=12.6 Hz, 1H), 2.14 (s, 2H), 1.91 (s, 2H).

Example 14

1-(4-(7-(2-fluoro-4-phenoxyphenyl)-1H-pyrazolo[3,4-c]pyridin-5-yl)piperidin-1-yl)prop-2-en-1-one

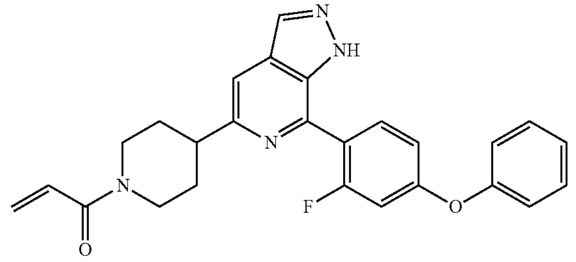

14

-continued

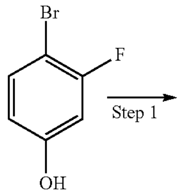

14a

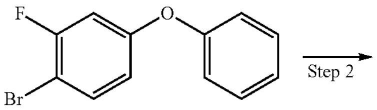

14b

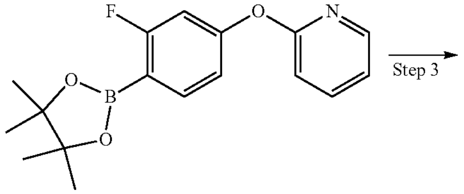

14c

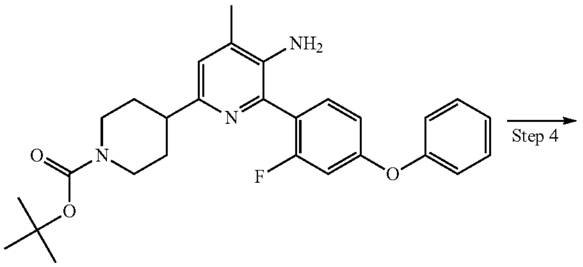

14d

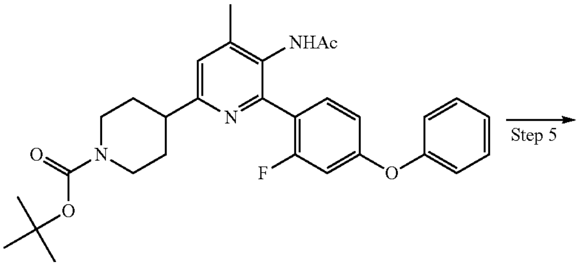

14e

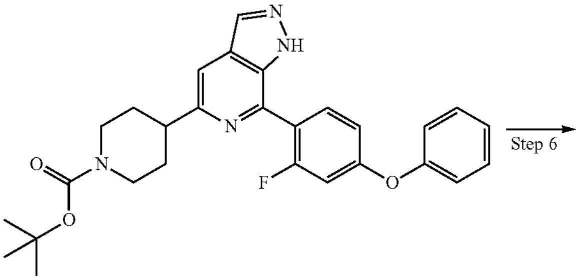

14f

-continued

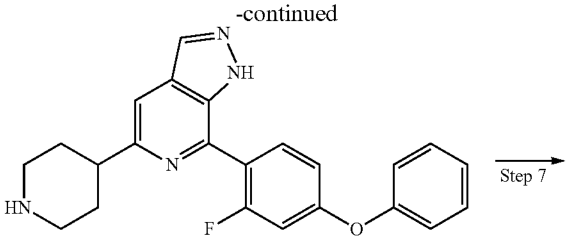

14g

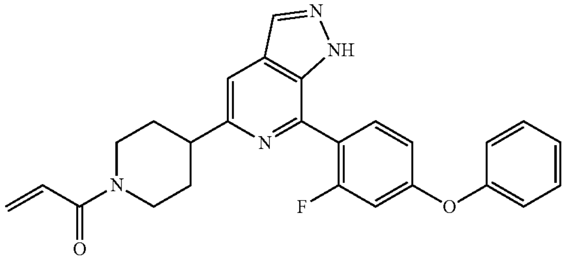

14

Step 1

1-bromo-2-fluoro-4-phenoxybenzene

Compound 3-fluoro-4-bromophenol 14a (3.00 g, 15.7 mmol), phenylboronic acid (3.82 g, 31.4 mmol), cupric acetate (2.85 g, 15.7 mmol), triethylamine (4.8 g, 47.1 mmol), molecular sieve (5 g), and dichloromethane (120 mL) were mixed and stirred at room temperature for 15 hrs. The mixture was filtered to remove the molecular sieve, and desolventized under reduced pressure. The residue was purified by column chromatography on silica gel (petroleum ether/ethyl acetate=5/1) to give a target product 1-bromo-2-fluoro-4-phenoxybenzene 14b (3.30 g, white solid), yield: 78%.

$^1$H NMR (400 MHz, $CDCl_3$) δ 7.48 (t, J=8.3 Hz, 1H), 7.41 (t, J=7.9 Hz, 2H), 7.21 (t, J=7.4 Hz, 1H), 7.06 (d, J=8.4 Hz, 2H), 6.80 (dd, J=9.8, 2.7 Hz, 1H), 6.73 (dd, J=8.8, 2.7 Hz, 1H).

Step 2

2-(2-fluoro-4-phenoxyphenyl)-4,4,5,5-tetramethyl-1,3,2-dioxaborolane

Following the synthetic procedures for 12c in Example 12, 1-bromo-2-fluoro-4-phenoxybenzene (3.30 g, 12.3 mmol) was used as starting material to produce 2-(2-fluoro-4-phenoxyphenyl)-4,4,5,5-tetramethyl-1,3,2-dioxaborolane 13c (1.40 g, pale yellow solid), yield: 36%.

$^1$H NMR (400 MHz, $CDCl_3$) δ 7.73-7.67 (m, 1H), 7.40 (t, J=7.9 Hz, 2H), 7.20 (t, J=7.4 Hz, 1H), 7.07 (d, J=7.8 Hz, 2H), 6.78 (dd, J=8.3, 2.2 Hz, 1H), 6.64 (dd, J=10.7, 2.2 Hz, 1H), 1.37 (s, 12H).

Steps 3 to 7

1-(4-(7-(2-fluoro-4-phenoxyphenyl)-1H-pyrazolo[3,4-c]pyridin-5-yl)piperidin-1-yl)prop-2-en-1-one 14 was prepared following the procedures described in Steps 4 to 8 of Example 12, except that 4-(4-(4,4,5,5-tetramethyl-1,3,2-dioxaborolan-2-yl)phenmethyl)morpholine and tert-butyl 3-(5-amino-6-bromo-4-methylpyridin-2-yl)piperidin-1-carboxylate were replaced with 2-(2-fluoro-4-phenoxyphenyl)-4,4,5,5-tetramethyl-1,3,2-dioxaborolane and tert-butyl 4-(5-amino-6-bromo-4-methylpyridin-2-yl) piperidin-1-carboxylate in Step 3.

MS m/z (ESI):443[M+1]

$^1$H NMR (400 MHz, $CD_3OD$) δ 8.17 (s, 1H), 7.75 (t, J=8.4 Hz, 1H), 7.67 (s, 1H), 7.47 (t, J=8.0 Hz, 2H), 7.25 (t, J=7.4 Hz, 1H), 7.21-7.11 (m, 2H), 7.01 (dd, J=8.5, 2.0 Hz, 1H), 6.89 (ddd, J=27.5, 14.2, 6.4 Hz, 2H), 6.23 (dd, J=16.8, 2.0 Hz, 1H), 5.77 (dd, J=10.7, 1.9 Hz, 1H), 4.76 (d, J=12.5 Hz, 1H), 4.29 (d, J=14.0 Hz, 1H), 3.35 (d, J=11.0 Hz, 1H), 3.21 (t, J=11.8 Hz, 1H), 2.92 (t, J=12.7 Hz, 1H), 2.13 (s, 2H), 1.89 (td, J=12.2, 5.3 Hz, 2H).

Example 15

1-(4-(7-(4-(3-fluorophenoxyl)phenyl)-1H-pyrazolo [3,4-c]pyridin-5-yl)piperidin-1-yl)prop-2-en-1-one

15

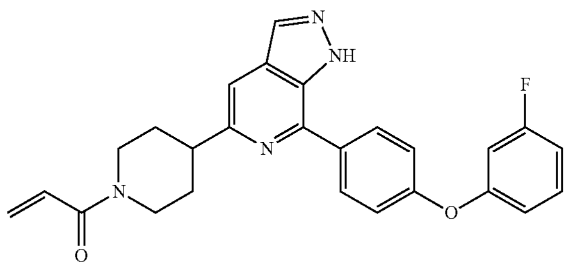

15 was prepared following the procedures of Example 14, except that 3-fluoro-4-bromophenol and phenylboronic acid were replaced with p-bromophenol and m-fluorophenylboronic acid in Step 1.

MS m/z (ESI):443[M+1]

$^1$H NMR (400 MHz, $CD_3OD$) δ 8.38 (s, 1H), 8.22 (dd, J=5.0, 1.3 Hz, 1H), 8.13 (d, J=7.7 Hz, 2H), 7.99-7.82 (m, 2H), 7.42 (d, J=8.6 Hz, 2H), 7.23 (dd, J=6.8, 5.4 Hz, 1H), 7.14 (d, J=8.3 Hz, 1H), 6.87 (dd, J=16.8, 10.7 Hz, 1H), 6.25 (dd, J=16.8, 2.0 Hz, 1H), 5.79 (dd, J=10.7, 2.0 Hz, 1H), 4.81 (d, J=13.4 Hz, 1H), 4.35 (d, J=13.4 Hz, 1H), 3.38 (d, J=12.9 Hz, 2H), 2.94 (s, 1H), 2.18 (s, 2H), 1.99-1.84 (m, 2H).

Example 16

1-(4-(7-(4-(pyrrolidin-1-ylmethyl)phenyl)-1H-pyrazolo[3,4-c]pyridin-5-yl)piperidin-1-yl)prop-2-en-1-one

16

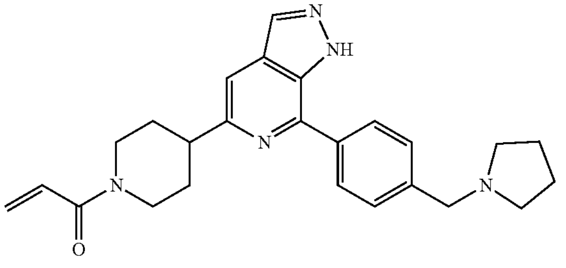

16 was prepared following the procedures described in Steps 4 to 8 of Example 13, except that 2-(4-(4,4,5,5-tetramethyl-1,3,2-dioxaborolan-2-yl)phenoxy)pyridine was replaced with 1-(4-(4,4,5,5-tetramethyl-1,3,2-dioxaborolan-2-yl)benzyl)pyrrolidine as starting material.

MS m/z (ESI):416[M+1]

$^1$H NMR (400 MHz, $CD_3OD$) δ 8.20 (s, 1H), 8.07 (d, J=8.0 Hz, 2H), 7.69-7.57 (m, 3H), 6.85 (dd, J=16.8, 10.7 Hz, 1H), 6.24 (dd, J=16.8, 1.9 Hz, 1H), 5.77 (dd, J=10.6, 1.9 Hz, 1H), 4.76 (d, J=12.9 Hz, 1H), 4.30 (d, J=13.5 Hz, 1H), 3.98 (s, 2H), 3.36 (d, J=14.7 Hz, 1H), 3.20 (ddd, J=15.4, 7.7, 3.7 Hz, 1H), 3.00-2.80 (m, 5H), 2.13 (t, J=9.9 Hz, 2H), 2.04-1.81 (m, 6H).

Example 17

1-(3-(7-(4-phenoxyphenyl)-1H-pyrazolo[3,4-c]pyridin-5-yl)piperidin-1-yl)but-2-yn-1-one

17

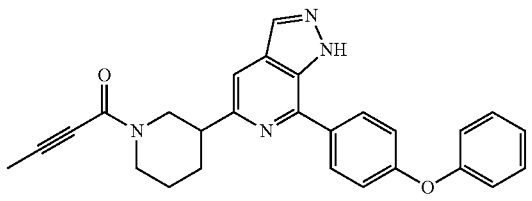

17 was prepared following the procedures of Example 4, except that (E)-4-(dimethylamino)but-2-enic acid was replaced with but-2-ynoic acid.

MS m/z (ESI):416[M+1]

$^1$H NMR (400 MHz, $CD_3OD$) δ 8.19 (d, J=7.0 Hz, 1H), 8.07 (t, J=8.6 Hz, 2H), 7.62 (d, J=10.3 Hz, 1H), 7.43 (t, J=7.9 Hz, 2H), 7.20 (dd, J=8.2, 4.1 Hz, 3H), 7.12 (d, J=8.2 Hz, 2H), 4.69 (t, J=9.3 Hz, 1H), 4.54-4.41 (m, 1H), 3.61-3.52 (m, 0.5H), 3.28 (s, 0.5H), 3.24-3.16 (m, 0.5H), 3.15-2.95 (m, 1H), 2.91-2.86 (m, 0.5H), 2.23-2.18 (m, 1H), 2.15-1.88 (m, 5H), 1.80-1.58 (m, 1H).

Example 18

4-(5-(1-acryloylpyrrolidin-3-yl)-1H-pyrazolo[3,4-c] pyridin-7-yl)-N-(pyridin-2-yl) benzamide

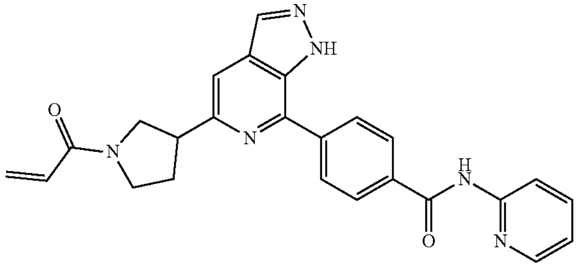

18

-continued

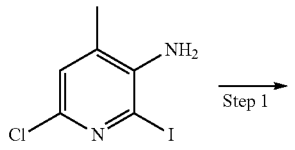

18a

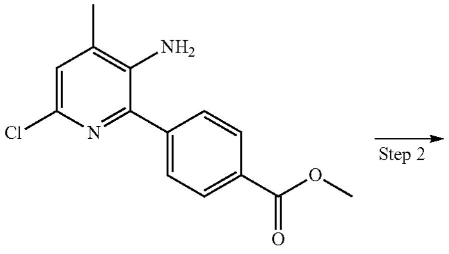

18b

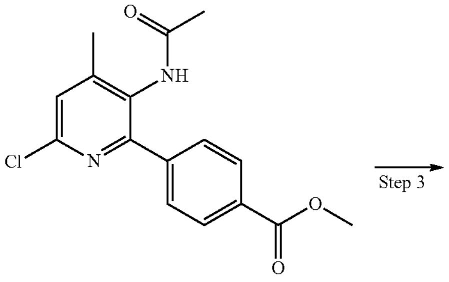

18c

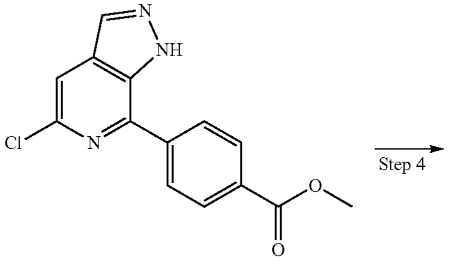

18d

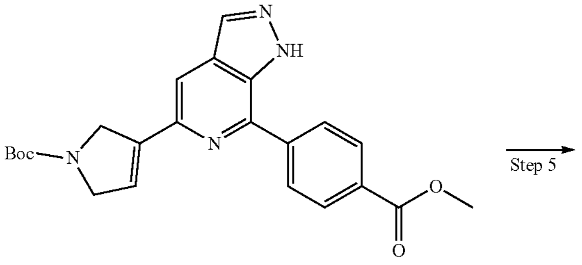

18e

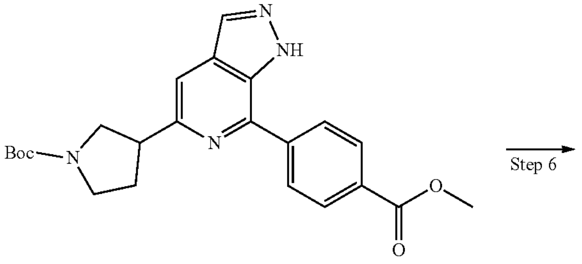

18f

-continued

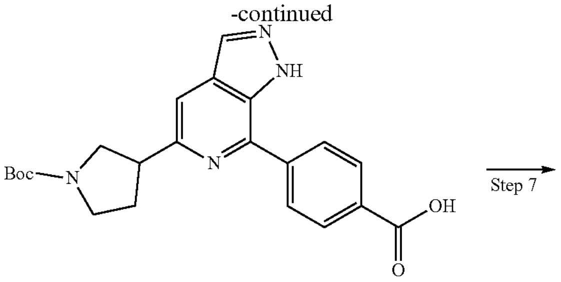

18g

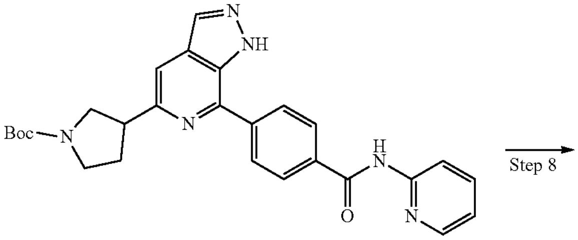

18h

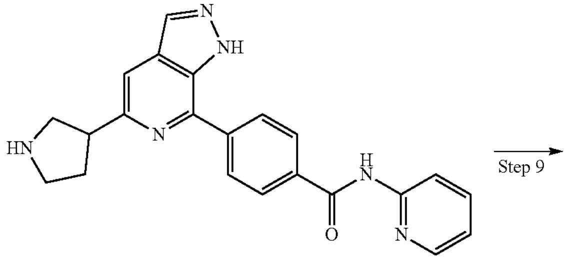

18i

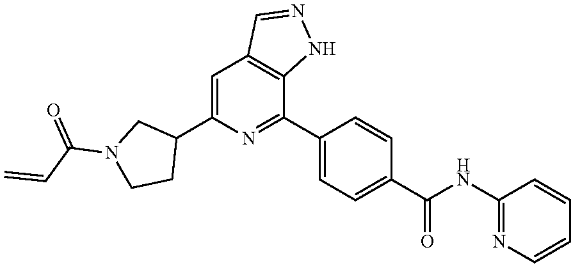

18

Steps 1 to 5

Tert-butyl 3-(7-(4-(methoxycarbonyl)phenyl)-1H-pyrazolo[3,4-c]pyridin-5-yl)pyrrolidine-1-carboxylate 18f was prepared following the procedures described in Steps 2 to 6 of Example 6, except that (4-phenoxyphenyl) boric acid was replaced with methyl 4-(4,4,5,5-tetramethyl-1,3,2-dioxaborolan-2-yl) benzoate in Step 1.

MS m/z (ESI):423[M+1]

Step 6

4-(5-(1-(tert-butoxycarbonyl)pyrrolidin-3-yl)-1H-pyrazolo[3,4-c]pyridin-7-yl) benzoic acid Compound tert-butyl 3-(7-(4-(methoxycarbonyl)phenyl)-1H-pyrazolo[3,4-c]pyridin-5-yl)pyrrolidine-1-carboxylate 18f (422 mg, 1.0 mmol), lithium hydroxide (52 mg, 10.0 mmol), water (10 mL), and tetrahydrofuran (10 mL) were mixed and stirred at room temperature for 14 hrs. The reaction solution was adjusted to pH=6 with 1 M diluted hydrochloric acid, and extracted with dichloromethane (50 mL×3). The organic phases were combined, dried over anhydrous sodium sulfate, filtered to remove the desiccant, and concentrated to remove solvent under reduced pressure to give a target product 4-(5-(1-(tert-butoxycarbonyl)pyrrolidin-3-yl)-1H-pyrazolo[3,4-c]pyridin-7-yl)benzoic acid 18g (300 mg, crude), which was directly used in the next reaction without further purification.

MS m/z (ESI):409[M+1]

Step 7

Tert-butyl 3-(7-(4-(pyridin-2-ylcarbamoyl)phenyl)-1H-pyrazolo[3,4-c]pyridin-5-yl)pyrrolidine-1-carboxylate Compound 4-(5-(1-(tert-butoxycarbonyl)pyrrolidin-3-yl)-1H-pyrazolo[3,4-c]pyridin-7-yl) benzoic acid 18g (204 mg, 0.5 mmol), triethylamine (194 mg, 3.0 mmol), and dichloromethane (20 mL) were mixed, and then 2,4,6-tripropyl-1,3,5,2,4,6-trioxytriphosphoric acid-2,4,6-trioxide (477 mg, 1.5 mmol) was added. The mixture was stirred at room temperature for 14 hrs, and then a saturated solution of sodium bicarbonate (10 mL) was added. The reaction mixture was extracted with dichloromethane (50 mL×3). The organic phases were combined, dried over anhydrous sodium sulfate, filtered to remove the desiccant, and concentrated to remove solvent under reduced pressure. The residue was purified by column chromatography on silica gel (dichloromethane/methanol=20/1) to give a target product tert-butyl 3-(7-(4-(pyridin-2-ylcarbamoyl)phenyl)-1H-pyrazolo[3,4-c]pyridin-5-yl)pyrrolidine-1-carboxylate 18h (80 mg, yellow solid), yield: 33%.

MS m/z (ESI):485[M+1]

Step 8

N-(pyridin-2-yl)-4-(5-(pyrrolidin-3-yl)-1H-pyrazolo[3,4-c]pyridin-7-yl) benzamide Following the synthetic procedure for 1h of Example 1, tert-butyl 3-(7-(4-(pyridin-2-ylcarbamoyl)phenyl)-1H-pyrazolo[3,4-c]pyridin-5-yl)pyrrolidine-1-carboxylate (80 mg, 0.17 mmol) was used as starting material to produce N-(pyridin-2-yl)-4-(5-(pyrrolidin-3-yl)-1H-pyrazolo[3,4-c]pyridin-7-yl)benzamide 18i (50 mg, crude).

MS m/z (ESI):385[M+1]

Step 9

4-(5-(1-acryloylpyrrolidin-3-yl)-1H-pyrazolo[3,4-c]pyridin-7-yl)-N-(pyridin-2-yl)benzamide Following the synthetic procedure for 1 of Example 1, N-(pyridin-2-yl)-4-(5-(pyrrolidin-3-yl)-1H-pyrazolo[3,4-c]pyridin-7-yl)benzamide 18i (50 mg, 0.13 mmol) was used as starting material to produce a target product 4-(5-(1-acryloylpyrrolidin-3-yl)-1H-pyrazolo[3,4-c]pyridin-7-yl)-N-(pyridin-2-yl)benzamide 18 (12 mg, yellow solid), yield: 12%.

MS m/z (ESI):439[M+1]

$^1$H NMR (400 MHz, $CDCl_3$) δ 11.13 (s, 1H), 9.69 (s, 1H), 8.66-8.56 (m, 1H), 8.36 (s, 1H), 8.30-8.14 (m, 3H), 7.96 (s, 1H), 7.80 (s, 1H), 7.57 (t, J=10.6 Hz, 1H), 7.23 (s, 1H), 6.93-6.79 (m, 1H), 6.51 (tdd, J=16.8, 12.4, 8.0 Hz, 2H), 5.78-5.66 (m, 1H), 4.22-4.05 (m, 1H), 4.03-3.60 (m, 4H), 2.46 (dt, J=32.0, 7.5 Hz, 2H).

Example 19

4-(5-(1-(but-2-ynoyl)pyrrolidin-3-yl)-1H-pyrazolo[3,4-c]pyridin-7-yl)-N-(pyridin-2-yl)benzamide

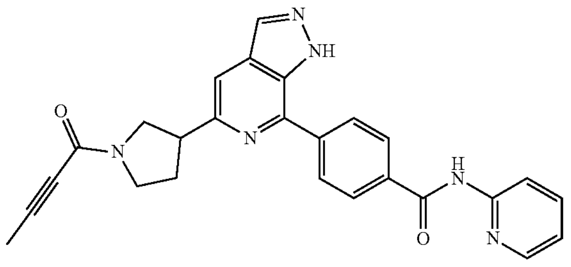

19

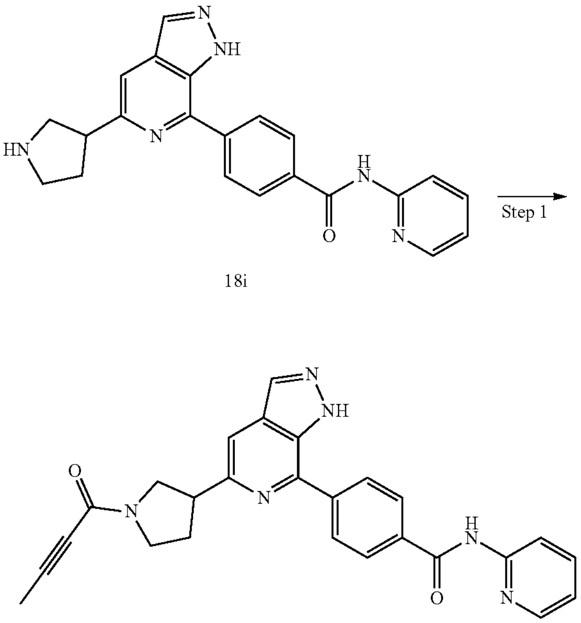

18i

19

Compound N-(pyridin-2-yl)-4-(5-(pyrrolidin-3-yl)-1H-pyrazolo[3,4-c]pyridin-7-yl)benzamide 18i (384 mg, 1.0 mmol), but-2-ynoyl chloride (113 mg, 1.1 mmol), solid sodium bicarbonate (232 mg, 3.0 mmol), water (4 mL), and tetrahydrofuran (16 mL) were mixed and stirred at room temperature for 1 hr. The mixture was extracted with ethyl acetate (50 mL×3). The organic phases were combined, dried over anhydrous sodium sulfate, filtered to remove the desiccant, and concentrated to remove solvent under reduced pressure. The residue was purified by column chromatography on silica gel (dichloromethane/methanol=20/1) to give a target product 4-(5-(1-(but-2-ynacyl)pyrrolidin-3-yl)-1H-pyrazolo[3,4-c]pyridin-7-yl)-N-(pyridin-2-yl)benzamide 19 (72 mg, white solid), yield: 16%.

MS m/z (ESI):439[M+1]

$^1$H NMR (400 MHz, $CD_3OD$) δ 8.53 (t, J=7.4 Hz, 2H), 8.47 (d, J=5.8 Hz, 1H), 8.43-8.33 (m, 4H), 8.03 (d, J=7.8 Hz, 1H), 7.94 (d, J=8.9 Hz, 1H), 7.71 (t, J=6.9 Hz, 1H), 4.28 (dd, J=10.9, 7.4 Hz, 0.5H), 3.95 (m, 4H), 3.66-3.56 (m, 0.5H), 2.63-2.36 (m, 2H), 2.06 (d, J=20.4 Hz, 3H).

Example 20

1-(3-(7-(4-phenoxyphenyl)-1H-indazol-5-yl)piperidin-1-yl)prop-2-en-1-one

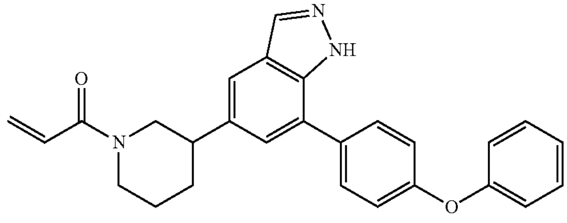

20

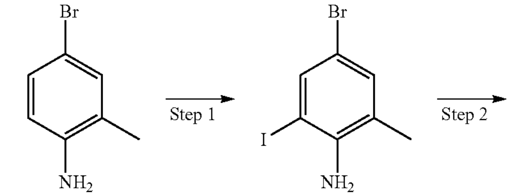

20a 20b

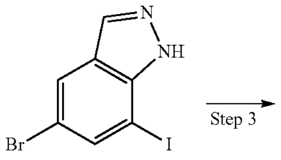

20c

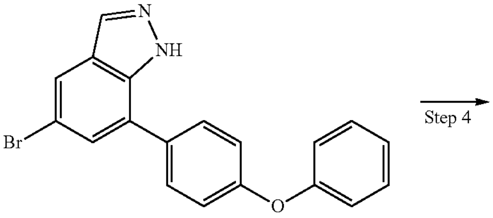

20d

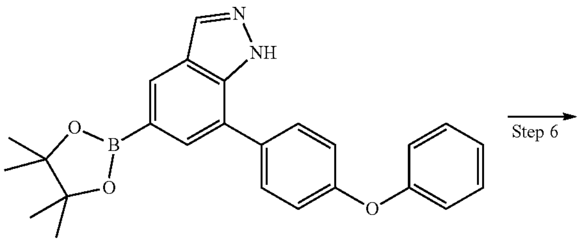

20e

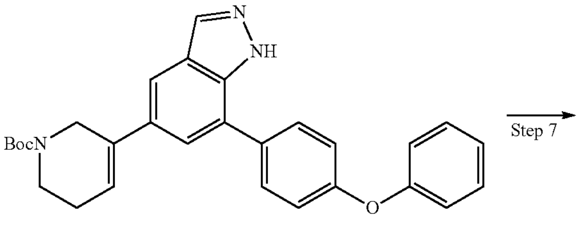

20f

-continued

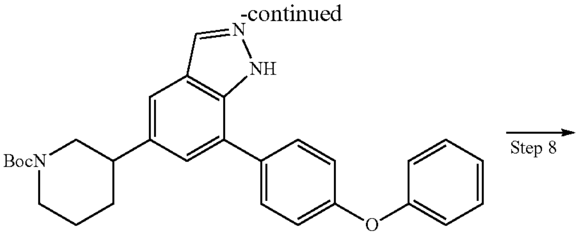

20g

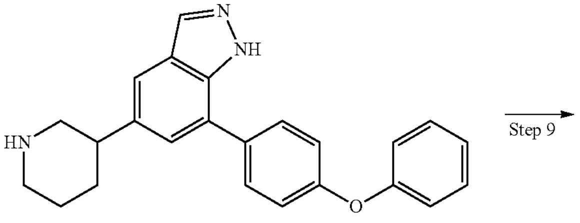

20h

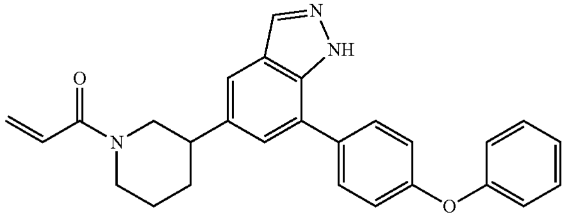

20

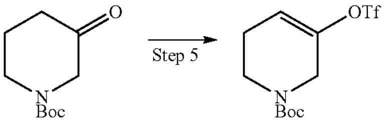

20i 20j

Step 1

4-bromo-2-iodo-6-methylaniline

Compound 4-bromo-2-methylaniline 20a (5 g, 26.87 mmol), N-iodosuccinimide (6.05 g, 26.87 mmol), p-toluenesulfonic acid (0.5 g, 2.91 mmol), and acetonitrile (100 mL) were mixed at room temperature and stirred for 3 hrs, and then saturated sodium bicarbonate (50 mL) was added. The mixture was extracted with ethyl acetate (50 mL×2). The organic phases were combined, dried over anhydrous sodium sulfate, filtered to remove the desiccant, and concentrated to remove solvent under reduced pressure. The residue was purified by column chromatography on silica gel (petroleum ether/ethyl acetate=5/1) to give a target product 4-bromo-2-iodo-6-methylaniline 20b (3.5 g, white solid), yield: 42%.

MS m/z (ESI):312, 314[M+1]

Step 2

5-bromo-7-iodo-1H-indazole

Compound 4-bromo-2-iodo-6-methylaniline 20b (3.5 g, 11.2 mmol), acetic acid (45 mL), and water (2.1 mL) were mixed at room temperature, and then sodium nitrite (851 mg, 12.3 mmol) was added. The mixture was stirred at room temperature for another 1 hr, and then water (200 mL) was added. The mixture was adjusted to pH=9 by using a saturated solution of sodium bicarbonate, and extracted with ethyl acetate (200 mL×2). The organic phases were combined, and concentrated to remove solvent under reduced pressure. The residue was purified by column chromatography on silica gel (petroleum ether/ethyl acetate=5/1) to give a target product 5-bromo-7-iodo-1H-indazole 20c (2.5 g, brown solid), yield: 69%.

MS m/z (ESI):323, 325[M+1]

Step 3

5-bromo-7-(4-phenoxyphenyl)-1H-indazole

Compound 5-bromo-7-iodo-1H-indazole 20c (2.0 g, 6.2 mmol), (4-phenoxyphenyl)boric acid (1.46 g, 6.8 mmol), cesium carbonate (4.04 g, 12.4 mmol), [1,1'-bis(diphenylphosphine)ferrocene]palladium dichloride (453 mg, 0.62 mmol), 1,4-dioxane (50 mL), and water (10 mL) were mixed, degassed, and heated at 100° C. under nitrogen for 12 hrs. The mixture was cooled to room temperature, and then water (100 mL) was added. Next, the mixture was extracted with ethyl acetate (100 mL×2). The organic phases were combined, and desolventized under reduced pressure. The residue was purified by column chromatography on silica gel (dichloromethane/methanol=30/1), to produce a target compound 5-bromo-7-(4-phenoxyphenyl)-1H-indazole 20d (1.6 g, white solid), yield: 71%.

MS m/z (ESI):365, 367[M+1]

Step 4

7-(4-phenoxyphenyl)-5-(4,4,5,5-tetramethyl-1,3,2-dioxaborolan-2-yl)-1H-indazole

Compound 5-bromo-7-(4-phenoxyphenyl)-1H-indazole 20d (730 mg, 2 mmol), 4,4,4',4',5,5,5',5'-octamethyl-2,2'-di(1,3,2-dioxaborolanyl) (1.22 g, 4.0 mmol), potassium acetate (589 mg, 6 mmol), [1,1'-bis(diphenylphosphine)ferrocene]palladium dichloride (146 mg, 0.2 mmol), and 1,4-dioxane (20 mL) were mixed, degassed, and heated at 90° C. under nitrogen for 12 hrs. The mixture was cooled to room temperature, and concentrated to remove solvent under reduced pressure. The residue was purified by column chromatography on silica gel (petroleum ether/ethyl acetate=5/1), to produce a target compound 7-(4-phenoxyphenyl)-5-(4,4,5,5-tetramethyl-1,3,2-dioxaborolan-2-yl)-1H-indazole 20e (480 mg, white solid), yield: 34%.

MS m/z (ESI):413[M+1]

Step 5

Tert-butyl 5-(((trifluoromethyl)sulfonyl)oxo)-3,6-dihydropyridine-1 (2H)-carboxylate Compound tert-butyl 3-carbonylpiperidin-1-carboxylate 20i (10 g, 50 mmol) was dissolved in tetrahydrofuran (200 mL) under nitrogen protection and cooled to −78° C., and then a solution of lithium di-isopropyl amide in tetrahydrofuran (2 M, 30 mL) was added. The mixture was stirred at the aforesaid temperature for 1 hr, and then N-phenyl-bis(trifluoromethanesulfonimide) (19.6 g, 55 mmol) was added. Next, the mixture was gradually warmed to room temperature and stirred for another 3 hrs. The reaction was quenched with water (5 mL). The reaction mixture was poured into water (300 mL), and extracted with ethyl acetate (300 mL×2). The organic phases were combined and concentrated to remove solvent under reduced pressure to give a target product tert-butyl 5-(((trifluoromethyl)sulfonyl)oxo)-3,6-dihydropyridine-1(2H)-carboxylate 20j (4.8 g, brown oil), yield: 29%.

$^1$H NMR (400 MHz, $CDCl_3$) δ 5.97-5.89 (m, 1H), 4.07-4.00 (m, 2H), 3.52-3.44 (m, 2H), 2.34-2.26 (m, 2H), 1.48 (s, 9H).

Step 6

Tert-butyl 5-(7-(4-phenoxyphenyl)-1H-indazol-5-yl)-3,6-dihydropyridine-1 (2H)-carboxylate Compound 7-(4-phenoxyphenyl)-5-(4,4,5,5-tetramethyl-1,3,2-dioxaborolan-2-yl)-1H-indazole 20e (2.3 g, 5.58 mmol), tert-butyl 5-(((trifluoromethyl)sulfonyl)oxo)-3,6-dihydropyridine-1(2H)-carboxylate 20j (2.8 g, 8.37 mmol), cesium carbonate (3.6 g, 11.16 mmol), [1,1'-bis(diphenylphosphine)ferrocene]palladium dichloride (408 mg, 0.2 mmol), 1,4-dioxane (80 mL), and water (16 mL) were mixed, degassed, and heated at 100° C. under nitrogen for 12 hrs. The mixture was cooled to room temperature and concentrated to remove solvent. The residue was dispersed in water (50 mL) and extracted with ethyl acetate (300 mL×2). The organic phases were combined, and concentrated to remove solvent under reduced pressure. The residue was purified by column chromatography on silica gel (dichloromethane/methanol=20/1), to produce a target compound tert-butyl 5-(7-(4-phenoxyphenyl)-1H-indazol-5-yl)-3,6-dihydropyridine-1(2H)-carboxylate 20f (2.2 g, white solid), yield: 85%.

MS m/z (ESI):468[M+1]

Step 7

Tert-butyl 3-(7-(4-phenoxyphenyl)-1H-indazol-5-yl) piperidin-1-carboxylate

Compound tert-butyl 5-(7-(4-phenoxyphenyl)-1H-indazol-5-yl)-3,6-dihydropyridine-1(2H)-carboxylate 20f (1.4 g, 2.99 mmol), Pd—C(400 mg), and methanol (30 mL) were mixed, degassed, and stirred at room temperature under hydrogen atmosphere for 16 hrs. The mixture was filtered, and concentrated to remove solvent under reduced pressure to produce a target product tert-butyl 3-(7-(4-phenoxyphenyl)-1H-indazol-5-yl)piperidin-1-carboxylate 20g (1.3 g, brown oil), yield: 92%.

MS m/z (ESI): 470[M+1]

Step 8

7-(4-phenoxyphenyl)-5-(piperidin-3-yl)-1H-indazole

Compound tert-butyl 3-(7-(4-phenoxyphenyl)-1H-indazol-5-yl)piperidin-1-carboxylate 20g (1.1 g, 2.3 mmol) was dissolved in a solution of hydrogen chloride in ethyl acetate (1 M, 25 mL, 25 mmol), and stirred at room temperature for 12 hrs. The mixture was concentrated to remove solvent under reduced pressure to produce a target product 7-(4-phenoxyphenyl)-5-(piperidin-3-yl)-1H-indazole 20h (1.1 g, yellow solid), yield 100%.

MS m/z (ESI):370[M+1]

Step 9

1-(3-(7-(4-phenoxyphenyl)-1H-indazol-5-yl)piperidin-1-yl)prop-2-en-1-one

Compound 7-(4-phenoxyphenyl)-5-(piperidin-3-yl)-1H-indazole 20h (500 mg, 1.23 mmol), acryloyl chloride (111 mg, 1.23 mmol), solid sodium bicarbonate (210 mg, 2.46 mmol), water (12.5 mL), and tetrahydrofuran (12.5 mL) were mixed and stirred at room temperature for 2 hrs. The mixture was extracted with ethyl acetate (50 mL×3). The organic phases were combined, dried over anhydrous sodium sulfate, filtered to remove the desiccant, and concentrated to remove solvent under reduced pressure. The residue was purified by column chromatography on silica gel (dichloromethane/methanol=20/1) to give a target product 1-(3-(7-(4-phenoxyphenyl)-1H-indazol-5-yl)piperidin-1-yl)prop-2-en-1-one 20 (20 mg, white solid), yield: 40%.

MS m/z (ESI):424[M+1]

$^1$H NMR (400 MHz, $CDCl_3$) δ 8.10 (s, 1H), 7.68-7.62 (m, 2H), 7.60 (s, 1H), 7.42 (dd, J=8.3, 7.6 Hz, 2H), 7.35 (s, 1H), 7.19 (d, J=8.2 Hz, 3H), 7.13 (dd, J=8.6, 0.9 Hz, 2H), 6.65 (d, J=10.6 Hz, 1H), 6.33 (d, J=16.9 Hz, 1H), 5.77-5.64 (m, 1H), 4.86 (dd, J=45.3, 12.8 Hz, 1H), 4.22-4.06 (m, 1H), 3.27-3.11 (m, 1H), 2.91 (d, J=10.6 Hz, 1H), 2.80-2.68 (m, 1H), 2.21 (d, J=13.2 Hz, 1H), 1.98-1.81 (m, 2H), 1.75-1.63 (m, 1H).

Example 21

1-(2-(7-(4-phenoxyphenyl)-1H-pyrazolo[3,4-c]pyridin-5-yl)pyrrolidin-1-yl)prop-2-en-1-one

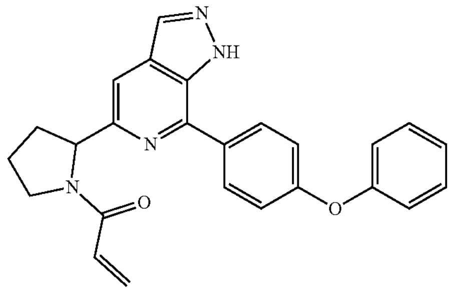

21

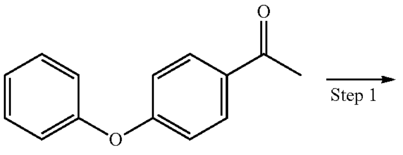

21a

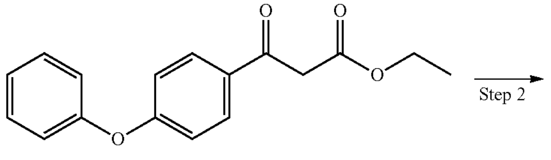

21b

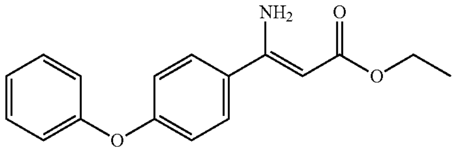

21c

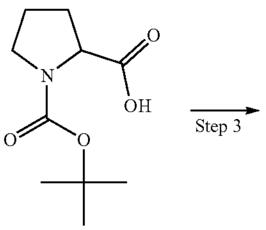

21d

-continued

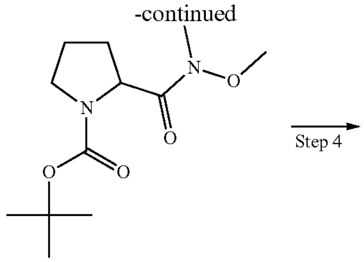

21e

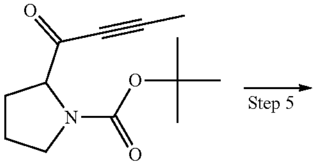

21f

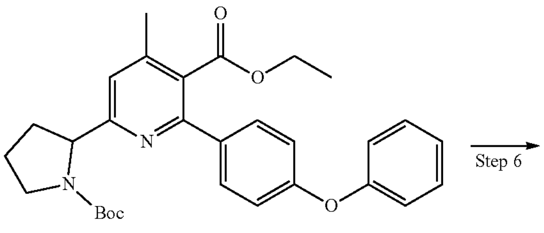

21g

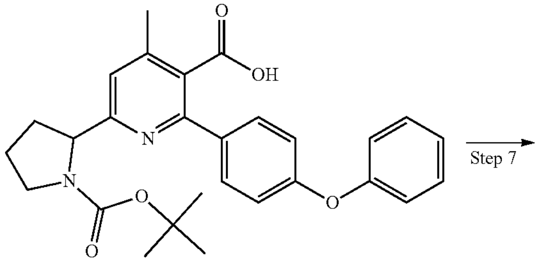

21h

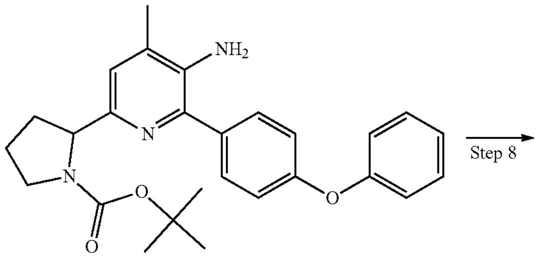

21i

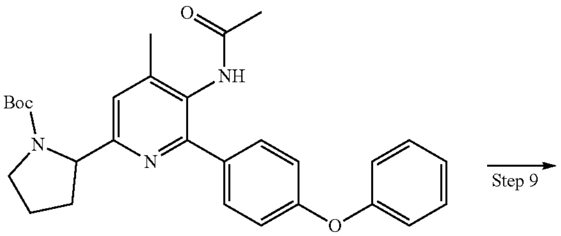

21j

-continued

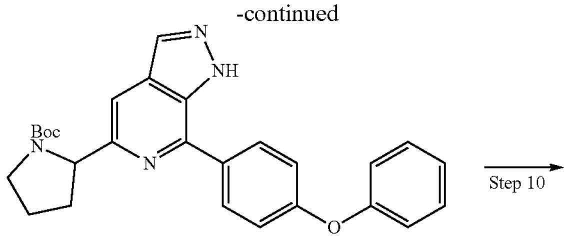

21k

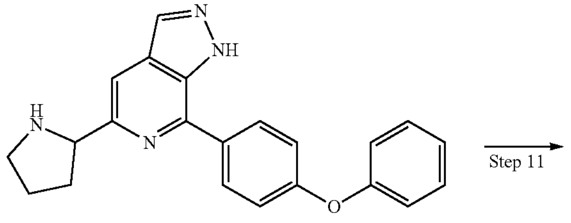

21l

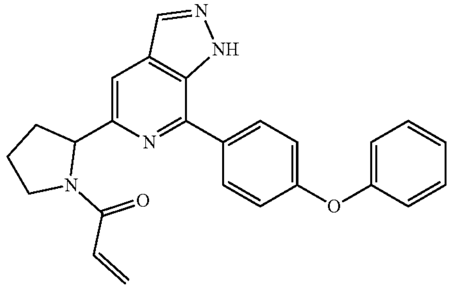

21

Step 1

Ethyl 3-carbonyl-3-(4-phenoxyphenyl)propionate

A mixture of 1-(4-phenoxyphenyl)ethanone 21a (4.24 g, 20 mmol), sodium hydride (60%, 2.0 g, 50 mmol), and toluene (30 mL) was heated to 90° C., and then compound diethyl carbonate (5.9 g, 50 mmol) was added. The reaction mixture was stirred at reflux for 45 min. The mixture was cooled to room temperature, and adjusted with a saturated ammonium chloride solution to neutral and extracted with ethyl acetate (100 mL×3). The organic phases were combined, dried over anhydrous sodium sulfate, filtered to remove the desiccant, and concentrated to remove solvent under reduced pressure. The residue was purified by column chromatography on silica gel (petroleum ether/ethyl acetate=100/1) to give a target product ethyl 3-carbonyl-3-(4-phenoxyphenyl) propionate 21b (4.0 g, white solid), yield: 50%.

MS m/z (ESI):283[M−1]

Step 2

Ethyl (Z)-3-amino-3-(4-phenoxyphenyl)acryloyl acid ester

Compound ethyl 3-carbonyl-3-(4-phenoxyphenyl) propionate 21b (2.84 g, 10.0 mmol), ammonium formate (3.15 g, 50.0 mmol), molecular sieve (2.0 g), and ethanol (50 mL) were mixed and heated to reflux for 16 hrs. The mixture was cooled to room temperature and filtered. The filtrate was concentrated under reduced pressure, and the residue was purified by column chromatography on silica gel (petroleum ether/ethyl acetate=10/1) to give a target product ethyl (Z)-3-amino-3-(4-phenoxyphenyl)acryloyl acid ester 21c (1.8 g, white solid), yield: 64%.

MS m/z (ESI):284[M+1]

Step 3

Tert-butyl 2-(methoxy(methyl)carbamoyl)pyrrolidine-1-carboxylate

Compound (tert-butoxy carbonyl)proline 21d (5 g, 23 mmol), methoxymethyl amine hydrochloride (2.5 g, 25 mmol), 2-(7-azobenzotriazole)-N,N,N',N'-tetramethyluronium hexafluorophosphate (9.7 g, 25 mmol), diisopropyl ethyl amine (11.5 mL, 69 mmol), and dichloromethane (100 mL) were mixed and stirred at room temperature for 15 hrs. The mixture was desolventized under reduced pressure. The residue was dissolved in ethyl acetate (200 mL), and washed with saturated saline. The organic phase was desolventized under reduced pressure, and the residue was purified by column chromatography on silica gel (petroleum ether/ethyl acetate=5/1 to 1/1) to give a target product tert-butyl 2-(methoxy(methyl)carbamoyl)pyrrolidine-1-carboxylate 21e (5.7 g, colorless oil), yield: 96%.

$^{1}$H NMR (400 MHz, $CDCl_3$) δ 4.78-4.57 (m, 1H), 3.77 (d, J=25.5 Hz, 3H), 3.59 (m, 1H), 3.54-3.38 (m, 1H), 3.22 (s, 3H), 2.20 (m, 1H), 1.93 (m, 3H), 1.46 (d, J=17.8 Hz, 9H).

Step 4 tert-butyl 2-(but-2-ynacyl)pyrrolidine-1-carboxylate

Compound tert-butyl 2-(methoxy(methyl)carbamoyl)pyrrolidine-1-carboxylate 21e (3.5 g, 13.5 mmol) was dissolved in tetrahydrofuran (100 mL). The mixture was cooled to −78° C., and then a propynyl magnesium bromide solution (0.5 M, 54 mL, 27 mmol) was dropwise added. After completion of addition, the mixture was gradually warmed to room temperature and stirred for another 15 hrs. After the completion of reaction, a saturated ammonium chloride solution was added to quench the reaction. The mixture was desolventized under reduced pressure. The residue was diluted with ethyl acetate (200 mL), and washed with saturated saline. The organic phase was desolventized under reduced pressure, and the residue was purified by column chromatography on silica gel (petroleum ether/ethyl acetate=10/1) to give a target product tert-butyl 2-(but-2-ynacyl)pyrrolidine-1-carboxylate 21f (2.45 g, colorless oil), yield: 78%.

$^{1}$H NMR (400 MHz, $CDCl_3$) δ 4.33 (ddd, J=13.9, 8.7, 4.8 Hz, 1H), 3.55 (d, J=6.7 Hz, 2H), 2.33-2.12 (m, 1H), 2.04 (d, J=2.2 Hz, 3H), 2.03-1.80 (m, 3H), 1.46 (d, J=19.1 Hz, 9H).

Step 5

Ethyl 6-(1-(tert-butoxy carbonyl)pyrrolidin-2-yl)-4-methyl-2-(4-phenoxyphenyl)nicotine acid ester Compound ethyl (Z)-3-amino-3-(4-phenoxyphenyl)acryloyl acid ester 21c (980 mg, 3.5 mmol), tert-butyl 2-(but-2-ynacyl)pyrrolidine-1-carboxylate 21f (907 mg, 3.8 mmol), ammonium acetate (267 mg, 3.5 mmol), and ethanol (30 mL) were mixed and heated with stirring at 100° C. for 15 hrs. After the completion of reaction, the mixture was cooled to room temperature, and concentrated to remove solvent under reduced pressure. The residue was purified by column chromatography on silica gel (petroleum ether/ethyl acetate=5/1) to give a target product ethyl 6-(1-(tert-butoxycarbonyl)pyrrolidin-2-yl)-4-methyl-2-(4-phenoxyphenyl) nicotine acid ester 21g (540 mg, yellow solid), yield: 31%.

MS m/z (ESI):503[M+1]

Step 6

6-(1-(tert-butoxycarbonyl)pyrrolidin-2-yl)-4-methyl-2-(4-phenoxyphenyl)nicotinic acid Compound ethyl 6-(1-(tert-butoxycarbonyl)pyrrolidin-2-yl)-4-methyl-2-(4-phenoxyphenyl)nicotine acid ester 21g (140 mg, 0.28 mmol), sodium hydroxide (1.1 g, 28 mmol), water (5 mL), and ethanol (8 mL) were mixed, heated to 88° C., and stirred for 15 hrs. After the completion of reaction, the reaction mixture was adjusted by hydrochloric acid to pH=3, and extracted with ethyl acetate (100 mL). The organic phase was concentrated to remove solvent under reduced pressure, and the residue was purified by column chromatography on silica gel (dichloromethane/methanol=20/1) to give a target product 6-(1-(tert-butoxycarbonyl)pyrrolidin-2-yl)-4-methyl-2-(4-phenoxyphenyl)nicotinic acid 21h (130 mg, colorless oil), yield: 90%.

MS m/z (ESI):475[M+1]

Step 7 tert-butyl 2-(5-amino-4-methyl-6-(4-phenoxyphenyl) pyridin-2-yl)pyrrolidine-1-carboxylate Compound 6-(1-(tert-butoxycarbonyl)pyrrolidin-2-yl)-4-methyl-2-(4-phenoxyphenyl)nicotinic acid 21h (130 mg, 0.27 mmol), diphenylphosphoryl azide (98 mg, 0.324 mmol), triethylamine (36 mg, 0.324 mmol), and acetonitrile (10 mL) were mixed and heated with stirring at 90° C. under Ar atmosphere for 5 hrs. The mixture was cooled to room temperature, and then water was added (2 mL). The mixture was heated for 1 hr at 90° C. under Ar atmosphere. After the completion of reaction, the reaction mixture was concentrated to remove solvent under reduced pressure. The residue was purified by column chromatography on silica gel (petroleum ether/ethyl acetate=1/1) to give a target product tert-butyl 2-(5-amino-4-methyl-6-(4-phenoxyphenyl)pyridin-2-yl)pyrrolidine-1-carboxylate 21i (60 mg, colorless oil), yield: 60%.

MS m/z (ESI):446[M+1]

Step 8

Tert-butyl 2-(5-acetamido-4-methyl-6-(4-phenoxyphenyl)pyridin-2-yl)pyrrolidine-1-carboxylate Compound tert-butyl 2-(5-amino-4-methyl-6-(4-phenoxyphenyl)pyridin-2-yl)pyrrolidine-1-carboxylate 21i (80 mg, 0.18 mmol), acetic anhydride (37 mg, 0.36 mmol), and toluene (10 mL) were mixed and heated with stirring at 90° C. for 15 hrs. The reaction was cooled to room temperature, and concentrated to remove solvent under reduced pressure. The residue was purified by column chromatography on silica gel (petroleum ether/ethyl acetate=5/1) to give a target product tert-butyl 2-(5-acetamido-4-methyl-6-(4-phenoxyphenyl)pyridin-2-yl)pyrrolidine-1-carboxylate 21j (44 mg, colorless oil), yield: 50%.

MS m/z (ESI):488[M+1]

Step 9

Tert-butyl 2-(7-(4-phenoxyphenyl)-1H-pyrazolo[3,4-c]pyridin-5-yl)pyrrolidine-1-carboxylate A mixture of tert-butyl 2-(5-acetamido-4-methyl-6-(4-phenoxyphenyl)pyridin-2-yl)pyrrolidine-1-carboxylate 21j (44 mg, 0.09 mmol), acetic anhydride (28 mg, 0.27 mmol), potassium acetate (12 mg, 0.12 mmol), and benzene (20 mL) was heated to 78° C., and isoamyl nitrite was immediately added (17 mg, 0.14 mmol). The mixture was stirred for 18 hrs, and then cooled to room temperature. The mixture was desolventized under reduced pressure. The residue was dissolved in a mixture of water (5 mL), and ethanol (15 mL), and then lithium hydroxide monohydrate (100 mg) was added and stirred at room temperature for 2 hrs. The mixture was concentrated to remove solvent under reduced pressure, and the residue was dispersed in water (10 mL). The mixture was extracted with ethyl acetate (50 mL×3). The organic phases were combined, dried over anhydrous sodium sulfate, filtered to remove the desiccant, and concentrated to remove solvent under reduced pressure. The residue was purified by column chromatography on silica gel (petroleum ether/ethyl acetate=1/1 to 1/2) to give a target product tert-butyl 2-(7-(4-phenoxyphenyl)-1H-pyrazolo[3,4-c]pyridin-5-yl)pyrrolidine-1-carboxylate 21k (10 mg, yellow solid), yield: 24%.

MS m/z (ESI):457[M+1]

Step 10

7-(4-phenoxyphenyl)-5-(pyrrolidin-2-yl)-1H-pyrazolo[3,4-c]pyridine

Compound tert-butyl 2-(7-(4-phenoxyphenyl)-1H-pyrazolo[3,4-c]pyridin-5-yl)pyrrolidine-1-carboxylate 20k (10 mg, 0.02 mmol), dichloromethane (5 mL), and a solution of hydrogen chloride in ethanol (4 M, 1 mL, 4 mmol) were mixed and stirred at room temperature for 2 hrs. The mixture was desolventized under reduced pressure to produce a target product 7-(4-phenoxyphenyl)-5-(pyrrolidin-2-yl)-1H-pyrazolo[3,4-c]pyridine 21l (5 mg, crude). The product was directly used in the next reaction without further purification.

MS m/z (ESI):357[M+1]

Step 11

1-(2-(7-(4-phenoxyphenyl)-1H-pyrazolo[3,4-c]pyridin-5-yl)pyrrolidin-1-yl)prop-2-en-1-one Compound 7-(4-phenoxyphenyl)-5-(pyrrolidin-2-yl)-1H-pyrazolo[3,4-c]pyridine 20l (5 mg, crude), acryloyl chloride (2 mg, 0.02 mmol), solid sodium bicarbonate (20 mg, 0.24 mmol), water (10 mL), and tetrahydrofuran (20 mL) were mixed and stirred at room temperature for 2 hrs. The mixture was extracted with ethyl acetate (20 mL×3). The organic phases were combined, dried over anhydrous sodium sulfate, filtered to remove the desiccant, and concentrated to remove solvent under reduced pressure. The residue was purified by column chromatography on silica gel (dichloromethane/methanol=20/1) to give a target product 1-(2-(7-(4-phenoxyphenyl)-1H-pyrazolo[3,4-c]pyridin-5-yl)pyrrolidin-1-yl)prop-2-en-1-one 21 (1 mg, white solid), yield: 17%.

MS m/z (ESI):411[M+1]

$^1$H NMR (400 MHz, $CD_3OD$) δ 8.19 (d, J=12.2 Hz, 1H), 8.03 (dd, J=12.4, 8.7 Hz, 2H), 7.53 (d, J=4.5 Hz, 1H), 7.48-7.37 (m, 2H), 7.25-7.17 (m, 2H), 7.13 (d, J=8.3 Hz, 1.5H), 6.80 (dd, J=16.8, 10.5 Hz, 0.5H), 6.39 (dd, J=16.9, 10.1 Hz, 0.5H), 6.24 (m, 1H), 5.79 (dd, J=10.4, 1.9 Hz, 0.5H), 5.53 (dd, J=10.3, 2.0 Hz, 0.5H), 5.46 (s, 1H), 5.36 (t, J=4.7 Hz, 0.5H), 4.09 (d, J=6.3 Hz, 0.5H), 4.00-3.85 (m, 1H), 3.82-3.74 (m, 0.5H), 2.49 (m, 1H), 2.23 (m, 2H), 2.11-1.98 (m, 2H).

Example 22

(S)-1-(3-(7-(4-phenoxyphenyl)-1H-pyrazolo[3,4-c]pyridin-5-yl)pyrrolidin-1-yl)prop-2-en-1-one 22a and (R)-1-(3-(7-(4-phenoxyphenyl)-1H-pyrazolo[3,4-c]pyridin-5-yl)pyrrolidin-1-yl)prop-2-en-1-one 22b 22a

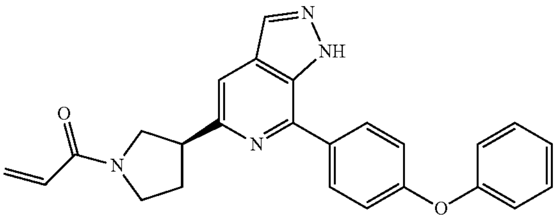

22b

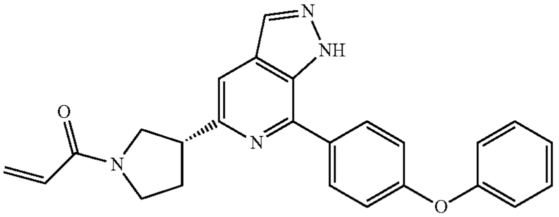

Compound 1-(3-(7-(4-phenoxyphenyl)-1H-pyrazolo[3,4-c]pyridin-5-yl)pyrrolidin-1-yl)prop-2-en-1-one 6 (1.34 g) was resolved by chiral preparative liquid chromatography (chiral column: CHIRALCEL OD-H; gauge: 0.46 cm I.D.× 15 cm L; mobile phase: n-hexane/ethanol=70/30; flow rate: 1.0 mL/min; temperature: 35° C.) to give two optical isomers (one component with a retention time of 7.428 min, 0.61 g; and the other component with a retention time of 10.601 min, 0.70 g). The two optical isomers correspond to 22a and 22b, respectively, but the absolute configurations thereof were not yet identified.

BTK Enzyme Activity Testing

An in vitro kinase assay is used to evaluate the effect of the inventive compounds on Bruton tyrosine kinase (BTK) activity.

The experimental method is generally described as follows:

In vitro activity of BTK is measured by detecting ADP produced in a kinase reaction with an ADP-Glo™ kinase assay kit from Promega Company. In the kinase assay, the kinase consumes ATP to phosphorylate the substrate, while producing ADP. ADP-Glo reagent then terminates the kinase reaction and completely consumes the remaining ATP. Finally, a kinase detection reagent is added to convert generated ADP into new ATP. Luciferase in the detection reagent is capable of catalyzing fluorescein with the participation of ATP and $O_2$ to produce oxidized fluorescein, AMP, and generate light quantum, thereby converting a chemical signal into an optical signal (Luminecence). The intensity of optical signal is positively correlated with the production of ADP in the kinase reaction, so that the activity of kinase BTK can be thereby quantitatively determined.

All assays are conducted at a constant temperature of 23° C., using a Corning 3674 Type white 384-well plate; the BTK kinase (full length with His-Tag) is expressed and purified internally by the company; the substrate of kinase is polypeptide (4:1 Glu,Tyr) (from SignalChem) and ATP (from Sigma); and a microplate reader EnVision (Perkin Elmer) is used for reading an optical signal. The assay buffer includes 40 mM Tris-HCl (pH 7.5), 10 mM $MgCl_2$ (Sigma), 2 mM $MnCl_2$ (Sigma), 0.05 mM DTT (Sigma), and 0.01% BSA (Sigma); the BTK kinase is diluted with the assay buffer to a concentration of 1.6 ng/uL as a kinase reaction solution; and the substrate reaction solution comprises 0.2 mg/mL polypeptide substrate and 50 uM ATP.

Compound's $IC_{50}$ is calculated from 10 concentration points by the following method. The compound is dissolved and diluted in 100% DMSO to a concentration of 1 mM, followed by a serial 3× dilution with DMSO to a minimum concentration of 0.05 uM. Each concentration stock is further diluted 40× with the assay buffer. To a 384-well assay plate are added 1 uL of a series of compound solutions and 2 uL of the kinase reaction solution, followed by mixing homogeneously, and incubating in the dark at room temperature. After in the dark for 30 min, 2 uL of the substrate reaction solution is added to allowed the total reaction volume to 5 uL. The reaction mixture is incubated in the dark at room temperature in the dark for another 60 min. An equal volume of 5 uL ADP-Glo™ reagent is then added to terminate the reaction. The resulting mixture is homogeneously mixed, and stands at room temperature for 40 min. Finally, 10 uL of the kinase detection reagent is added, stands at room temperature for 30 min, and then a value is read on Envision.

Percent inhibition is calculated based on the following equation:

$$\text{Inhibition }\%=[1-(RLU_{compound}-RLU_{min})/(RLU_{max}-RLU_{min})]\times 100$$

wherein $RLU_{compound}$ is the luminescence reading at a given concentration of compound, $RLU_{min}$ is the luminescence reading in the absence of kinase, and $RLU_{max}$ is the luminescence reading in the absence of compound. $IC_{50}$ of the compound is calculated by using a XLfit program in Excel.

| Compound No. | $IC_{50}$(nM) | Compound No. | $IC_{50}$(nM) |
|---|---|---|---|
| 1 | B | 2 | B |
| 3 | A | 4 | A |
| 5 | A | 6 | A |
| 7 | A | 8 | A |
| 9 | A | 10 | A |
| 11 | A | 12 | A |
| 13 | A | 14 | A |
| 15 | A | 16 | C |
| 17 | B | 18 | A |
| 19 | B | 20 | A |
| 21 | A | 22a | A |
| 22b | A | | |

A < 100 nM;

B = 100 to 500 nM;

C > 500 nM

Conclusion: the compounds of the present invention exhibit a significant inhibitory effect on the activity of Bruton tyrosine kinase.

The invention claimed is:

1. A compound represented by formula (I), (I)

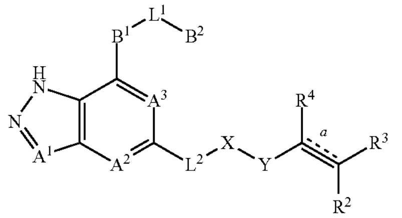

or its tautomers, mesomers, racemates, enantiomers, diastereoisomers, mixtures thereof, or a pharmaceutically acceptable salt thereof:

wherein:

$A^1$, $A^2$ and $A^3$ are each independently selected from the group consisting of $CR^1$ and N;

$B^1$ is independently selected from the group consisting of $C_{3-8}$ cyclic group, 3- to 8-membered heterocyclic group, aryl, and heteroaryl, wherein the cyclic group, heterocyclic group, aryl or heteroaryl is optionally substituted with one or more $G^1$;

$B^2$ is independently selected from the group consisting of H, $C_{3-8}$ cyclic group, 3- to 8-membered heterocyclic group, aryl and heteroaryl, wherein the cyclic group, heterocyclic group, aryl or heteroaryl is optionally substituted with one or more $G^2$;

$L^1$ is independently selected from the group consisting of $-C_{0-2}$ alkyl-, $-CR^5R^6-$, $-C_{1-2}$ alkyl $(R^5)(OH)-$, $-C(O)-$, $-CR^5R^6O-$, $-OCR^5R^6-$, $-SCR^5R^6-$, $-CR^5R^6S-$, $-NR^5-$, $-NR^5C(O)-$, $-C(O)NR^5-$, $-NR^5CONR^6-$, $-CF_2-$, $-O-$, $-S-$, $-S(O)_m-$, $-NR^5S(O)_2-$ and $-S(O)_2NR^5-$;

$L^2$ is independently selected from the group consisting of $-C_{0-4}$ alkyl-, $-C(O)-$, $-O-$, $-NR^7-$, $-NR^7C(O)-$ and $-NR^7S(O)_2-$;

X is independently selected from the group consisting of $C_{0-4}$ alkyl, $C_{3-8}$ cyclic group, 3- to 8-membered heterocyclic group, aryl and heteroaryl, wherein the alkyl, cyclic group, heterocyclic group, aryl or heteroaryl is optionally substituted with one or more $G^3$;

Y is independently selected from the group consisting of $-C(O)-$, $-NR^8C(O)-$, $-S(O)_m-$ and $-NR^8S(O)_m-$;

$R^1$ is independently selected from the group consisting of H, D, $C_{0-4}$ alkyl, halogen and cyano;

bond ≋ is a double bond or a triple bond;

when bond ≋ is a double bond, $R^2$, $R^3$ and $R^4$ are each independently selected from the group consisting of H, D, cyano, halogen, alkyl, cyclic group, heterocyclic group, aryl, and heteroaryl, wherein the alkyl, cyclic group, heterocyclic group, aryl or heteroaryl is optionally substituted with one or more G4; and when bond ≋ is a triple bond, $R^3$ and $R^4$ are absent, and $R^2$ is independently selected from the group consisting of H, D, cyano, halogen, alkyl, cyclic group, heterocyclic group, aryl and heteroaryl, wherein the alkyl, cyclic group, heterocyclic group, aryl or heteroaryl is optionally substituted with one or more $G^4$; wherein $R^3$ and $R^2$, together with the carbon atom attached thereto, can form a ring which contains optionally a heteroatom;

$R^5$, $R^6$, $R^7$ and $R^8$ are each independently selected from the group consisting of H, D, $C_{0-8}$ alkyl, $C_{3-8}$ cyclic group, 3- to 8-membered heterocyclic group, aryl, and heteroaryl, wherein the alkyl, cyclic group, heterocyclic group, aryl or heteroaryl is optionally substituted with one or more $G^5$;

$G^1$, $G^2$, $G^3$, $G^4$ and $G^5$ are each independently selected from the group consisting of H, D, halogen, cyano, alkyl, alkenyl, alkynyl, cyclic group, heterocyclic group, aryl, heteroaryl, $-OR^9$, $-OC(O)NR^9R^{10}$, $-C(O)OR^{10}$, $-C(O)NR^9R^{10}$, $-C(O)R^9$, $-NR^9R^{10}$, $-NR^9C(O)R^{10}$, $-NR^9C(O)NR^{10}R^{11}$, $-S(O)_mR^{10}$ and $-NR^9S(O)_mR^{10}$, wherein the alkyl, alkenyl, alkynyl, cyclic group, heterocyclic group, aryl or heteroaryl is optionally substituted with one or more substituents selected from the group consisting of D, halogen, cyano, $C_{1-8}$ alkyl, $C_{3-8}$ cycloalkyl, 3- to 8-membered heterocyclic group, $-OR^{12}$, $-OC(O)NR^{12}R^{13}$, $-C(O)OR^{12}$, $-C(O)NR^{12}R^{13}$, $-C(O)R^{12}$, $-NR^{12}R^{13}$, $-NR^{12}C(O)R^{13}$, $-NR^{12}C(O)NR^{13}R^{14}$, $-S(O)_mR^{12}$, and $-NR^{12}S(O)_mR^{13}$;

$R^9$, $R^{10}$, $R^{11}$, $R^{12}$, $R^{13}$ and $R^{14}$ are each independently selected from the group consisting of H, $C_{1-6}$ alkyl, $C_1$-$C_6$ heteroalkyl, $C_{3-8}$ cycloalkyl, 3- to 8-membered monocyclic heterocyclic group, monocyclic heteroaryl and monocyclic aryl; and m is 1 or 2.

2. The compound represented by formula (I) or its tautomers, mesomers, racemates, enantiomers, diastereoisomers, mixtures thereof or a pharmaceutically acceptable salt thereof of claim 1, wherein the compound is represented by formula (II), (II)

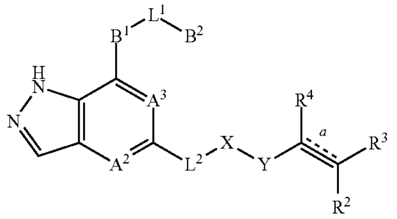

wherein:

$A^2$ and $A^3$ are each independently selected from the group consisting of CH and N;

$B^1$ is independently selected from the group consisting of $C_{3-8}$ cyclic group, 3- to 8-membered heterocyclic group, aryl, and heteroaryl, wherein the cyclic group, heterocyclic group, aryl or heteroaryl is optionally substituted with one or more $G^1$;

$B^2$ is independently selected from the group consisting of H, $C_{3-8}$ cyclic group, 3- to 8-membered heterocyclic group, aryl, and heteroaryl, wherein the cyclic group, heterocyclic group, aryl or heteroaryl is optionally substituted with one or more $G^2$;

$L^1$ is independently selected from the group consisting of $-C_{0-2}$ alkyl-, $-CR^5R^6-$, $-C_{1-2}$ alkyl$(R^5)(OH)-$, —C(O)—, —$CR^5R^6O$—, —$OCR^5R^6$—, —$SCR^5R^6$—, —$CR^5R^6S$—, —$NR^5$—, —$NR^5C(O)$—, —C(O)$NR^5$—, —$NR^5CONR^6$—, —$CF_2$—, —O—, —S—, —$S(O)_m$—, —$NR^5S(O)_2$— and —$S(O)_2NR^5$—;

$L^2$ is independently selected from the group consisting of —$C_{0-4}$ alkyl-, —C(O)—, —O—, —$NR^7$—, —$NR^7C$(O)— and —$NR^7S(O)_2$—;

X is independently selected from the group consisting of $C_{0-4}$ alkyl, $C_{3-8}$ cyclic group, 3- to 8-membered heterocyclic group, aryl, and heteroaryl, wherein the alkyl, cyclic group, heterocyclic group, aryl or heteroaryl is optionally substituted with one or more $G^3$;

Y is independently selected from the group consisting of —C(O)—, —$NR^8C(O)$—, —$S(O)_m$— and —$NR^8S(O)_m$—;

bond ≡ is a double bond or a triple bond;

when bond ≡ is a double bond, $R^2$, $R^3$ and $R^4$ are each independently selected from the group consisting of H, D, cyano, halogen, alkyl, cyclic group, heterocyclic group, aryl and heteroaryl, wherein the alkyl, cyclic group, heterocyclic group, aryl or heteroaryl is optionally substituted with one or more $G^4$; and when bond ≡ is a triple bond, $R^3$ and $R^4$ are absent, $R^2$ is independently selected from the group consisting of H, D, cyano, halogen, alkyl, cyclic group, heterocyclic group, aryl, and heteroaryl, wherein the alkyl, cyclic group, heterocyclic group, aryl or heteroaryl is optionally substituted with one or more $G^4$; wherein $R^3$ and $R^2$ , together with the carbon atom attached thereto, can form a ring which contains optionally a heteroatom;

$R^5$, $R^6$, $R^7$ and $R^8$ are each independently selected from the group consisting of H, D, $C_{0-8}$ alkyl, $C_{3-8}$ cyclic group, 3- to 8-membered heterocyclic group, aryl, and heteroaryl, wherein the alkyl, cyclic group, heterocyclic group, aryl or heteroaryl is optionally substituted with one or more $G^5$;

$G^1$, $G^2$, $G^3$, $G^4$ and $G^5$ are each independently selected from the group consisting of H, D, halogen, cyano, alkyl, alkenyl, alkynyl, cyclic group, heterocyclic group, aryl, heteroaryl, —$OR^9$, —$OC(O)NR^9R^{10}$, —$C(O)OR^{10}$, —$C(O)NR^9R^{10}$, —$C(O)R^9$, —$NR^9R^{10}$, —$NR^9C(O)R^{10}$, —$NR^9C(O)NR^{10}R^{11}$, —$S(O)_mR^{10}$ and —$NR^9S(O)_mR^{10}$, wherein the alkyl, alkenyl, alkynyl, cyclic group, heterocyclic group, aryl or heteroaryl is optionally substituted with one or more substituents selected from the group consisting of D, halogen, cyano, $C_{1-8}$ alkyl, $C_{3-8}$ cycloalkyl, 3- to 8-membered heterocyclic group, —$OR^{12}$, —$OC(O)NR^{12}R^{13}$, —$C(O)OR^{12}$, —$C(O)NR^{12}R^{13}$, —$C(O)R^{12}$, —$NR^{12}R^{13}$, —$NR^{12}C(O)R^{13}$, —$NR^{12}C(O)NR^{13}R^{14}$, —$S(O)_mR^{12}$, and —$NR^{12}S(O)_mR^{13}$;

$R^9$, $R^{10}$, $R^{11}$, $R^{12}$, $R^{13}$ and $R^{14}$ are each independently selected from the group consisting of H, $C_{1-6}$ alkyl, $C_1$-$C_6$ heteroalkyl, $C_{3-8}$ cycloalkyl, 3- to 8-membered monocyclic heterocyclic group, monocyclic heteroaryl and monocyclic aryl; and m is 1 or 2.

3. The compound represented by formula (I) or its tautomers, mesomers, racemates, enantiomers, diastereoisomers, mixtures thereof or a pharmaceutically acceptable salt thereof of claim 1, wherein the compound is represented by formula (III), (III)

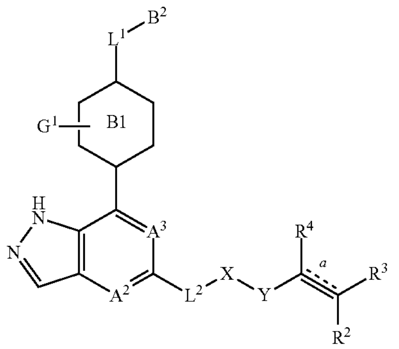

wherein:

$B^1$ is a phenyl ring or 6-membered heteroaryl ring;

$A^2$, $A^3$, $B^2$, $L^1$, $L^2$, X, Y, bond ≡, $R^2$, $R^3$, $R^4$ and $G^1$ are defined as claim 1.

4. The compound represented by formula (I) or its tautomers, mesomers, racemates, enantiomers, diastereoisomers, mixtures thereof or a pharmaceutically acceptable salt thereof of claim 1, wherein the compound is represented by formula (IV), (IV)

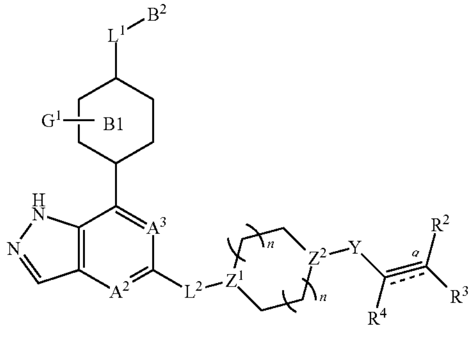

wherein:

$Z^1$ and $Z^2$ are each independently selected from the group consisting of $C(R^a)$ and, N;

$R^a$ is H or alkyl;

n and p are each independently selected from the group consisting of 0, 1 and 2;

$A^2$, $A^3$, $B^1$, $B^2$, $L^1$, $L^2$, Y, bond ≡ $R^2$, $R^3$, $R^4$ and $G^1$ are defined as in claim 1.

5. The compound represented by formula (I) or its tautomers, mesomers, racemates, enantiomers, diastereoisomers, mixtures thereof or a pharmaceutically acceptable salt thereof of claim 1, wherein the compound is represented by formula (V),

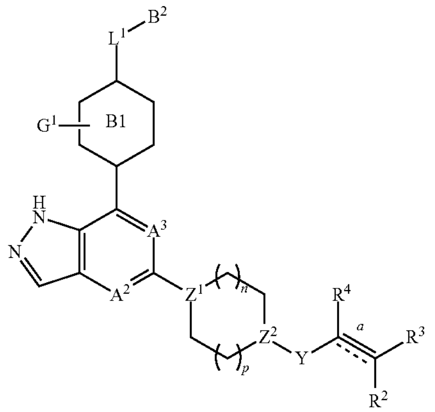
(V)
wherein:
$A^2$, $A^3$, $B^1$, $B^2$, $L^1$, Y, bond $\stackrel{\cdots}{=}$, $R^2$, $R^3$, $R^4$, $G^1$, $Z^1$, $Z^2$, n and p are defined as in claim 1.
6. The compound represented by formula (I) or its tautomers, mesomers, racemates, enantiomers, diastereoisomers, mixtures thereof or a pharmaceutically acceptable salt thereof of claim 1, wherein the compound is:
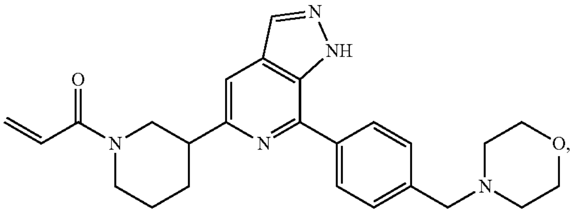
,
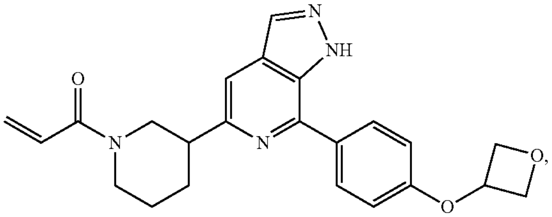
,
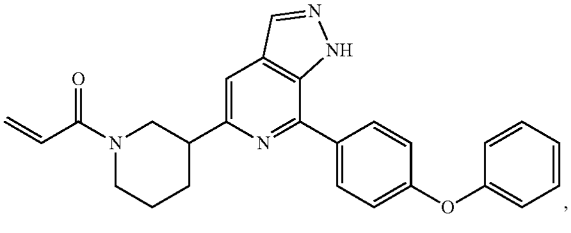
,
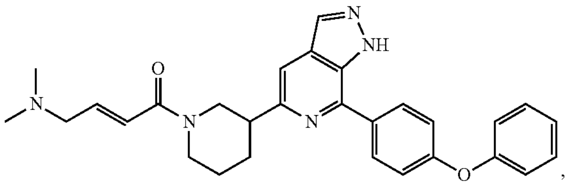
,
-continued
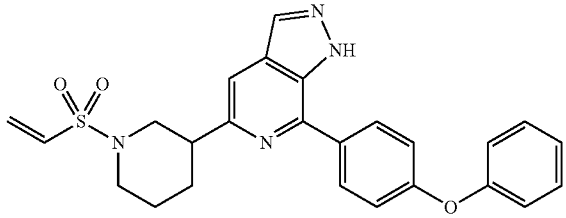
,
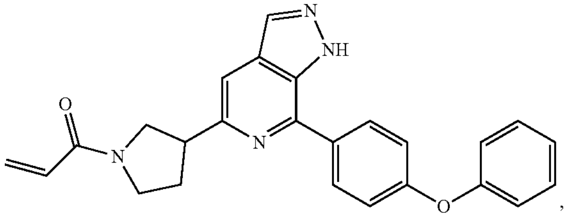
,
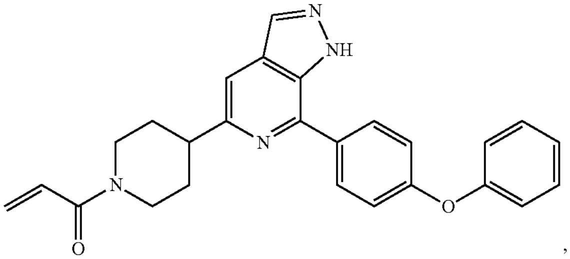
,
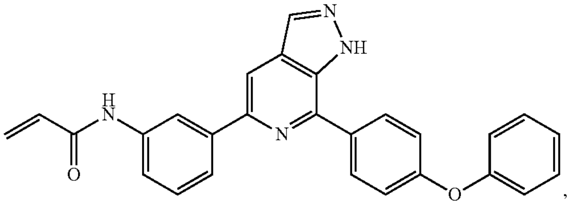
,
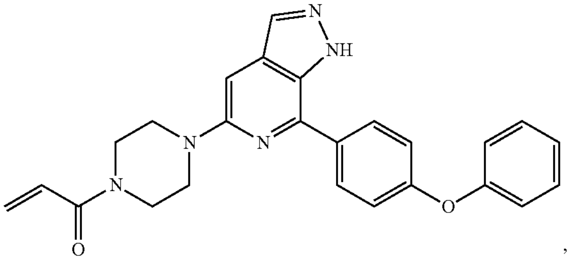
,
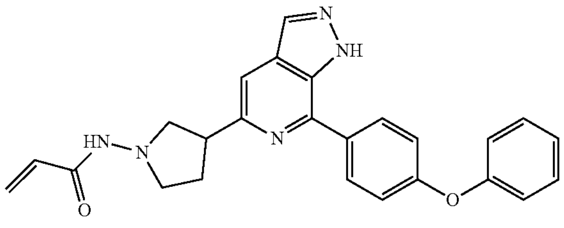
,
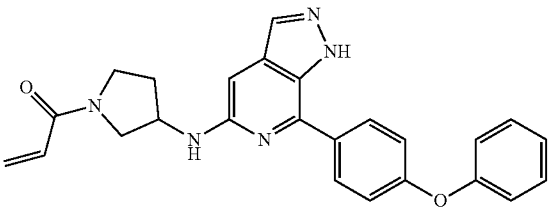
, -continued
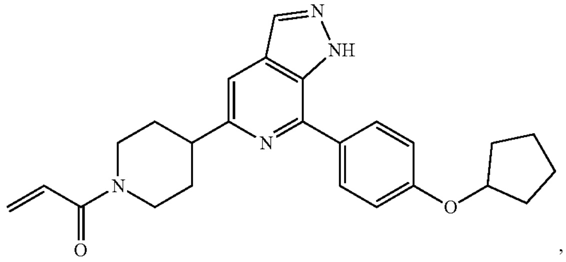
,
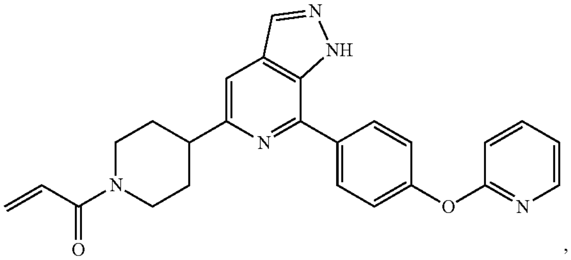
,
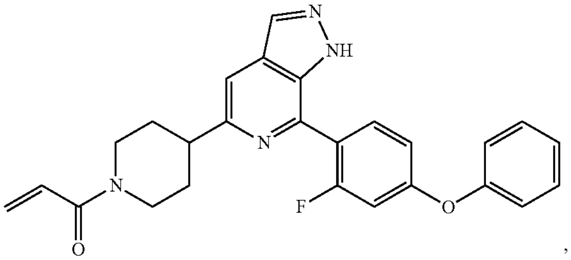
,
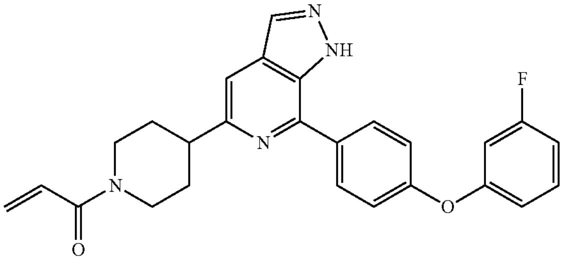
,
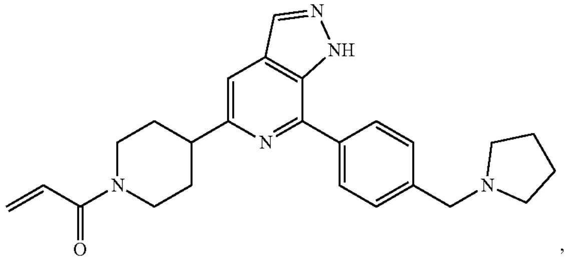
,
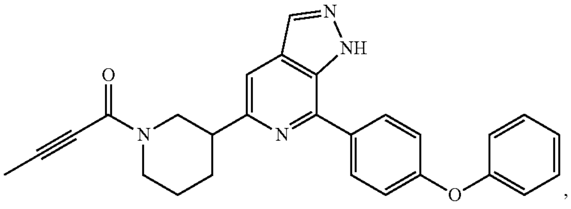
,
-continued
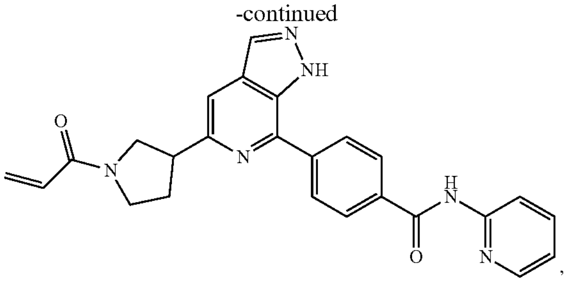
,
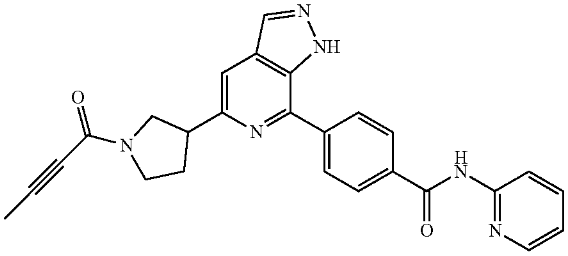
,
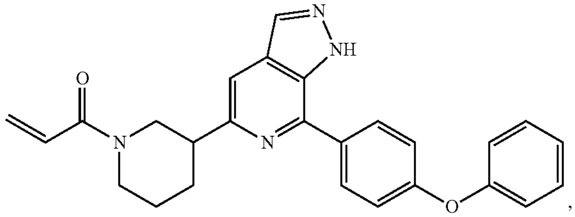
,
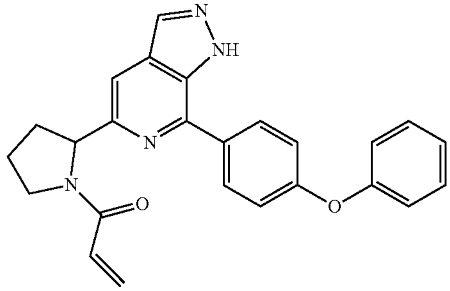
,
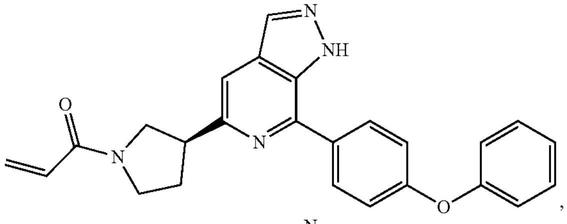
,
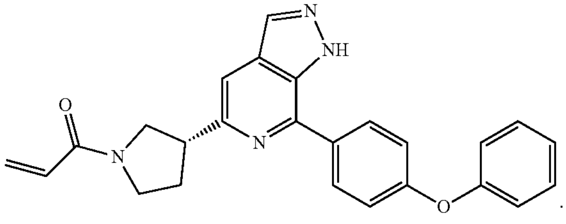 [SMILES: C=CC(=O)N1CC[C@@H](c2cc3cn[nH]c3c(-c3ccc(Oc4ccccc4)cc3)n2)C1]
.
7. A pharmaceutical composition comprising a therapeutically effective amount of a compound represented by formula (I) of claim 1, or its tautomers, mesomers, racemates, enantiomers, diastereoisomers, mixtures thereof or a pharmaceutically acceptable salt thereof, and a pharmaceutically acceptable carrier, diluent, or excipient.
* * * * *